US010724024B2

(12) United States Patent
Grillberger et al.

(10) Patent No.: US 10,724,024 B2
(45) Date of Patent: *Jul. 28, 2020

(54) CELL CULTURE METHODS FOR EXPRESSING ADAMTS PROTEIN

(71) Applicants: Baxalta Incorporated, Bannockburn, IL (US); Baxalta GmbH, Glattpark (Opfikon) (CH)

(72) Inventors: Leopold Grillberger, Vienna (AT); Alexandra Spenger, Vienna (AT); Meinhard Hasslacher, Vienna (AT); Rana Grillberger, Vienna (AT); Manfred Reiter, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/125,688

(22) Filed: Sep. 8, 2018

(65) Prior Publication Data

US 2019/0071660 A1 Mar. 7, 2019

Related U.S. Application Data

(63) Continuation of application No. 15/232,626, filed on Aug. 9, 2016, now Pat. No. 10,072,254, which is a continuation of application No. 14/807,745, filed on Jul. 23, 2015, now Pat. No. 9,441,216, which is a continuation of application No. 14/276,819, filed on May 13, 2014, now Pat. No. 9,127,265, which is a continuation of application No. 13/622,939, filed on Sep. 19, 2012, now Pat. No. 8,759,026, which is a continuation of application No. 12/847,999, filed on Jul. 30, 2010, now Pat. No. 8,313,926.

(60) Provisional application No. 61/230,477, filed on Jul. 31, 2009.

(51) Int. Cl.
C12N 9/64 (2006.01)
C12N 5/071 (2010.01)

(52) U.S. Cl.
CPC ......... C12N 9/6489 (2013.01); C12N 5/0682 (2013.01); C12N 5/0686 (2013.01); C12Y 304/24087 (2013.01); C12N 2500/14 (2013.01); C12N 2500/22 (2013.01); C12N 2500/38 (2013.01); C12N 2500/95 (2013.01); C12N 2500/99 (2013.01); C12N 2510/02 (2013.01)

(58) Field of Classification Search
None
See application file for complete search history.

(56) References Cited

U.S. PATENT DOCUMENTS

| 5,089,411 | A | 2/1992 | Yamada et al. | |
|---|---|---|---|---|
| 8,313,926 | B2 * | 11/2012 | Grillberger | C12N 9/6489 435/69.1 |
| 8,759,026 | B2 * | 6/2014 | Grillberger | C12N 9/6489 435/69.1 |
| 9,127,265 | B2 * | 9/2015 | Grillberger | C12N 9/6489 |
| 9,441,216 | B2 * | 9/2016 | Grillberger | C12N 9/6489 |
| 10,072,254 | B2 * | 9/2018 | Grillberger | C12N 9/6489 |
| 2007/0212770 | A1 | 9/2007 | Grillberger et al. | |
| 2009/0067805 | A1 | 3/2009 | Kuroda et al. | |

FOREIGN PATENT DOCUMENTS

| EP | 0481791 A | 4/1992 |
|---|---|---|
| JP | 02-227069 A | 9/1990 |
| JP | 2001-500735 A | 1/2001 |
| JP | 2007-174978 A | 7/2007 |
| WO | WO 96/15231 A2 | 5/1996 |
| WO | WO 98/08934 A1 | 3/1998 |
| WO | WO 98/12308 A1 | 3/1998 |
| WO | WO 98/15614 A1 | 4/1998 |
| WO | WO 00/03000 A2 | 1/2000 |
| WO | WO 01/23527 A1 | 4/2001 |
| WO | WO 02/42441 A2 | 5/2002 |
| WO | WO 2004/056976 A2 | 7/2004 |
| WO | WO 2007/077217 A2 | 7/2007 |
| WO | WO 2007/077217 A3 | 7/2007 |
| WO | WO 2009/086309 A2 | 7/2009 |
| WO | WO 2009/086309 A3 | 7/2009 |

OTHER PUBLICATIONS

ATCC, "Formulation for DMEM:F-12 Medium ATCC® 30-2006," 1 page.
Adreini et al., "Comparative Analysis of the ADAM and ADAMTS Families," J. Proteome Res., May-Jun. 2005, 4(3):881-888.
Anderson, P.J. et al., "Zinc and Calcium Ions Cooperatively Modulate ADAMTS13 Activity," The Journal of Biological Chemistry, 2006, vol. 281, No. 2, pp. 850-857.
Bevitt, D. J. et al., "Expression of ADAMTS metalloproteinases in the retinal pigment epithelium derived cell line ARPE-19: transcriptional regulation by TNF alpha"; Biochimica et Biophysica Acta—Gene Structure and Expression, Elsevier, vol. 1626, No. 1-3, (2003) pp. 83-91.
Chauhan, A. K. et al., "ADAMTS13: a new link between thrombosis and inflammation," J. Exp. Med. Sep. 1, 2008;205(9):2065-74.
Dent, J. A. et al., "Identification of a cleavage site directing the immunochemical detection of molcular abnormalities in type IIA von Willebrand factor," Proc Natl Acad Sci USA, 1990; 87:6306-6310.

(Continued)

Primary Examiner — Christian L Fronda
(74) Attorney, Agent, or Firm — Morgan, Lewis & Bockius LLP

(57) ABSTRACT

The present invention provides culture mediums that are useful for the expression of ADAMTS proteins, such as ADAMTS13. Methods for the expression and purification of ADAMTS proteins are also provided. In some embodiments, the mediums and methods of the invention are useful for the expression of ADAMTS proteins having high specific activities. Also provided are ADAMTS, e.g., ADAMTS13, protein compositions with high specific activities, which are expressed and purified according to the methods provided herein.

20 Claims, 2 Drawing Sheets

(56) References Cited

OTHER PUBLICATIONS

Dent, J. A. et al., "Heterogeneity of plasma von Willebrand factor multimers resulting from proteolysis of the constituent subunit," *J Clin Invest.*, 1991; 88:774-782.

Franek et al., "Plant Protein Hydrolysates," *Biotechnology Progress*, 2000, vol. 16. pp. 688-692.

Fujikawa, K. et al., "Purification of human von Willebrand factor-cleaving protease and its identification as a new member of the metalloproteinase family," *Blood*, 2001; 98:1662-1666.

Furlan, M. et al., "Triplet structure of von Willebrand factor reflects proteolytic degradation of high molecular weight multimers," *Proc Natl Acad Sci USA*, 1993; 90:7503-7507.

Furlan, M. et al., "Deficient activity of von Willebrand factor-cleaving protease in chronic relapsing thrombotic thrombocytopenic purpura," *Blood*, 1997; 89:3097-3103.

Furlan, M. et al., "Deficiency of von Willebrand factor-cleaving protease in familial and acquired thrombotic thrombocytopenic purpura," *Baillieres Clin Haematol.*, 1998; 11:509-514.

Gardner, M.D. et al., "A functional calcium-binding site in the metalloprotease domain of ADAMTS13," *Blood*, Jan. 29, 2009, vol. 113, No. 5, pp. 1149-1157.

Gerhardt et al., "Crystal Structures of Human ADAMTS-1 Reveal a Conserved Catalytic Domain and a Disintegrin-like Domain with a Fold Homologous to Cysteine-Rich Domains," *J. Mol. Biol.*, Nov. 2, 2007, 373(4):891-902. Epub Aug. 2, 2007.

Gerritsen, H. E. et al., "Partial amino acid sequence of purified von Willebrand factor-cleaving protease," *Blood*, 2001; 98:1654-1661.

Grillberger, L. et al., "Emerging trends in plasma-free manufacturing of recombinant protein therapeutics expressed in mammalian cells," *Biotechnol. J.*, 2009, vol. 4, pp. 186-201.

Ham, R.G. et al., "Clonal Growth of Mammalian Cells in a Chemically Defined, Synthetic Medium," *Proc. N.A.S.*, 1965, vol. 53, pp. 288-293.

Jones, G. C.; "ADAMTS Proteinases: Potential Therapeutic Targets?," *Current Pharmaceutical Biotechnology*, 2006, 7, pp. 25-31.

Kokame, K. et al., "FRETS-VWF73, a first fluorogenic substrate for ADAMTS13 assay," *British Journal of Haematology*, 2005, vol. 129, pp. 93-100.

Kuno, K. et al., "ADAMTS-1 is an Active Metalloproteinase Associated with the Extracellular Matrix," *The Journal of Biological Chemistry*, Jun. 25, 1999, vol. 274, No. 26, pp. 18821-18826.

Larkin, D. et al., "Severe Plasmodium falciparum Malaria is Associated with Circulating Ultra-Large von Willebrand Multimers and ADAMTS13 Inhibition," *PLoS Pathog.* Mar. 2009;5(3):31000349.

Levy, G. G. et al., "Mutations in a member of the ADAMTS gene family cause throbotic thrombocytopenic purpura," *Nature*, 2001; 413:488-494.

Moake J. L. et al., "Unusually large plasma factor VIII:von Willebrand factor multimers in chronic relapsing thrombotic thrombocytopenic purpura," *N Engl J Med.* 1982; 307:1432-1435.

Moake J. L., "Thrombotic microangiopathies," *N. Engl. J. Med.* 2002; 347:589-600.

Moake J. L., "Thrombotic thrombocytopenic purpura and the gemolytic uremic syndrome," *Arch Pathol Lab Med.*, 2002; 126:1430-1433.

Moake J. L., "von Willebrand factor, ADAMTS-13, and thrombotic thrombocytopenic purpura", *Semin. Hematol.* 2004; 41(1):4-14.

Nicholson, A. C. et al., "Functional evolution of ADAMTS genes: Evidence from analyses of phylogeny and gene organization," *BMC Evol. Bio.* 2005, 5:11, pp. 1471-2148.

PCT Search Report for International Appln. No. PCT/US2010/044020, completed Sep. 20, 2010.

Plaimauer, B. et al., "Cloning, expression, and functional characterization of the von Willebrand factor-cleaving protease (ADAMTS13)"; *Blood, American Society of Hematology*, vol. 100, No. 10 (2002) pp. 3626-3632.

Plaimauer, B. et al., "Expression and Characterization of Recombinant Human ADAMTS-13," *Seminars in Hematology*, Jan. 2004, vol. 41, No. 1, pp. 24-33.

Sadler, J. E. et al., "Recent advances in thrombotic thrombocytopenic purpura," *Hematology (Am Soc Hematol Educ Program)* 2004:407-423.

Sadler, J. E., "New concepts in von Willebrand disease," *Annu Rev Med.* 2005; 56:173-191.

Scheiflinger, F. et al., "Recombinant Expression and Functional Characterization of the von Willebrand Factor-Cleaving Protease (ADAMTS13)", *Database Biosis [online]—Blood*, vol. 100, No. 11 (2002), page Abstract No. 475.

Scheiflinger, F. et al., "Nonneutralizing IgM and IgG antibodies to von Willebrand factor-cleaving protease (ADAMTS13) in a patient with thrombotic thrombocytopenic purpura," *Blood*, 2003; 102:3241-3243.

Siedlecki, C. A. et al., "Shear-dependent changes in the three-dimensional structure of human von Willebrand factor," *Blood*, 1996; 88:2939-2950.

Slayter, H. et al., "Native conformation of human von Willebrand protein. Analysis by electron microscopy and quasi-elastic light scattering," *J Biol. Chem.*, 1985; 260:8559-8563.

Soejima, K., et al., "A novel human metalloprotease synthesized in the liver and secreted into the blood: possibly, the von Willebrand factor-cleaving protease," *J Biochem* (Tokyo), 2001; 130:475-480.

Sporn, L. A. et al., "von Willebrand factor released from Weibel-Palade bodies binds more avidly to extracellular matrix than that secreted constitutively," *Blood*, 1987; 69:1531-1534.

Technical Resources—Media Formulations [online] URL:http://www.invitrogen.com/site/us/en/home/support/Product-Technical-Resources/media_formulation.214.html, retrieved on Sep. 7, 2010.

Tsai, H. M. et al., "Endothelial cell-derived high molecular weight von Willebrand factor is converted into the plasma multimer pattern by granulocyte proteases," *Biochem Biophys Res Commun.*, 1989; 158:980-985.

Tsai, H. M. et al., "Multimeric composition of endothelial cell-derived von Willebrand factor," *Blood*, 1989; 73:2074-2076.

Tsai, H. M. et al., "Proteolytic cleavage of recombinant type 2A von Willebrand factor mutants R834W and R834Q: inhibition by doxycycline and by monoclonal antibody VP-1," *Blood*, 1997; 89:1954-1962.

Tsai, H. M. et al., "Antibodies to von Willebrand factor-cleaving protease in acute thrombotic thrombocytopenic purpura," *N Engl J Med.*, 1998; 339:1585-1594.

Tsai, H. M., "von Willebrand factor, ADAMTS13, and thrombotic thrombocytopenic purpura," *J Mol Med.*, 2002; 80:639-647.

Tsai, H. M., "Deficiency of ADAMTS-13 in thrombotic and thrombocytopenic purpura," *J Thromb Haemost.*, 2003; 1:2038-2040.

Wagner, D. D. et al., "Immunolocalization of von Willebrand protein in Weibel-Palade bodies of human endothelial cells," *J Cell Biol*, 1982; 95:355-360.

Wagner, D. D. et al., "von Willebrand factor and the endothelium," *Mayo Clin Proc.*, 1991; 66:621-627.

Zheng, X., et al., "Structure of von Willebrand factor-cleaving protease (ADAMTS13), a metalloprotease involved in thrombotic thrombocytopenic purpura," *J Biol Chem.*, 2001; 276:41059-41063.

Zuquelli, R. et al., "Effect of Sodium Butyrate and Zinc Sulphate Supplementation on Recombinant Human IFN-β Production by Mammalian Cell Culture," *Latin American Applied Research*, 2006, vol. 36, pp. 321-327.

\* cited by examiner

CELL CULTURE METHODS FOR EXPRESSING ADAMTS PROTEIN

CROSS-REFERENCES TO RELATED APPLICATIONS

The present application is a continuation of U.S. patent application Ser. No. 15/232,626, filed Aug. 9, 2016, which is a continuation of U.S. patent application Ser. No. 14/807,745, filed Jul. 23, 2015, which is a continuation of U.S. patent application Ser. No. 14/276,819, filed May 13, 2014, which is a continuation of U.S. patent application Ser. No. 13/622,939, filed Sep. 19, 2012 (now issued as U.S. Pat. No. 8,759,026), which is a continuation of U.S. patent application Ser. No. 12/847,999, filed Jul. 30, 2010 (now issued as U.S. Pat. No. 8,313,926), and claims the benefit of U.S. Provisional Application No. 61/230,477 filed Jul. 31, 2009, which are all expressly incorporated herein by reference in its entirety for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The ADAMTS (a disintegrin and metalloproteinase with thrombospondin type I motifs) proteins are a family of metalloproteinases containing a number of conserved domains, including a zinc-dependant catalytic domain, a cystein-rich domain, a disintegrin-like domain, and at least one, and in most cases multiple, thrombospondin type I repeats (for review, see Nicholson et al., BMC Evol Biol. 2005 Feb. 4; 5(1):11). These proteins, which are evolutionarily related to the ADAM and MMP families of metalloproteinases (Jones G C, Curr Pharm Biotechnol. 2006 February; 7(1):25-31), are secreted enzymes that have been linked to a number of diseases and conditions including thrombotic thrombocytopenic purpura (TTP) (Moake J L, Semin Hematol. 2004 January; 41(1):4-14), connective tissue disorders, cancers, inflammation (Nicholson et al.), and severe *Plasmodium falciparum* malaria (Larkin et al., PLoS Pathog. 2009 March; 5(3):e1000349). Because of these associations, the ADAMTS enzymes have been recognized as potential therapeutic targets for a number of pathologies (Jones G C, Curr Pharm Biotechnol. 2006 February; 7(1): 25-31). Accordingly, methods of producing large yields of ADAMTS proteins having high specific activities, which are free of contaminants such as viruses, BSE, and pathogens like *Mycoplasma* bacteria, are needed.

For cultivation of cells, particularly eukaryotic cells, and more specifically mammalian cells, there is a constant need to use special culture media providing nutrient substances that are required for efficient growth of cells and for the production of biological products, especially biopharmaceuticals, such as, for example, recombinant proteins, antibodies, viruses, viral antigens, and virus-like particles. For the efficient production of said biological products, it is important to achieve an optimal cell density as well as an increase of the protein expression itself in order to obtain maximal product yield.

Cell culture media formulations have been supplemented with a range of additives, including undefined components like fetal calf serum (FCS), several animal derived proteins and/or protein hydrolysates of bovine origin as well as protein hydrolysates derived from plants or yeast.

In general, serum or serum-derived substances, such as, e.g., albumin, transferrin or insulin, may comprise unwanted agents that can contaminate the cell cultures and the biological products obtained thereof. Furthermore, human serum derived additives have to be tested for all known viruses, including hepatitis viruses and HIV which can be transmitted via serum. Moreover, bovine serum and products derived thereof bear the risk of BSE contamination. In addition, all serum-derived products can be contaminated by unknown substances. When using serum or protein additives derived from human or animal sources in cell culture, there are numerous problems (e.g., the varying quality in composition of different batches and the risk of contamination with mycoplasma, viruses or BSE), particularly if the cells are used in the manufacture of drugs or vaccines for human administration.

Therefore, many attempts have been made to provide efficient host systems and cultivation conditions, which do not require serum or other animal protein compounds.

Such serum-free media have been developed on the basis of protein extracts derived from plants or yeast. For example, soy hydrolysates are known to be useful for fermentation processes and can enhance the growth of many fastidious organisms, yeasts and fungi. WO 96/26266 describes that papaic digests of soy meal are a source of carbohydrate and nitrogen and many of the components can be used in tissue culture. Franek et al. (Biotechnology Progress (2000) 16, 688-692) describe growth and productivity promoting effects of defined soy and wheat hydrolysate peptide fractions.

WO 96/15231 discloses a serum-free medium composed of a synthetic minimal essential medium and a yeast extract for the propagation of vertebrate cells and a virus production process. A medium formulation composed of a basal cell culture medium comprising a rice peptide and an extract of yeast and an enzymatic digest thereof, and/or a plant lipid for growth of animal cells is disclosed in WO 98/15614. A medium comprising purified soy hydrolysate for the cultivation of recombinant cells is disclosed in WO 01/23527. WO 00/03000 discloses a medium that comprises a soy hydrolysate and a yeast extract, but also requires the presence of recombinant forms of animal proteins, such as growth factors.

EP-A-0 481 791 describes a biochemically defined culture medium for culturing engineered CHO cells, which is free from protein, lipid and carbohydrate isolated from an animal source, further comprising a recombinant insulin or insulin analogue, 1% to 0.025% w/v papain digested soy peptone and putrescine. WO 98/08934 describes a serum-free eukaryotic cell culture comprising hydrolyzed soy peptides (1-1000 mg/L), 0.01 to 1 mg/L putrescine and a variety of animal-derived components, including albumin, fetuin, various hormones and other proteins. In this context, it should be noted that putrescine is also known to be comprised in standard media like DMEM/Ham's F12 in a concentration of 0.08 mg/L.

The plant and/or yeast hydrolysates, however, are undefined mixtures of oligopeptides and other unknown components and contaminants. Moreover, the quality of commercially available lots of hydrolysates varies extremely. As a result, there are large variations in the production of recombinant proteins or viral products (a variation of up to a factor of three) as a function of the lots of hydrolysates used ("lot-to-lot variation"). This drawback affects the proliferation of the cells as well as the protein expression of each cell. US 2007/0212770 describes various animal protein-free and oligopeptide-free, chemically defined culture mediums that are useful for the large-scale production of recombinant protein biopharmaceuticals.

One ADAMTS family member, ADAMTS13, cleaves von Willebrand factor (vWF) between residues Tyr 1605 and Met 1606, a function responsible for the degradation of large vWF multimers in vivo. Loss of ADAMTS13 activity has been linked to a number of conditions, such as TTP (Moake J L, Semin Hematol. 2004 January; 41(1):4-14), acute and chronic inflammation (Chauhan et al., J Exp Med. 2008 Sep. 1; 205(9):2065-74), and most recently, severe *Plasmodium falciparum* malaria (Larkin et al., PLoS Pathog. 2009 March; 5(3):e1000349).

Thrombotic thrombocytopenic purpura (TTP) is a disorder characterized by thrombotic microangiopathy, thrombocytopenia and microvascular thrombosis that can cause various degrees of tissue ischemia and infarction. Clinically, TTP patients are diagnosed by symptoms such as thrombocytopenia, schistocytes (fragments of erythrocytes) and elevated levels of lactate dehydrogenase (Moake J L. Thrombotic microangiopathies. N Engl J Med. 2002; 347: 589-600; Moake J L. von Willebrand factor, ADAMTS13, and thrombotic thrombocytopenic purpura. Semin Hematol. 2004; 41:4-14; Sadler J E, Moake J L, Miyata T, George J N. Recent advances in thrombotic thrombocytopenic purpura. Hematology (Am Soc Hematol Educ Program). 2004: 407-423; Sadler J E. New concepts in von Willebrand disease. Annu Rev Med. 2005; 56:173-191).

In 1982, Moake et al. found unusually large von Willebrand factor (UL-vWF) multimers in the plasma of the patients with chronic relapsing TTP (Moake J L, Rudy C K, Troll J H, Weinstein M J, Colannino N M, Azocar J, Seder R H, Hong S L, Deykin D. Unusually large plasma factor VIII:von Willebrand factor multimers in chronic relapsing thrombotic thrombocytopenic purpura. N Engl J Med. 1982; 307:1432-1435). The link between UL-vWF and TTP gained support with independent findings by Furlan et al. and Tsai and Lian that most patients suffering from TTP are deficient in a plasma metalloprotease, now known to be ADAMTS13, that cleaves vWF (Furlan M, Robles R, Solenthaler M, Wassmer M, Sandoz P, Laemmle B. Deficient activity of von Willebrand factor-cleaving protease in chronic relapsing thrombotic thrombocytopenic purpura. Blood. 1997; 89:3097-3103; Tsai H M, Sussman, I I, Ginsburg D, Lankhof H, Sixma J J, Nagel R L. Proteolytic cleavage of recombinant type 2A von Willebrand factor mutants R834W and R834Q: inhibition by doxycycline and by monoclonal antibody VP-1. Blood. 1997; 89:1954-1962; Tsai H M, Lian E C. Antibodies to von Willebrand factor-cleaving protease in acute thrombotic thrombocytopenic purpura. N Engl J Med. 1998; 339:1585-1594).

The ADAMTS13 protease is a 190 kDa glycosylated protein produced predominantly by the liver (Levy G G, Nichols W C, Lian E C, Foroud T, McClintick J N, McGee B M, Yang A Y, Siemieniak D R, Stark K R, Gruppo R, Sarode R, Shurin S B, Chandrasekaran V, Stabler S P, Sabio H, Bouhassira E E, Upshaw J D, Jr., Ginsburg D, Tsai H M. Mutations in a member of the ADAMTS gene family cause thrombotic thrombocytopenic purpura. Nature. 2001; 413: 488-494; Fujikawa K, Suzuki H, McMullen B, Chung D. Purification of human von Willebrand factor-cleaving protease and its identification as a new member of the metalloproteinase family. Blood. 2001; 98:1662-1666; Zheng X, Chung D, Takayama T K, Majerus E M, Sadler J E, Fujikawa K. Structure of von Willebrand factor-cleaving protease (ADAMTS13), a metalloprotease involved in thrombotic thrombocytopenic purpura. J Biol Chem. 2001; 276:41059-41063; Soejima K, Mimura N, Hirashima M, Maeda H, Hamamoto T, Nakagaki T, Nozaki C. A novel human metalloprotease synthesized in the liver and secreted into the blood: possibly, the von Willebrand factor-cleaving protease; J Biochem (Tokyo). 2001; 130:475-480; Gerritsen H E, Robles R, Lammle B, Furlan M. Partial amino acid sequence of purified von Willebrand factor-cleaving protease. Blood. 2001; 98:1654-1661).

Mutations in the ADAMTS13 gene have been shown to cause TTP (Levy G G, Nichols W C, Lian E C, Foroud T, McClintick J N, McGee B M, Yang A Y, Siemieniak D R, Stark K R, Gruppo R, Sarode R, Shurin S B, Chandrasekaran V, Stabler S P, Sabio H, Bouhassira E E, Upshaw J D, Jr., Ginsburg D, Tsai H M. Mutations in a member of the ADAMTS gene family cause thrombotic thrombocytopenic purpura. Nature. 2001; 413:488-494). Idiopathic TTP, often caused by autoantibodies inhibiting ADAMTS-13 activity, is a more common disorder that occurs in adults and older children and can recur at regular intervals in 11% to 36% of patients (Tsai H M, Lian E C. Antibodies to von Willebrand factor-cleaving protease in acute thrombotic thrombocytopenic purpura. N Engl J Med. 1998; 339:1585-1594; Furlan M, Lammle B. Deficiency of von Willebrand factor-cleaving protease in familial and acquired thrombotic thrombocytopenic purpura. Baillieres Clin Haematol. 1998; 11:509-514).

Non neutralizing autoantibodies could also inhibit ADAMTS13 activity by inducing clearance from circulation (Scheiflinger F, Knobl P, Trattner B, Plaimauer B, Mohr G, Dockal M, Dorner F, Rieger M. Nonneutralizing IgM and IgG antibodies to von Willebrand factor-cleaving protease (ADAMTS-13) in a patient with thrombotic thrombocytopenic purpura. Blood. 2003; 102:3241-3243). Plasma ADAMTS13 activity in healthy adults ranges from 50% to 178% (Moake J L. Thrombotic thrombocytopenic purpura and the hemolytic uremic syndrome. Arch Pathol Lab Med. 2002; 126:1430-1433). In most patients with familial or acquired TTP, plasma ADAMTS13 activity is absent or less than 5% of normal activity. Without treatment, the mortality rate for TTP exceeds 90%, but plasma therapy has reduced mortality to about 20% (Moake J L. Thrombotic thrombocytopenic purpura and the hemolytic uremic syndrome. Arch Pathol Lab Med. 2002; 126:1430-1433).

vWF synthesized in megakaryocytes and endothelial cells is stored in platelet α-granules and Weibel-Palade bodies, respectively, as ultra large vWF (UL-vWF) (Moake J L, Rudy C K, Troll J H, Weinstein M J, Colannino N M, Azocar J, Seder R H, Hong S L, Deykin D. Unusually large plasma factor VIII:von Willebrand factor multimers in chronic relapsing thrombotic thrombocytopenic purpura. N Engl J Med. 1982; 307:1432-1435; Wagner D D, Olmsted J B, Marder V J. Immunolocalization of von Willebrand protein in Weibel-Palade bodies of human endothelial cells. J Cell Biol. 1982; 95:355-360; Wagner D D, Bonfanti R. von Willebrand factor and the endothelium. Mayo Clin Proc. 1991; 66:621-627; Sporn L A, Marder V J, Wagner D D. von Willebrand factor released from Weibel-Palade bodies binds more avidly to extracellular matrix than that secreted constitutively. Blood. 1987; 69:1531-1534; Tsai H M, Nagel R L, Hatcher V B, Sussman, I I. Endothelial cell-derived high molecular weight von Willebrand factor is converted into the plasma multimer pattern by granulocyte proteases. Biochem Biophys Res Commun. 1989; 158:980-985; Tsai H M, Nagel R L, Hatcher V B, Sussman, I I. Multimeric composition of endothelial cell-derived von Willebrand factor. Blood. 1989; 73:2074-2076). Once secreted from endothelial cells, these UL-vWF multimers are cleaved by ADAMTS13 in circulation into a series of smaller multimers at specific cleavage sites within the vWF molecule (Tsai H M, Nagel R L, Hatcher V B, Sussman, I I. Endothelial cell-derived high molecular weight von Willebrand factor is converted into the plasma multimer pattern by granulocyte proteases. Biochem Biophys Res Commun. 1989; 158:980-985; Dent J A, Galbusera M, Ruggeri Z M. Heterogeneity of plasma von Willebrand factor multimers resulting from proteolysis of the constituent subunit. J Clin Invest. 1991; 88:774-782; Furlan M, Robles R, Affolter D, Meyer D, Baillod P, Lammle B. Triplet structure of von Willebrand factor reflects proteolytic degradation of high molecular weight multimers. Proc Natl Acad Sci USA. 1993; 90:7503-7507).

ADAMTS13 cleaves at the Tyr842-Met843 bond in the central A2 domain of the mature vWF subunit and requires zinc or calcium for activity (Dent J A, Berkowitz S D, Ware J, Kasper C K, Ruggeri Z M. Identification of a cleavage site directing the immunochemical detection of molecular abnormalities in type IIA von Willebrand factor. Proc Natl Acad Sci USA. 1990; 87:6306-6310). vWF exists in "ball-of-yarn" and filamentous form as seen by electron microscopy (Slayter H, Loscalzo J, Bockenstedt P, Handin R I. Native conformation of human von Willebrand protein. Analysis by electron microscopy and quasi-elastic light scattering. J Biol. Chem. 1985; 260:8559-8563). Furthermore, atomic force microscopy confirms that vWF exits in a globular conformation under static conditions and an unfolded filamentous state after exposure to shear stress (Siedlecki C A, Lestini B J, Kottke-Marchant K K, Eppell S J, Wilson D L, Marchant R E. Shear-dependent changes in the three-dimensional structure of human von Willebrand factor. Blood. 1996; 88:2939-2950). This could occur also in vivo when one end of the vWF filament is anchored to a surface.

Thrombi of TTP patients consist of little fibrin and mainly of vWF and platelets, suggesting vWF-mediated platelet aggregation as a cause of thrombosis (Asada Y, Sumiyoshi A, Hayashi T, Suzumiya J, Kaketani K. Immunohistochemistry of vascular lesion in thrombotic thrombocytopenic purpura, with special reference to factor VIII related antigen. Thromb Res. 1985; 38:469-479). Patients with relapsing TTP have ultra-large multimers in the plasma. The UL-vWF multimers accumulate over time because the persistence of the inhibitor (Anti-ADAMTS13 Ab) decreases ADAMTS13 activity. The UL-vWF multimers are hyperactive and unfold as a result of shear stress causing platelet aggregation, resulting in intravascular thrombosis (Tsai H M. Von Willebrand factor, ADAMTS13, and thrombotic thrombocytopenic purpura. J Mol Med. 2002; 80:639-647; Tsai H M. Deficiency of ADAMTS-13 in thrombotic and thrombocytopenic purpura. J Thromb Haemost. 2003; 1:2038-2040; discussion 2040-2035).

It is believed that the presence of hyper-reactive UL-vWF multimers in the plasma due to ADAMTS13 deficiency could be associated with an increased risk of arterial thrombosis linked to coronary heart disease.

As ADAMTS proteins have been implicated in a number of diseases and conditions, there is a need in the art for methods of large scale production of recombinant ADAMTS proteins having high specific activities, which are suitable for pharmaceutical formulation and administration. The present invention provides methods which satisfy these and other needs in the art for the production and purification of ADAMTS proteins.

BRIEF SUMMARY OF THE INVENTION

In one aspect, the present invention provides methods of expressing a disintegrin and metalloproteinase with thrombospondin motifs (ADAMTS) protein. In certain embodiments, the methods provided herein advantageously result in increased expression levels and in the production of ADAMTS proteins with substantially improved activities. These improved properties may be achieved, in one example, by supplementing the culture medium used for the expression of ADAMTS proteins with increased levels of various components, such as calcium, zinc, or nicotinamide (vitamin B3). In a preferred embodiment, the ADAMTS protein is an ADAMTS13 protein.

In another aspect, the invention relates to methods of increasing the expression and/or the activity levels of an ADAMTS protein by culturing recombinant cells harboring a nucleic acid encoding an ADAMTS protein in animal protein-free and chemically defined mediums under batch, fed-batch or continuous cell-culture conditions. In some embodiments, these methods comprise the use of batch, fed-batch, perfusion, or chemostat cell-cultivation that may be performed in either cell suspension or cell adherent fashions. In a preferred embodiment, the ADAMTS protein is an ADAMTS13 protein.

In another aspect, the present invention provides methods of reducing the amount of activity lost during the purification of an ADAMTS protein. In certain embodiments, the methods comprise supplementing purification buffers with additional levels of calcium and/or zinc. In a specific embodiment, the methods relate to stabilizing the activity of an ADAMTS protein during ultrafiltration and/or diafiltration steps used during purification. In a preferred embodiment, the ADAMTS protein is an ADAMTS13 protein.

In yet another aspect, the present invention relates to methods of producing an ADAMTS protein with increased activity for use in the preparation of a pharmaceutical composition. In certain embodiments, these methods comprise the use of animal protein-free and/or chemically defined culture mediums under conditions suitable for increased expression of an ADAMTS protein having increased activities. In a preferred embodiment, the ADAMTS protein is an ADAMTS13 protein.

In a related aspect, the present invention provides animal protein-free, oligopeptide-free, and chemically defined mediums that are useful for the expression of ADAMTS proteins having high specific activities. In a preferred embodiment, the ADAMTS protein is an ADAMTS13 protein.

DETAILED DESCRIPTION OF THE INVENTION

I. Introduction

Figure 1A:
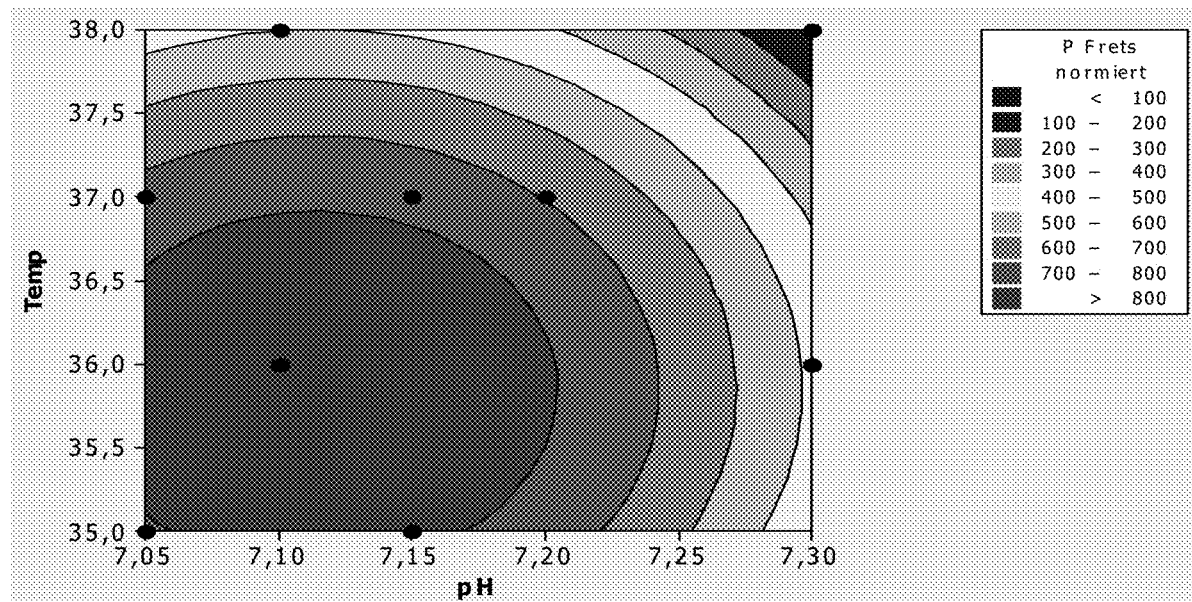
FIG. 1A and FIG. 1B. Volumetric FRETS-vWF73 productivity of recombinant human ADAMTS13 expressed in CHO cells cultured in animal protein-free medium under varying temperature and pH conditions. The results of the various cell-culture experiments are shown as (A) contour plot and (B) surface plot representations of normalized volumetric ADAMTS13 FRETS-VWF73 productivity as a function of culture temperature and pH.

The ADAMTS proteins (i.e., ADAMTS-1 to ADAMTS-20) are a family of secreted zinc metalloproteinases that share a common modular domain organization (for review, see, Flannery C. R., *Front Biosci.* 2006 Jan. 1; 11:544-69). All of the ADAMTS protein share a common core domain architecture, consisting of a signal peptide, followed by a prodomain, a zinc-dependent metalloproteinase catalytic domain, a disintegrin-like domain, a thrombospondin type I repeat, a cysteine-rich domain, and a spacer domain (Apte S. S., *J Biol Chem.* 2009 Nov. 13; 284(46):31493-7). Additionally, all but ADAMTS-4 contain at least one more thrombospondin type I repeat domain, and many of the ADAMTS protein contain one or more additional ancillary domains. Notably, it has been reported that all ADAMTS protein appear to contain at least one calcium binding site and at least one zinc binding site located within the metalloproteinase catalytic domain (Andreini et al., *J. Proteome Res.*, 2005, 4 (3), pp 881-888).

Biological roles for ADAMTS proteins have been reported for various diseases and conditions, including, Antiangiogenesis, Renal interstitial fibrosis, Bone remodeling, Ovarian folliculogenesis, Atherosclerosis, Urogenital development, and Tumor growth/remodeling (ADAMTS-1); Ehler-Danlos syndrome type 7C and Bovine dermatopraxis (ADAMTS-2); Arthritis, Atherosclerosis, and Tendinopathy (ADAMTS-4); Arthritis and Glioblastoma (ADAMTS-5); Arthritis (ADAMTS-7); Antiangiogenesis, Brain malignancy, Arthritis, and Atherosclerosis (ADAMTS-8); Arthritis (ADAMTS-9, -12); Thrombotic thrombocytopenic purpura (ADAMTS-13); and Antithrombosis/stroke (ADAMTS18) (for review, see, Lin and Liu, *Open Access Rheumatology Research and Reviews* 2009:1 121-131).

Recombinant ADAMTS13 (A13) has been expressed before in mammalian cells, however the specific activity varies widely dependent on the cell culture conditions. It has been found that many commercially available culture mediums are not sufficient for expression of A13 with high specific activities, expressed as the ratio of activity, measured by FRETS-VWF73 assay, to antigen content, as determined by ELISA. In one aspect, the methods provided herein are based on several advantageous findings that allow for cell-culture expression of A13 having increased levels of total and specific activity.

The studies described herein demonstrate that a certain minimum concentration of calcium in the culture medium, about 0.5 mM to about 1.5 mM, is required for expression of active A13. Additionally, it was found that by supplementing the culture medium with increased levels of zinc, the resultant expressed A13 protein had higher total and specific activities. For example, in cultures supplemented with additional zinc at 2 to 3 times the normal concentration, as compared to concentrations found in standard chemically defined mediums such as DMEM/F12 based mediums, the specific activity of A13 was significantly increased. Furthermore, an additional increase in the specific activity of A13 could be achieved by increasing the nicotinamide (vitamin B3) concentration from about 2 mg/L, as in standard DMEM/F12 based mediums, to about 7 mg/L. By culturing recombinant CHO or HEK293 cells in mediums supplemented with additional calcium, zinc, and/or nicotinamide, specific activities of at least about 500 mU/µg, 1000 mU/µg, up to about 2000 mU/µg could be achieved in large scale expression cultures of recombinant human A13. These levels of specific activity for recombinantly produced A13 proteins have not been reported previously. Advantageously, these increased levels of A13 activity were achieved in chemically defined medium free of animal derived components, allowing for consistent and reproducible expression of ADAMTS proteins on a large scale suitable for production of proteins for pharmaceutical formulation. Furthermore, these mediums are even free of recombinant proteins, e.g. insulin, resulting in products that can more safely be used in formulations for pharmaceutical administration.

The present disclosure also provides methods that prevent the loss of activity and specific activity during standard ultra/diafiltration and other purification steps. Advantageously, it was found that by supplementing the buffer used for diafiltration with additional calcium and zinc, a significant reduction in the loss of A13 activity, as measured by a FRETS-VWF73 assay, could be achieved.

Accordingly, due to the shared structure-function relationship between the ADAMTS family of secreted metalloproteinases, the methods provided by the present invention allow for the expression of all ADAMTS proteins in cell culture and recovery from the cell medium.

II. Definitions

As used herein, the terms "vitamin B3," "nicotinamide," "niacinamide," "niacin," and "nicotinic acid" may be used interchangeably to refer to any member of the B3 family of vitamins. Accordingly, any member of this family may be used to supplement medium used in the methods of the present invention.

As used herein, an "ADAMTS protein" refers to a polypeptide of the disintegrin and metalloproteinase with thrombospondin type I motifs family of metalloproteinases. Members of this family include the human proteins ADAMTS1 (NM_006988), ADAMTS2 (NM_014244; NM_021599), ADAMTS3 (NM_014243), ADAMTS4 (NM_005099), ADAMTS5 (NM_007038), ADAMTS6 (NM_014273), ADAMTS7 (NM_0142727), ADAMTS8 (NM_007037), ADAMTS9 (NM_182920; NM_182921; NM_020249), ADAMTS10 (NM_030957), ADAMTS12 (NM_030955), ADAMTS13 (NM_139025; NM_139026; NM_139027; NM_139028), ADAMTS14 (NM_139155; NM_080722), ADAMTS15 (NM_139055), ADAMTS16 (NM_139056), ADAMTS17 (NM_139057), ADAMTS18 (NM_199355; NM_139054), ADAMTS19 (NM_133638), and ADAMTS20 (NM_025003, NM_175851). ADAMTS proteins include both full-length proteins and partial polypeptides that display at least partial biological activity, for example, at least 10%, 20%, 30%, 40%, 50%, 60%, 70%, 80%, 90%, or more of the activity demonstrated by the full-length protein, in particular the protease activity demonstrated by the full length protein. In certain instances, an ADAMTS protein will be post-translationally modified either in vivo or in vitro, for example, by enzymatic or chemical means. It is understood that the ADAMTS proteins of the present invention include alternatively spliced isoforms, conservatively modified proteins, substantially identical proteins, homologues, and the like.

In the context of the present invention, an ADAMTS protein embraces any member of the ADAMTS family from, for example, a mammal such as a primate, human, monkey, rabbit, pig, rodent, mouse, rat, hamster, gerbil, canine, feline, and biologically active derivatives thereof. Mutant and variant ADAMTS proteins having activity are also embraced, as are functional fragments and fusion proteins of the ADAMTS proteins. Furthermore, the ADAMTS proteins of the invention may further comprise tags that facilitate purification, detection, or both. The ADAMTS proteins described herein may further be modified with a therapeutic moiety or a moiety suitable imaging in vitro or in vivo.

As used herein, an "ADAMTS13 protein" refers to any protein or polypeptide with ADAMTS13 activity, particularly the ability to cleave the peptide bond between residues Tyr-842 and Met-843 of VWF. In an exemplary embodiment, an ADAMTS13 protein refers to a polypeptide comprising an amino acid sequence that is highly similar to that of NP_620594 (ADAMTS13 isoform 1, preproprotein) or amino acids 75 to 1427 of NP_620594 (ADAMTS13 isoform 1, mature polypeptide). In another embodiment, an ADAMTS13 protein refers to a polypeptide comprising an amino acid sequence that is highly similar to that of NP_620596 (ADAMTS13 isoform 2, preproprotein) or amino acids 75 to 1371 of NP_620594 (ADAMTS13 isoform 2, mature polypeptide). In yet another embodiment, ADAMTS13 proteins include polypeptides comprising an amino acid sequence highly similar to that of NP_620595 (ADAMTS13 isoform 3, preproprotein) or amino acids 75 to 1340 of NP_620595 (ADAMTS13 isoform 1, mature polypeptide). As used herein, an ADAMTS13 protein includes natural variants with vWF cleaving activity and artificial constructs with vWF cleaving activity. As used in the present invention, ADAMTS13 encompasses any natural variants, alternative sequences, isoforms or mutant proteins that retain some basal activity. Examples of ADAMTS13 mutations found in the human population include, without limitation, R7W, V88M, H96D, R102C, R193W, T196I, H234Q, A250V, R268P, W390C, R398H, Q448E, Q456H, P457L, C508Y, R528G, P618A, R625H, I673F, R692C, A732V, S903L, C908Y, C951G, G982R, C1024G, A1033T, R1095W, R1123C, C1213Y, T1226I, G1239V, R1336W, many of which have been found associated with thrombotic thrombocytopenic purpura (TTP). ADAMTS13 proteins also includes polypeptides containing post-translational modifications. For example, ADAMTS13 has been shown to be modified by N-acetylglucosamine (GlcNAc) at residues 614, 667, and 1354, and it has been predicted that residues 142, 146, 552, 579, 707, 828, and 1235 may also be modified in this fashion.

Proteolytically active recombinant ADAMTS13 may be prepared by expression in mammalian cell cultures, as described in Plaimauer et al., (2002, Blood. 15; 100(10): 3626-32) and US 2005/0266528, the disclosures of which are herein incorporated by reference in their entireties for all purposes. Methods of recombinant culture of ADAMTS13 expressing cells are disclosed in Plaimauer B, Scheiflinger F. (Semin Hematol. 2004 January; 41(1):24-33, the disclosure of which is herein incorporated by reference in its entirety for all purposes).

As used herein, "one unit of ADAMTS activity" is defined as the amount of activity in 1 mL of pooled normal human plasma, regardless of the assay being used. For example, when the ADAMTS protein is ADAMTS13, one unit of ADAMTS13 FRETS-VWF73 activity is the amount of activity needed to cleave the same amount of FRETS-VWF73 substrate (Kokame et al., Br J Haematol. 2005 April; 129(1):93-100) as is cleaved by one mL of pooled normal human plasma. Conveniently, ADAMTS13 activity may be determined by functional assays, such as functional assays employing modified von Willebrand factor peptides as substrate for ADAMTS13 (Tripodi et al. *J Thromb Haemost.* 2008 September; 6(9): 1534-41). A preferred method of determining recombinant human ADAMTS13 activity is disclosed in Gerritsen et al. (Assay of von Willebrand factor (vWF)-cleaving protease based on decreased collagen binding affinity of degraded vWF: a tool for the diagnosis of thrombotic thrombocytopenic purpura (TTP). Thromb Haemost 1999; 82: 1386-1389). In one embodiment, to be considered as a ADAMTS13 protein as defined above, a polypeptide or protein must have at least 1% of the vWF cleaving activity of native ADAMTS13. In other embodiments, an ADAMTS13 protein will contain at least 10% of the activity of native ADAMTS13. In yet other embodiments, an ADAMTS13 protein will contain at least 5%, 10%, 20%, 30%, 40%, 50%, 60%, 70%, 80%, 90%, or 100% of the activity of native ADAMTS13. The quantity of an ADAMTS13 protein may also be determined by measurement of an ADAMTS13 antigen, for example using the ELISA method disclosed in Rieger et al., (2006, *Thromb Haemost.* 2006 95(2):212-20).

As used herein, "µg of ADAMTS13" or "µg of ADAMTS13 antigen" means an amount of ADAMTS13 which provides the same level of detectable protein by ELISA assay as 1 mL of pooled normal human plasma. This is based on published estimates of 1 mg of ADAMTS13 being present in 1 mL of normal human plasma, and is thus an approximate measurement.

As used herein, the term "biologically active derivative", when used in the context of an ADAMTS protein, also embraces polypeptides obtained via recombinant DNA technology. This may include any method known in the art for (i) the production of recombinant DNA by genetic engineering, e.g., via reverse transcription of RNA and/or amplification of DNA, (ii) introducing recombinant DNA into prokaryotic or eukaryotic cells by transfection, i.e., via electroporation or microinjection, (iii) cultivating said transformed cells, e.g., in a continuous or batch-wise manner, (iv) expressing an ADAMTS protein, e.g., constitutively or upon induction, and (v) isolating said ADAMTS protein, e.g., from the culture medium or by harvesting the transformed cells, in order to (vi) obtain substantially purified recombinant ADAMTS protein, e.g., via ion exchange chromatography, size exclusion chromatography, affinity chromatography, hydrophobic interaction chromatography, and the like. The term "biologically active derivative" includes also chimeric molecules such as e.g. an ADAMTS protein, or functional fragment thereof, in combination with a second polypeptide, e.g., an immunoglobulin Fc domain or an albumin domain, in order to improve the biological/pharmacological properties such as e.g., half life of the ADAMTS protein in the circulation system of a mammal, particularly a human.

As used herein, the term "ultrafiltration" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular ($10^3$-$10^6$ Da) solutions, especially protein solutions. A number of ultrafiltration membranes are available depending on the size of the molecules they retain. Ultrafiltration is typically characterized by a membrane pore size between 2 nm and 0.05 µm and operating pressures between 1 and 10 bar, and is particularly useful for separating colloids like proteins from small molecules like sugars and salts. In contrast, nanofiltration is another pressure-driven filtration method typically characterized by a membrane pore size between 0.5 and 2 nm and operating pressures between 5 and 40 bar. Nanofiltration is frequently used to achieve a separation between sugars, other organic molecules and multivalent salts on one hand and monovalent salts and water on the other. Generally, ultrafiltration may be performed in either dead-end filtration mode or tangential flow filtration (TFF) mode.

As used herein, the term "diafiltration" refers to another membrane filtration method, sometimes referred to as tangential flow filtration (TFF), wherein the liquid is pumped tangentially along the surface of an ultrafiltration membrane. Typically, the retentate liquid is diluted with diafiltration buffer after passing over the membrane and subsequently returned to the membrane in a continuous flow process. Generally, diafiltration may be performed in either dead-end filtration mode or tangential flow filtration (TFF) mode. As such, a single system may be used for both ultrafiltration and diafiltration operations, for example, to first concentrate the sample using ultrafiltration and then perform buffer exchange by diafiltration.

As used herein, the term "polyamine" refers to any of a group of organic compounds composed of carbon, nitrogen, and hydrogen, and containing two or more amino groups. For example, the term encompasses molecules selected from the group consisting of cadaverine, putrescine, agmatine, ornithine, spermine and spermidine.

In certain embodiments of the chemically defined culture medium used for the expression of an ADAMTS protein, the concentration of the polyamine is present in a concentration ranging from about 0.5 mg/L to about 30 mg/L, or from about 0.5 mg/L to about 20 mg/L, or from about 0.5 mg/L to about 10 mg/L, or from about 1mg/L to about 10 mg/L, or from about 2 mg/L to about 10 mg/L, or from about 2 mg/L to about 8 mg/L, or from about 2 mg/L to about 5 mg/L in the medium. In one specific embodiment, the polyamine is putrescine at a concentration from about 2 mg/L to about 8 mg/L.

As used herein, the term "chemically defined medium" refers to a synthetic growth medium in which the identity and concentration of all the components are known. Chemically defined mediums do not contain bacterial, yeast, animal, or plant extracts, although they may or may not include individual plant or animal-derived components (e.g., proteins, polypeptides, etc.). Non-limiting examples of commercially available chemically defined mediums include, various EX-CELL® mediums (SAFC Biosciences, Inc), various Dulbecco's Modified Eagle's (DME) mediums (Sigma-Aldrich Co; SAFC Biosciences, Inc), Ham's Nutrient Mixture (Sigma-Aldrich Co; SAFC Biosciences, Inc), and the like. Methods of preparing chemically defined culture mediums are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

As used herein, the term "oligopeptide-free culture medium" refers to a protein-free medium that does not comprise oligopeptides, such as, e.g., oligopeptides derived from a protein hydrolysate. In one embodiment, the medium does not comprise oligopeptides having twenty or more amino acids. In one embodiment of the present invention, the medium does not comprise oligopeptides having fifteen or more amino acids. In another embodiment of the invention, the medium does not comprise oligopeptides having ten or more amino acids. In one embodiment the medium does not comprise oligopeptides having seven or more amino acids. In another embodiment the medium does not comprise oligopeptides having five or more amino acids. In still another embodiment the medium does not comprise oligopeptides having three or more amino acids. According to a further embodiment of the present invention, the medium does not comprise oligopeptides having two or more amino acids. Methods of preparing oligopeptide-free culture medium are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

As used herein, the term "serum-free culture medium" refers to a culture medium that is not supplemented with an animal serum. Although oftentimes serum-free mediums are chemically defined mediums, serum-free mediums may be supplemented with discrete animal or plant proteins or protein fractions. Methods of preparing serum-free culture medium are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

As used herein, the term "animal protein-free culture medium" refers to a culture medium that is not supplemented with an animal serum, protein, or protein fraction. Although oftentimes animal protein-free culture mediums are chemically defined mediums, animal protein-free culture mediums may contain plant or yeast hydrolysates. Methods of preparing animal protein-free culture medium are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, the term "about" denotes an approximate range of plus or minus 10% from a specified value. For instance, the language "about 20%" encompasses a range of 18-22%.

III. ADAMTS Protein Expression

In one aspect, the present invention provides methods of expressing a disintegrin and metalloproteinase with thrombospondin motifs (ADAMTS) protein having high specific activity. In one embodiment, the method comprises culturing a cell harboring a nucleic acid encoding an ADAMTS protein in culture medium supplemented with at least one component selected from calcium, zinc, and nicotinamide (Vitamin B3). In a specific embodiment, an ADAMTS protein is expressed in a medium supplemented with at least two components selected from calcium, zinc, and nicotinamide (Vitamin B3). In yet another embodiment, the culture medium is supplemented with calcium, zinc, and nicotinamide (Vitamin B3). In certain embodiments, the culture medium used for the expression of an ADAMTS protein may comprise an animal protein-free, an oligopeptide-free, or a chemically defined medium.

In one aspect, methods are provided for the production of an ADAMTS protein. In one embodiment, the methods comprise the steps of culturing a cell harboring a nucleic acid encoding an ADAMTS protein in a culture medium supplemented with at least one of zinc, calcium, and nicotinamide; removing a fraction of the supernatant from the culture; performing a centrifugation or a filtration step to remove any residual cells; performing an ultrafiltration step to concentrate the ADAMTS protein; and performing a diafiltration step with a buffer comprising at least calcium or zinc. In some embodiments, the concentration of calcium may be at least about 0.1 mM, 0.3 mM, 0.5 mM, 0.75 mM, 1 mM, 1.5 mM, 2 mM, 3 mM, 5 mM or more than 5 mM calcium. In other embodiments, the concentration of zinc may be at least about 0.5 µM, 1 µM, 2 µM, 3 µM, 5 µM, 10 µM or more than 10 µM zinc. In a certain embodiment the harvest, cell free supernatant or the diafiltration buffer contains combinations of calcium and zinc in the above mentioned concentrations. In a certain embodiment the cut off of the ultra and/or diafiltration membranes can be e.g. about 150 kD or 125 kD or 100 kD or 75 kD or 50 kD or 30 kD or 10 kD or less than 10 kD. In a certain embodiment, the ADAMTS protein is ADAMTS13 or a biologically active derivative thereof. In a specific embodiment, the ADAMTS13 protein is a human ADAMTS13 protein or biologically active derivative thereof. In certain embodiments, the culture medium used in the method may be an animal protein-free, oligopeptide-free, or chemically defined medium.

In one embodiment, the method further comprises a purification step selected from the group consisting of ion exchange chromatography, size exclusion chromatography, affinity chromatography, and hydrophobic interaction chromatography.

In yet another embodiment, zinc supplementation may be provided by addition of a protein or polypeptide preparation containing zinc. For example, typical preparations of insulin contain zinc at concentrations such that medium supplementation with between about 1 mg/L and about 10 mg/L insulin would also result in supplementation of about 0.03 µM to about 1.5 µM zinc, as calculated from the detailed monograph for Novolin N InnoLet SubQ, recombinant human insulin, which can be found on the Medscape server. Accordingly, in one embodiment, culture medium used for the expression of an ADAMTS protein may be supplemented with a zinc-containing insulin preparation.

The basal medium, which is supplemented with zinc, calcium, and/or nicotinamide (vitamin B3) as disclosed herein, chosen for culturing the host cell line is not critical to the present invention and may be any one of, or combination of, those known to the art which are suitable for culturing mammalian cells. Medium such as Dulbecco's Modified Eagle Medium, Ham's F-12 Medium, Eagle's Minimal Essential Medium and RPMI-1640 Medium and the like are commercially available. The addition of growth factors such as recombinant insulin is optional.

In one embodiment, the basal medium used to culture a cell expressing an ADAMTS protein (e.g., ADAMTS13) may comprise a mixture of one or more commercially available chemically defined mediums, for example, Dulbecco's Modified Eagle Medium (DMEM) and Ham's F-12 Medium, which has been supplemented with one or more components other than zinc, calcium, and nicotinamide (vitamin B3). Non-limiting examples of components that may be used to supplement a commercially available medium include, essential amino acids (e.g., glutamine), non-ionic surfactants (e.g., Synperonic), primary amines (e.g., ethanolamine), polyamines (e.g., putrescine), trace metals (e.g., iron), and buffering agents (e.g., sodium bicarbonate). In a specific embodiment, the medium is a BCS medium as provided in Table 1. In another specific embodiment, the medium is a BACD medium, for example, BACD-A13 medium.

TABLE 1

| Composition of cell culture medium BCS. | |
|---|---|
| Component | Concentration [g/kg] |
| DMEM/HAM'S F12 | 11.75 |
| L-Glutamine | 0.9 |
| Synperonic | 1.00 |
| Ethanolamine | 0.00153 |
| Putrescine•2HCl | 0.0036 |
| FeSO4•7H2O | 0.0006 |
| NaHCO3 | 2.0 |

Historically, animal cells have been cultured in media containing animal serum. However, such media are incompletely defined and carry the risk of infection. Those in the art have therefore devised "protein-free" media that are either completely free of any protein or at least are free of any protein that is not recombinantly produced. Human serum albumin is commonly used as a serum-free culture supplement for the production of recombinant proteins. Preferred media include those disclosed in U.S. Pat. Nos. 6,171,825 and 6,936,441, WO 2007/077217, and U.S. Patent Application Publication Numbers 2008/0009040 and 2007/0212770.

Optionally, a non-ionic surface-active agent such as a polypropylene glycol (e.g. Pluronic® F-61, Pluronic® F-68, Pluronic® F-71, Pluronic® F-108 or a Synperonic®) maybe added to the medium as a defoaming agent. This agent is generally applied to protect the cells from the negative effects of aeration ("sparging"). The amount of non-ionic surface-active agent may range between 0.05 and 10 g/L, preferably between 0.1 and 5 g/L.

The medium of U.S. Pat. No. 6,936,441 is particularly well suited to the culturing of CHO cells but may be used with other cells as well. A further suitable medium is the oligopeptide-free medium disclosed in U.S. Patent Application No. 2007/0212770 (Baxter International Inc., Baxter Healthcare S.A.).

In one embodiment, the culture medium contains at least about 2 µM zinc. In another embodiment, the culture medium contains between about 2 µM to about 12 µM zinc. In yet another embodiment, the culture medium contains at least about 5 µM zinc. In one embodiment, the culture medium contains between about 5 µM to about 12 µM zinc. In another embodiment, the culture medium contains at least about 0.5 mM calcium. In yet another embodiment, the

TABLE 2

Exemplary concentrations of zinc, calcium, and nicotinamide (vitamin B3) concentration that can be used to supplement culture mediums useful for the expression of an ADAMTS protein.

| | | | | | |
|---|---|---|---|---|---|
| At least 2 µM Zinc | Var. 1 | At least 0.5 mM calcium | Var. 2 | At least 2 mg/L nicotinamide | Var. 3 |
| At least 5 µM Zinc | Var. 4 | At least 1.5 mM calcium | Var. 5 | At least 7 mg/L nicotinamide | Var. 6 |
| Between 2 and 12 µM zinc | Var. 7 | Between 0.5 and 1.5 mM calcium | Var. 8 | Between 2 and 7 mg/L nicotinamide | Var. 9 |
| Between 5 µM and 12 µM zinc | Var. 10 | At least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium | Var. 11 | At least 3 mg/L, 4 mg/L, 5 mg/L, 6 mg/L, 7 mg/L, 8 mg/L, 9 mg/L, 10 mg/L, 15 mg/L, 20 mg/L, or more nicotinamide | Var. 12 |
| At least 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc | Var. 13 | | | | |

*Var. = Variation

In one embodiment, the present invention provides a method for expressing a disintegrin and metalloproteinase with thrombospondin motifs (ADAMTS) protein, the method comprising culturing a cell harboring a nucleic acid encoding an ADAMTS protein in a culture medium comprising at least one of zinc at a concentration of at least about 2 µM or calcium at a concentration of at least about 0.5 mM. In one embodiment, the ADAMTS protein is ADAMTS1. In another embodiment, the ADAMTS protein is ADAMTS2. In another embodiment, the ADAMTS protein is ADAMTS3. In another embodiment, the ADAMTS protein is ADAMTS4. In another embodiment, the ADAMTS protein is ADAMTS5. In another embodiment, the ADAMTS protein is ADAMTS6. In another embodiment, the ADAMTS protein is ADAMTS7. In another embodiment, the ADAMTS protein is ADAMTS8. In another embodiment, the ADAMTS protein is ADAMTS9. In another embodiment, the ADAMTS protein is ADAMTS10. In another embodiment, the ADAMTS protein is ADAMTS11. In another embodiment, the ADAMTS protein is ADAMTS12. In another embodiment, the ADAMTS protein is ADAMTS13. In another embodiment, the ADAMTS protein is ADAMTS14. In another embodiment, the ADAMTS protein is ADAMTS15. In another embodiment, the ADAMTS protein is ADAMTS16. In another embodiment, the ADAMTS protein is ADAMTS17. In another embodiment, the ADAMTS protein is ADAMTS18. In another embodiment, the ADAMTS protein is ADAMTS19. In another embodiment, the ADAMTS protein is ADAMTS20. In a preferred embodiment, the ADAMTS protein is ADAMTS13.

culture medium contains between about 0.5 mM and about 1.5 mM calcium. In one embodiment, the culture medium contains at least about 2 µM zinc and at least about 0.5 mM calcium.

In yet other embodiments, it has been found that the addition of nicotinamide (vitamin B3) further enhances the expression and specific activity of ADAMTS proteins in cell culture. In one embodiment, the culture medium further comprises at least about 2 mg/L nicotinamide (vitamin B3). In another embodiment, the culture medium further comprises at least about 7 mg/L nicotinamide (vitamin B3). In yet another embodiment, the culture medium contains between about 2 mg/L and about 10 mg/L nicotinamide (vitamin B3).

In certain embodiments, the culture medium is an animal protein free culture medium. In another embodiment, the culture medium is a chemically defined medium. In certain embodiments, the culture medium may comprise one or more polyamines. In a particular embodiment, the polyamine is putrescine, for example, at a concentration of at least 0.5 mg/L. In a specific embodiment, the culture medium contains between about 2 mg/L and about 8 mg/L putrescine.

In certain embodiments, the cell or cell line used in the culture is a bacterial cell, a yeast cell, an insect cell, an avian cell, or a mammalian cell. In a specific embodiment, the cell line is a human cell line, a hamster cell line, or a murine cell line. In a more specific embodiment, the cell line is a CHO, BHK, or HEK cell line. In a preferred embodiment, the cell line is a CHO cell line.

In certain embodiments, the nucleic acid encoding the ADAMTS protein comprises a control sequence operably linked to the nucleotide sequence encoding the ADAMTS protein. In one embodiment, the control sequence is a promoter. In certain embodiments, the promoter is a constitutive promoter. In other embodiments, the promoter is an inducible promoter.

In certain embodiments, the methods provided herein comprise the use of a continuous cell culture system (i.e., continuous cell-cultivation). In one embodiment, the continuous culture system is a chemostat culture system (i.e., chemostat cell-cultivation). In another embodiment, the continuous culture system is a turbidostat culture system (i.e., turbidostat cell-cultivation). In yet another embodiment, the continuous culture system is a perfusion culture system (i.e., perfusion cell-cultivation). In certain embodiments, the continuous culture system may be operated under a suspension mode. In other embodiments, the continuous culture system may be operated under an adherent mode. In certain embodiments, the adherent mode comprises the use of a microcarrier, for example, a porous microcarrier.

In certain embodiments, the methods provided herein comprise the use of a batch cell culture system (i.e., batch cell-cultivation). In one embodiment, the batch culture system is a single-batch culture system (i.e., single-batch cell-cultivation). In another embodiment, the batch culture system is a fed-batch culture system (i.e., fed-batch cell-cultivation). In yet another embodiment, the batch culture system is a repeated-batch culture system (i.e., repeated-batch cell-cultivation). In certain embodiments, the batch culture system may be operated under a suspension mode. In other embodiments, the batch culture system may be operated under an adherent mode. In certain embodiments, the adherent mode comprises the use of a microcarrier, for example, a porous microcarrier.

In certain embodiments, the culture will maintained at a temperature between about 35° C. and about 37° C. In other embodiments, the culture will be maintained at a pH of between about 6.9 and about 7.3. In a specific embodiment, the culture will be maintained at a pH of between about 7.05 and about 7.15.

In certain embodiments, the methods provided herein will yield ADAMTS13 proteins in the culture medium (i.e., expressed ADAMTS13) with specific activities of at least 600 U per mg ADAMTS13 protein. In other embodiments, the specific activity will be at least 800 U per mg ADAMTS13 protein. In other embodiments, the specific activity will be at least 1000 U per mg ADAMTS13 protein. In other embodiments, the specific activity will be at least 1500 U per mg ADAMTS13 protein. In other embodiments, the specific activity will be at least 2000 U per mg ADAMTS13 protein.

In other embodiments, the methods provide cultures that yield at least 400 U of ADAMTS13 activity per L of culture per day (U/L/D). In one embodiment, the methods provide cultures that yield at least 800 U of ADAMTS13 activity per L of culture per day (U/L/D).

A. ADAMTS13

In one aspect, the present invention provides methods for expressing an ADAMTS13 protein having increased total and/or specific activity. Advantageously, it was found that by supplementing a growth medium with calcium, zinc, and/or nicotinamide (Vitamin B3), ADAMTS13 polypeptides having high specific activity could be recombinantly expressed and recovered from cell culture.

Methods for the expression of ADAMTS13 are provided in WO 2009/086309, the disclosure of which is herein incorporated by reference in its entirety for all purposes. This reference describes suitable methods and culture conditions, which may be maintained throughout the duration of the culture. As described herein, cell cultures used for the expression of ADAMTS13 proteins will generally be maintained at a temperature at or about between 34° C. and 37° C. and a pH at or about between 6.8 and 7.3.

Ways of monitoring culture temperature and pH are well known in this art and generally rely on probes that are inserted into the bioreactor, or included in loops through which the culture medium is circulated, or inserted into extracted samples of culture medium. Suitable in-line pH sensors include the Mettler Toledo InPro 3100/125/Pt100 sensor (Mettler-Toledo Ingold, Inc., Bedford, Mass.). Ways of altering the specified parameter in order to keep it at the predefined level are also well known. For example, keeping the temperature constant usually involves heating or cooling the bioreactor or the feed medium (if it is a fed-batch or continuous process); keeping the pH constant usually involves choosing and supplying enough of an appropriate buffer (typically bicarbonate) and adding acid, such as hydrochloric acid, or alkali, such as sodium hydroxide, sodium bicarbonate or a mixture thereof, to the feed medium as necessary. It is possible that the calibration of an in-line pH probe may drift over time, such as over periods of days or weeks, during which the cells are cultured. In that event, it may be beneficial to reset the in-line probe by using measurements obtained from a recently calibrated off-line probe.

In one embodiment, the methods comprise culturing a cell harboring a nucleic acid encoding an ADAMTS13 protein in culture medium supplemented with at least one component selected from calcium, zinc, and nicotinamide (Vitamin B3). In a specific embodiment, an ADAMTS protein is expressed in a medium supplemented with at least two components selected from calcium, zinc, and nicotinamide (Vitamin B3). In yet another embodiment, the culture medium is supplemented with calcium, zinc, and nicotinamide (Vitamin B3). In some embodiments, the culture medium may be an animal protein-free, an oligopeptide-free, or a chemically defined culture medium.

1. Zinc Supplementation

Advantageously, it was found that increased ADAMTS13 enzymatic activity and specific activity could be recovered from a cell culture grown in a medium supplemented with zinc. For example, Example 1, demonstrates that ADAMTS13 protein expressed in culture medium containing 1.432 mg/L $ZnSO_4.7H_2O$ (5 µM zinc) has a 40% to 100% higher specific activity than ADAMTS13 protein expressed in culture medium containing only 0.432 mg/L $ZnSO_4.7H_2O$ (1.5 µM zinc) (compare, Table 10 and Table 11). Furthermore, this effect is reproducible, as shown in Example 2 (compare, Table 13 and Table 14); Example 4 (Table 16 to Table 19); and Example 5 (Table 20 and Table 21).

Accordingly, in one aspect, the present invention provides methods for expressing an ADAMTS protein (e.g., ADAMTS13) having an increased specific activity by culturing a cell harboring a nucleic acid encoding an ADAMTS protein (e.g., ADAMTS13) in a culture medium supplemented with zinc, for example, containing at least 2 µM zinc. Similarly, the present invention also provides methods for preparing an ADAMTS protein composition (e.g., an ADAMTS13 composition) having increased total activity or specific activity by culturing a cell harboring a nucleic acid encoding an ADAMTS protein (e.g., ADAMTS13) in a culture medium supplemented with zinc, for example, containing at least 2 µM zinc.

In one embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 µM zinc. In another embodiment, the method comprises culturing a cell harboring a nucleic acid encoding an ADAMTS13 protein in a culture medium comprising at least at or about 5 µM zinc. In one embodiment, the culture medium contains at or about between 2 µM and 12 µM zinc. In another embodiment, the culture medium contains at or about between 5 µM and 12 µM zinc. In yet other embodiments, the culture medium may contain at least at or about 2 µM, or at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc. Suitable zinc concentration ranges are generally determined by cell culture toxicities that may occur in the presence of high concentrations of zinc, e.g., at concentrations greater than 20 µM, 25 µM, 30 µM, 40 µM, and the like. As will be understood by the skilled artisan, the extent to which zinc concentrations are inhibitory to a particular culture system will be highly dependent upon, among other factors, the type of cell used to express an ADAMTS protein, the components of the culture medium utilized, and the operative mode employed for the culture (e.g., batch vs. continuous; suspension vs. adherent; chemostat vs. perfusion; etc.). In certain instances, higher zinc concentrations may be required where components of the culture medium may sequester zinc from the solution, for example, in cases where the culture medium contains albumin. Accordingly, suitable zinc concentration ranges are generally determined by the identity of the cultured cells, medium and operative mode employed. One of skill will readily be able to determine appropriate upper limits for the use of zinc supplementation based on the individual culture system employed.

In one embodiment, a method is provided for expressing a disintegrin and metalloproteinase with thrombospondin motifs 13 (ADAMTS13) protein, comprising culturing a cell harboring a nucleic acid encoding an ADAMTS13 protein in an animal protein and/or polypeptide free culture medium containing at least at or about 2 µM zinc. In another embodiment, the method comprises culturing a cell harboring a nucleic acid encoding an ADAMTS13 protein in an animal protein and/or polypeptide free culture medium comprising at least at or about 5 µM zinc. In one embodiment, the animal protein and/or polypeptide free culture medium contains at or about between 2 µM and 12 µM zinc. In another embodiment, the animal protein and/or polypeptide free culture medium contains at or about between 5 µM and 12 µM zinc. In yet other embodiments, the animal protein and/or polypeptide free culture medium may contain at least at or about 2 µM, or at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method is provided for expressing a disintegrin and metalloproteinase with thrombospondin motifs 13 (ADAMTS13) protein, comprising culturing a cell harboring a nucleic acid encoding an ADAMTS13 protein in a chemically defined culture medium containing at least at or about 2 µM zinc. In another embodiment, the method comprises culturing a cell harboring a nucleic acid encoding an ADAMTS13 protein in a chemically defined culture medium comprising at least at or about 5 µM zinc. In one embodiment, the chemically defined culture medium contains at or about between 2 µM and 12 µM zinc. In another embodiment, the chemically defined culture medium contains at or about between 5 µM and 12 µM zinc. In yet other embodiments, the animal protein and/or polypeptide free culture medium may contain at least at or about 2 µM, or at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc. In certain embodiments, the chemically defined medium will be free of animal derived proteins and/or polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In one embodiment, a method for expressing a disintegrin and metalloproteinase with thrombospondin motifs 13 (ADAMTS13) protein is provided, the method comprising culturing a mammalian cell harboring a nucleic acid encoding an ADAMTS13 protein in a culture medium comprising at least at or about 2 µM zinc. In another embodiment, the method comprises culturing a mammalian cell harboring a nucleic acid encoding an ADAMTS13 protein in a culture medium comprising at least at or about 5 µM zinc. In one embodiment, the method comprises culturing a mammalian cell harboring a nucleic acid encoding an ADAMTS13 protein in a culture medium comprising at or about between 2 µM and 12 µM zinc. In another embodiment, the method comprises culturing a mammalian cell harboring a nucleic acid encoding an ADAMTS13 protein in a culture medium comprising at or about between 5 µM and 12 µM zinc. In yet other embodiments, the method comprises culturing a mammalian cell harboring a nucleic acid encoding an ADAMTS13 protein in a culture medium comprising at least at or about 2 µM, or at least about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In one embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 µM zinc, under continuous or fed-batch culture conditions. In another embodiment, the method comprises culturing a mammalian cell harboring a nucleic acid encoding an ADAMTS13 protein in a culture medium comprising at least at or about 5 µM zinc, under continuous or fed-batch culture conditions. In one embodiment, the method comprises culturing a mammalian cell harboring a nucleic acid encoding an ADAMTS13 protein in a culture medium comprising at or about between 2 µM and 12 µM zinc, under continuous or fed-batch culture conditions. In another embodiment, the method comprises culturing a mammalian cell harboring a nucleic acid encoding an ADAMTS13 protein in a culture medium comprising at or about between 5 μM and 12 μM zinc, under continuous or fed-batch culture conditions. In yet other embodiments, the method comprises culturing a mammalian cell harboring a nucleic acid encoding an ADAMTS13 protein in a culture medium comprising at least at or about 2 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc, under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 μM zinc, wherein the culture is maintained at or about between 35° C. and 37° C. In another embodiment, the method comprises culturing a mammalian cell harboring a nucleic acid encoding an ADAMTS13 protein in a culture medium comprising at least at or about 5 μM zinc, wherein the culture is maintained at or about between 35° C. and 37° C. In one embodiment, the method comprises culturing a mammalian cell harboring a nucleic acid encoding an ADAMTS13 protein in a culture medium comprising at or about between 2 μM and 12 μM zinc, wherein the culture is maintained at or about between 35° C. and 37° C. In another embodiment, the method comprises culturing a mammalian cell harboring a nucleic acid encoding an ADAMTS13 protein in a culture medium comprising at or about between 5 μM and 12 μM zinc, wherein the culture is maintained at or about between 35° C. and 37° C. In yet other embodiments, the method comprises culturing a mammalian cell harboring a nucleic acid encoding an ADAMTS13 protein in a culture medium comprising at least at or about 2 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc, wherein the culture is maintained at or about between 35° C. and 37° C. In a specific embodiment, the culture is maintained at or about 36° C. In one embodiment, the temperature of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 μM zinc, wherein the pH of the culture is maintained at or about between 6.9 and 7.3. In another embodiment, the method comprises culturing a mammalian cell harboring a nucleic acid encoding an ADAMTS13 protein in a culture medium comprising at least at or about 5 μM zinc, wherein the pH of the culture is maintained at or about between 6.9 and 7.3. In one embodiment, the method comprises culturing a mammalian cell harboring a nucleic acid encoding an ADAMTS13 protein in a culture medium comprising at or about between 2 μM and 12 μM zinc, wherein the pH of the culture is maintained at or about between 6.9 and 7.3. In another embodiment, the method comprises culturing a mammalian cell harboring a nucleic acid encoding an ADAMTS13 protein in a culture medium comprising at or about between 5 μM and 12 μM zinc, wherein the pH of the culture is maintained at or about between 6.9 and 7.3. In yet other embodiments, the method comprises culturing a mammalian cell harboring a nucleic acid encoding an ADAMTS13 protein in a culture medium comprising at least at or about 2 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc, wherein the pH of the culture is maintained at or about between 6.9 and 7.3. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In one embodiment, culture medium used for the expression of an ADAMTS protein may be supplemented with zinc at a final concentration of at least about 2 µM to at least about 12 µM. In certain embodiments, the culture medium may be supplemented with zinc at a final concentration of at least about 2 µM, or at least about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or higher levels of zinc. Generally, any zinc salt may be used to supplement the mediums of the invention, non-limiting examples of acceptable salts include, $ZnSO_4.7H_2O$, $ZnSO_3.2H_2O$, $(C_6H_5O_7)_2Zn_3.2H_2O$, $ZnBr_2$, $ZnBr_2.2H_2O$, $ZnCl_2$, $Zn(NO_3)_2.6H_2O$, $Zn(H_2PO_4)_2.H_2O$, $(C_2H_3O_2)_2Zn.2H_2O$, and the like. In certain embodiments, a pharmaceutically acceptable salt of zinc is used to supplement the culture mediums of the invention.

2. Calcium Supplementation

Advantageously, it was found that increased ADAMTS13 enzymatic activity and specific activity could be recovered from a cell culture grown in a medium supplemented with calcium. Traditional cell culture mediums, e.g., DMEM/F12, typically contained about 1 mM calcium. Historically, these high calcium levels were introduced into the medium to assist with adherent cell cultures. Nowadays, however, commercially available mediums designed for suspension cultures contain significantly lower calcium levels, e.g., about 0.1 mM calcium. Such lower calcium levels are relied upon to prevent aggregation of cells cultured via suspension methods. It is known that lower calcium levels are sufficient for propagating cells in suspension and expressing recombinant proteins, however, the inventors have found that these low calcium levels are insufficient for the expression of the ADAMTS proteins (e.g., ADAMTS13).

Accordingly, in one aspect, the present invention provides methods for expressing an ADAMTS protein (e.g., ADAMTS13) having an increased specific activity by culturing a cell harboring a nucleic acid encoding an ADAMTS protein (e.g., ADAMTS13) in a culture medium supplemented with calcium, for example, containing at least 0.5 mM calcium. Similarly, the present invention also provides methods for preparing an ADAMTS protein composition (e.g., an ADAMTS13 composition) having increased total activity or specific activity by culturing a cell harboring a nucleic acid encoding an ADAMTS protein (e.g., ADAMTS13) in a culture medium supplemented with calcium, for example, containing at least 0.5 mM calcium.

In one embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 0.5 mM calcium. In another embodiment, the method comprises culturing a cell harboring a nucleic acid encoding an ADAMTS13 protein in a culture medium comprising at least at or about 1.5 mM calcium. In one embodiment, the culture medium contains at or about between 0.5 mM and 1.5 mM calcium. In yet other embodiments, the culture medium may contain at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium.

In one embodiment, a method is provided for expressing a disintegrin and metalloproteinase with thrombospondin motifs 13 (ADAMTS13) protein, comprising culturing a cell harboring a nucleic acid encoding an ADAMTS13 protein in an animal protein and/or polypeptide free culture medium containing at least at or about 0.5 mM calcium. In another embodiment, the method comprises culturing a cell harboring a nucleic acid encoding an ADAMTS13 protein in an animal protein and/or polypeptide free culture medium comprising at least at or about 1.5 mM calcium. In one embodiment, the animal protein and/or polypeptide free culture medium contains at or about between 0.5 mM and 1.5 mM calcium. In yet other embodiments, the animal protein and/or polypeptide free culture medium may contain at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method is provided for expressing a disintegrin and metalloproteinase with thrombospondin motifs 13 (ADAMTS13) protein, comprising culturing a cell harboring a nucleic acid encoding an ADAMTS13 protein in a chemically defined culture medium containing at least at or about 0.5 mM calcium. In another embodiment, the method comprises culturing a cell harboring a nucleic acid encoding an ADAMTS13 protein in a chemically defined culture medium comprising at least at or about 1.5 mM calcium. In one embodiment, the chemically defined culture medium contains at or about between 0.5 mM and 1.5 mM calcium. In yet other embodiments, the animal protein and/or polypeptide free culture medium may contain at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In certain embodiments, the chemically defined medium will be free of animal derived proteins and/or polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In one embodiment, a method for expressing a disintegrin and metalloproteinase with thrombospondin motifs 13 (ADAMTS13) protein is provided, the method comprising culturing a mammalian cell harboring a nucleic acid encoding an ADAMTS13 protein in a culture medium comprising at least at or about 0.5 mM calcium. In another embodiment, the method comprises culturing a mammalian cell harboring a nucleic acid encoding an ADAMTS13 protein in a culture medium comprising at least at or about 1.5 mM calcium. In one embodiment, the method comprises culturing a mammalian cell harboring a nucleic acid encoding an ADAMTS13 protein in a culture medium comprising at or about between 0.5 mM and 1.5 mM calcium. In yet other embodiments, the method comprises culturing a mammalian cell harboring a nucleic acid encoding an ADAMTS13 protein in a culture medium comprising at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In one embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 0.5 mM calcium, under continuous or fed-batch culture conditions. In another embodiment, the method comprises culturing a mammalian cell harboring a nucleic acid encoding an ADAMTS13 protein in a culture medium comprising at least at or about 1.5 mM calcium, under continuous or fed-batch culture conditions. In one embodiment, the method comprises culturing a mammalian cell harboring a nucleic acid encoding an ADAMTS13 protein in a culture medium comprising at or about between 0.5 mM and 1.5 mM calcium, under continuous or fed-batch culture conditions. In yet other embodiments, the method comprises culturing a mammalian cell harboring a nucleic acid encoding an ADAMTS13 protein in a culture medium comprising at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium, under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 0.5 mM calcium, wherein the culture is maintained at or about between 35° C. and 37° C. In another embodiment, the method comprises culturing a mammalian cell harboring a nucleic acid encoding an ADAMTS13 protein in a culture medium comprising at least at or about 1.5 mM calcium, wherein the culture is maintained at or about between 35° C. and 37° C. In one embodiment, the method comprises culturing a mammalian cell harboring a nucleic acid encoding an ADAMTS13 protein in a culture medium comprising at or about between 0.5 mM and 1.5 mM calcium, wherein the culture is maintained at or about between 35° C. and 37° C. In yet other embodiments, the method comprises culturing a mammalian cell harboring a nucleic acid encoding an ADAMTS13 protein in a culture medium comprising at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium, wherein the culture is maintained at or about between 35° C. and 37° C. In a specific embodiment, the culture is maintained at or about 36° C. In one embodiment, the temperature of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 0.5 mM calcium, wherein the pH of the culture is maintained at or about between 6.9 and 7.3. In another embodiment, the method comprises culturing a mammalian cell harboring a nucleic acid encoding an ADAMTS13 protein in a culture medium comprising at least at or about 1.5 mM calcium, wherein the pH of the culture is maintained at or about between 6.9 and 7.3. In one embodiment, the method comprises culturing a mammalian cell harboring a nucleic acid encoding an ADAMTS13 protein in a culture medium comprising at or about between 0.5 mM and 1.5 mM calcium, wherein the pH of the culture is maintained at or about between 6.9 and 7.3. In yet other embodiments, the method comprises culturing a mammalian cell harboring a nucleic acid encoding an ADAMTS13 protein in a culture medium comprising at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium, wherein the pH of the culture is maintained at or about between 6.9 and 7.3. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 0.5 mM calcium and at least at or about 2 μM zinc. In a related embodiment, the culture medium comprises at least at or about 0.5 mM calcium and at least at or about 5 μM zinc. In another related embodiment, the culture medium comprises at least at or about 0.5 mM calcium and at least at or about between 2 μM zinc and 12 μM zinc. In yet another related embodiment, the culture medium comprises at least at or about 0.5 mM calcium and at least at or about between 5 μM zinc and 12 μM zinc. In certain embodiments, the culture medium comprises at least at or about 0.5 mM calcium and at least at or about 2 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 1.5 mM calcium and at least at or about 2 μM zinc. In a related embodiment, the culture medium comprises at least at or about 1.5 mM calcium and at least at or about 5 μM zinc. In another related embodiment, the culture medium comprises at least at or about 1.5 mM calcium and at least at or about between 2 μM zinc and 12 μM zinc. In yet another related embodiment, the culture medium comprises at least at or about 1.5 mM calcium and at least at or about between 5 μM zinc and 12 μM zinc. In certain embodiments, the culture medium comprises at least at or about 1.5 mM calcium and at least at or about 2 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about between 0.5 mM and 1.5 mM calcium and at least at or about 2 μM zinc. In a related embodiment, the culture medium comprises at least at or about between 0.5 mM and 1.5 mM calcium and at least at or about 5 μM zinc. In another related embodiment, the culture medium comprises at least at or about between 0.5 mM and 1.5 mM calcium and at least at or about between 2 μM zinc and 12 μM zinc. In yet another related embodiment, the culture medium comprises at least at or about between 0.5 mM and 1.5 mM calcium and at least at or about between 5 μM zinc and 12 μM zinc. In certain embodiments, the culture medium comprises at least at or about between 0.5 mM and 1.5 mM calcium and at least at or about 2 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium and at least at or about 2 µM zinc. In a related embodiment, the culture medium comprises at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium and at least at or about 5 µM zinc. In another related embodiment, the culture medium comprises at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium and at least at or about between 2 µM zinc and 12 µM zinc. In yet another related embodiment, the culture medium comprises at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium and at least at or about between 5 µM zinc and 12 µM zinc. In certain embodiments, the culture medium comprises at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium and at least at or about 2 µM, or at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

Generally, any calcium salt may be used to supplement the mediums of the invention. Non-limiting examples of acceptable salts include $CaCl_2$, $CaCl_2$, $CaFPO_3.2H_2O$, $CaI_2$, $CaBr_2$, $(C_2H_3O_2)_2Ca$, $(CHO_2)_2Ca$, $(C_6H_7O_6)_2Ca$, $(C_6H_5O_7)_2Ca_3.2H_2O$, and the like. In certain embodiments, a pharmaceutically acceptable salt of calcium is used to supplement the culture mediums of the invention.

3. Nicotinamide (Vitamin B3) Supplementation

Advantageously, it was found that increased ADAMTS13 enzymatic activity and specific activity could be recovered from a cell culture grown in a medium supplemented with nicotinamide (vitamin B3). For example, Example 2, demonstrates that ADAMTS13 protein expressed in culture medium containing 7 mg/L nicotinamide (vitamin B3) has a 60% higher specific activity than ADAMTS13 protein expressed in culture medium containing only 2 mg/L nicotinamide (Table 13; compare days 4 and 7 with day 11). Surprisingly, this effect is synergistic with zinc supplementation, as expression of ADAMTS13 in medium containing 7 mg/L nicotinamide (vitamin B3) and 5 µM zinc results in a 200% to 300% increase in the specific activity of ADAMTS13 protein (compare Table 14 day 11 with Table 13 days 4 and 7).

Accordingly, in one aspect, the present invention provides methods for expressing an ADAMTS protein (e.g., ADAMTS13) having an increased specific activity by culturing a cell harboring a nucleic acid encoding an ADAMTS protein (e.g., ADAMTS13) in a culture medium supplemented with nicotinamide (vitamin B3), for example, containing at least 2 mg/L nicotinamide (vitamin B3). Similarly, the present invention also provides methods for preparing an ADAMTS protein composition (e.g., an ADAMTS13 composition) having increased total activity or specific activity by culturing a cell harboring a nucleic acid encoding an ADAMTS protein (e.g., ADAMTS13) in a culture medium supplemented with nicotinamide (vitamin B3), for example, containing at least 2 mg/L nicotinamide (vitamin B3).

In one embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 mg/L nicotinamide (vitamin B3). In another embodiment, the method comprises culturing a cell harboring a nucleic acid encoding an ADAMTS13 protein in a culture medium comprising at least at or about 7 mg/L nicotinamide (vitamin B3). In one embodiment, the culture medium contains at or about between 2 mg/L and 10 mg/L nicotinamide (vitamin B3). In yet other embodiments, the culture medium may contain at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3). Suitable nicotinamide (vitamin B3) concentration ranges are generally determined by cell culture toxicities that may occur in the presence of high concentrations of nicotinamide (vitamin B3), e.g., at concentrations greater than 15 mg/L, 20 mg/L, 30 mg/L, 40 mg/L, and the like. As will be understood by the skilled artisan, the extent to which nicotinamide (vitamin B3) concentrations are inhibitory to a particular culture system will be highly dependent upon, among other factors, the type of cell used to express an ADAMTS protein, the components of the culture medium utilized, and the operative mode employed for the culture (e.g., batch vs. continuous; suspension vs. adherent; chemostat vs. perfusion; etc.). In certain instances, higher nicotinamide (vitamin B3) concentrations may be required where components of the culture medium may sequester nicotinamide (vitamin B3) from the solution. Accordingly, suitable nicotinamide (vitamin B3) concentration ranges are generally determined by the identity of the cultured cells, medium and operative mode employed. One of skill will readily be able to determine appropriate upper limits for the use of nicotinamide (vitamin B3) supplementation based on the individual culture system employed.

In one embodiment, a method is provided for expressing a disintegrin and metalloproteinase with thrombospondin motifs 13 (ADAMTS13) protein, comprising culturing a cell harboring a nucleic acid encoding an ADAMTS13 protein in an animal protein and/or polypeptide free culture medium containing at least at or about 2 mg/L nicotinamide (vitamin B3). In another embodiment, the method comprises culturing a cell harboring a nucleic acid encoding an ADAMTS13 protein in an animal protein and/or polypeptide free culture medium comprising at least at or about 7 mg/L nicotinamide (vitamin B3). In one embodiment, the animal protein and/or polypeptide free culture medium contains at or about between 2 mg/L and 10 mg/L nicotinamide (vitamin B3). In yet other embodiments, the animal protein and/or polypeptide free culture medium may contain at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3). In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method is provided for expressing a disintegrin and metalloproteinase with thrombospondin motifs 13 (ADAMTS13) protein, comprising culturing a cell harboring a nucleic acid encoding an ADAMTS13 protein in a chemically defined culture medium containing at least at or about 2 mg/L nicotinamide (vitamin B3). In another embodiment, the method comprises culturing a cell harboring a nucleic acid encoding an ADAMTS13 protein in a chemically defined culture medium comprising at least at or about 7 mg/L nicotinamide (vitamin B3). In one embodiment, the chemically defined culture medium contains at or about between 2 mg/L and 10 mg/L nicotinamide (vitamin B3). In yet other embodiments, the animal protein and/or polypeptide free culture medium may contain at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3). In certain embodiments, the chemically defined medium will be free of animal derived proteins and/or polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In one embodiment, a method for expressing a disintegrin and metalloproteinase with thrombospondin motifs 13 (ADAMTS13) protein is provided, the method comprising culturing a mammalian cell harboring a nucleic acid encoding an ADAMTS13 protein in a culture medium comprising at least at or about 2 mg/L nicotinamide (vitamin B3). In another embodiment, the method comprises culturing a mammalian cell harboring a nucleic acid encoding an ADAMTS13 protein in a culture medium comprising at least at or about 7 mg/L nicotinamide (vitamin B3). In one embodiment, the method comprises culturing a mammalian cell harboring a nucleic acid encoding an ADAMTS13 protein in a culture medium comprising at or about between 2 mg/L and 10 mg/L nicotinamide (vitamin B3). In yet other embodiments, the method comprises culturing a mammalian cell harboring a nucleic acid encoding an ADAMTS13 protein in a culture medium comprising at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3). In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In one embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 mg/L nicotinamide (vitamin B3), under continuous or fed-batch culture conditions. In another embodiment, the method comprises culturing a mammalian cell harboring a nucleic acid encoding an ADAMTS13 protein in a culture medium comprising at least at or about 7 mg/L nicotinamide (vitamin B3), under continuous or fed-batch culture conditions. In one embodiment, the method comprises culturing a mammalian cell harboring a nucleic acid encoding an ADAMTS13 protein in a culture medium comprising at or about between 2 mg/L and 10 mg/L nicotinamide (vitamin B3), under continuous or fed-batch culture conditions. In yet other embodiments, the method comprises culturing a mammalian cell harboring a nucleic acid encoding an ADAMTS13 protein in a culture medium comprising at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3), under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 mg/L nicotinamide (vitamin B3), wherein the culture is maintained at or about between 35° C. and 37° C. In another embodiment, the method comprises culturing a mammalian cell harboring a nucleic acid encoding an ADAMTS13 protein in a culture medium comprising at least at or about 7 mg/L nicotinamide (vitamin B3), wherein the culture is maintained at or about between 35° C. and 37° C. In one embodiment, the method comprises culturing a mammalian cell harboring a nucleic acid encoding an ADAMTS13 protein in a culture medium comprising at or about between 2 mg/L and 10 mg/L nicotinamide, wherein the culture is maintained at or about between 35° C. and 37° C. In yet other embodiments, the method comprises culturing a mammalian cell harboring a nucleic acid encoding an ADAMTS13 protein in a culture medium comprising at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3), wherein the culture is maintained at or about between 35° C. and 37° C. In a specific embodiment, the culture is maintained at or about 36° C. In one embodiment, the temperature of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 mg/L nicotinamide (vitamin B3), wherein the pH of the culture is maintained at or about between 6.9 and 7.3. In another embodiment, the method comprises culturing a mammalian cell harboring a nucleic acid encoding an ADAMTS13 protein in a culture medium comprising at least at or about 7 mg/L nicotinamide (vitamin B3), wherein the pH of the culture is maintained at or about between 6.9 and 7.3. In one embodiment, the method comprises culturing a mammalian cell harboring a nucleic acid encoding an ADAMTS13 protein in a culture medium comprising at or about between 2 mg/L and 10 mg/L nicotinamide (vitamin B3), wherein the pH of the culture is maintained at or about between 6.9 and 7.3. In yet other embodiments, the method comprises culturing a mammalian cell harboring a nucleic acid encoding an ADAMTS13 protein in a culture medium comprising at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3), wherein the pH of the culture is maintained at or about between 6.9 and 7.3. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 mg/L nicotinamide (vitamin B3) and at least at or about 2 μM zinc. In a related embodiment, the culture medium comprises at least at or about 2 mg/L nicotinamide (vitamin B3) and at least at or about 5 μM zinc. In another related embodiment, the culture medium comprises at least at or about 2 mg/L nicotinamide (vitamin B3) and at least at or about between 2 μM zinc and 12 μM zinc. In yet another related embodiment, the culture medium comprises at least at or about 2 mg/L nicotinamide (vitamin B3) and at least at or about between 5 μM zinc and 12 μM zinc. In certain embodiments, the culture medium comprises at least at or about 2 mg/L nicotinamide (vitamin B3) and at least at or about 2 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell.

In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 7 mg/L nicotinamide (vitamin B3) and at least at or about 2 μM zinc. In a related embodiment, the culture medium comprises at least at or about 7 mg/L nicotinamide (vitamin B3) and at least at or about 5 μM zinc. In another related embodiment, the culture medium comprises at least at or about 7 mg/L nicotinamide (vitamin B3) and at least at or about between 2 μM zinc and 12 μM zinc. In yet another related embodiment, the culture medium comprises at least at or about 7 mg/L nicotinamide (vitamin B3) and at least at or about between 5 μM zinc and 12 μM zinc. In certain embodiments, the culture medium comprises at least at or about 7 mg/L nicotinamide (vitamin B3) and at least at or about 2 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about between 2 mg/L and 10 mg/L nicotinamide (vitamin B3) and at least at or about 2 μM zinc. In a related embodiment, the culture medium comprises at least at or about between 2 mg/L and 10 mg/L nicotinamide (vitamin B3) and at least at or about 5 μM zinc. In another related embodiment, the culture medium comprises at least at or about between 2 mg/L and 10 mg/L nicotinamide (vitamin B3) and at least at or about between 2 μM zinc and 12 μM zinc. In yet another related embodiment, the culture medium comprises at least at or about between 2 mg/L and 10 mg/L nicotinamide (vitamin B3) and at least at or about between 5 μM zinc and 12 μM zinc. In certain embodiments, the culture medium comprises at least at or about between 2 mg/L and 10 mg/L nicotinamide (vitamin B3) and at least at or about 2 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3) and at least at or about 2 μM zinc. In a related embodiment, the culture medium comprises at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3) and at least at or about 5 μM zinc. In another related embodiment, the culture medium comprises at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3) and at least at or about between 2 μM zinc and 12 μM zinc. In yet another related embodiment, the culture medium comprises at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3) and at least at or about between 5 μM zinc and 12 μM zinc. In certain embodiments, the culture medium comprises at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3) and at least at or about 2 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 mg/L nicotinamide (vitamin B3) and at least at or about 0.5 mM calcium. In a related embodiment, the culture medium comprises at least at or about 2 mg/L nicotinamide (vitamin B3) and at least at or about 1.5 mM calcium. In another related embodiment, the culture medium comprises at least at or about 2 mg/L nicotinamide (vitamin B3) and at least at or about between 0.5 mM and 1.5 mM calcium. In certain embodiments, the culture medium comprises at least at or about 2 mg/L nicotinamide (vitamin B3) and at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 7 mg/L nicotinamide (vitamin B3) and at least at or about 0.5 mM calcium. In a related embodiment, the culture medium comprises at least at or about 7 mg/L nicotinamide (vitamin B3) and at least at or about 1.5 mM calcium. In another related embodiment, the culture medium comprises at least at or about 7 mg/L nicotinamide (vitamin B3) and at least at or about between 0.5 mM and 1.5 mM calcium. In certain embodiments, the culture medium comprises at least at or about 7 mg/L nicotinamide (vitamin B3) and at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about between 2 mg/L and 10 mg/L nicotinamide (vitamin B3) and at least at or about 0.5 mM calcium. In a related embodiment, the culture medium comprises at least at or about between 2 mg/L and 10 mg/L nicotinamide (vitamin B3) and at least at or about 1.5 mM calcium. In another related embodiment, the culture medium comprises at least at or about between 2 mg/L and 10 mg/L nicotinamide (vitamin B3) and at least at or about between 0.5 mM and 1.5 mM calcium. In certain embodiments, the culture medium comprises at least at or about between 2 mg/L and 10 mg/L nicotinamide (vitamin B3) and at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In another embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3) and at least at or about 0.5 mM calcium. In a related embodiment, the culture medium comprises at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3) and at least at or about 1.5 mM calcium. In another related embodiment, the culture medium comprises at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3) and at least at or about between 0.5 mM and 1.5 mM calcium. In certain embodiments, the culture medium comprises at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3) and at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

In one embodiment, a method for expressing a disintegrin and metalloproteinase with thrombospondin motifs 13 (ADAMTS13) protein is provided, the method comprising culturing a cell harboring a nucleic acid encoding an ADAMTS13 protein in a culture medium comprising zinc, calcium, and nicotinamide (vitamin B3). In certain embodiments, zinc is present in the culture medium at a concentration of at least at or about 2 µM, 5 µM, between 2 µM and 12 µM, between 5 µM and 12 µM, or at least 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more. In certain embodiments, calcium is present in the culture medium at a concentration of at least at or about 0.5 mM, 1.5 mM, between 0.5 and 1.5, or at least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more. In certain embodiments, nicotinamide (vitamin B3) is present in the culture medium at a concentration of at least at or about 2 mg/L, 7 mg/L, between 2 mg/L and 7 mg/L, or at least at or about 3 mg/L, 4 mg/L, 5 mg/L, 6 mg/L, 7 mg/L, 8 mg/L, 9 mg/L, 10 mg/L, 15 mg/L, 20 mg/L, or more.

As expressly disclosed herein, and provided as Var. 14 to Var. 93 (Table 3 to Table 6), any combination of concentrations of the three components (i.e., zinc, calcium, and nicotinamide (vitamin B3)) is contemplated for use in the methods of the invention. In one embodiment, the culture is maintained at or about between 35° C. and 37° C. In a specific embodiment, the culture is maintained at or about 36° C. In one embodiment, the temperature and/or pH of the culture is maintained for at least 7 days. In one embodiment, the method is performed is under continuous or fed-batch culture conditions. In a specific embodiment, the continuous culture condition is a chemostatic culture condition. In another specific embodiment, the continuous culture condition is a perfusion culture condition. In one embodiment, the cell harboring the nucleic acid encoding an ADAMTS13 protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine.

TABLE 3

Exemplary embodiments of culture mediums containing at least 2 mg/L nicotinamide (vitamin B3), which are useful for the expression of an ADAMTS13 protein.

| | At least 0.5 mM calcium | At least 1.5 mM calcium | Between 0.5 mM and 1.5 mM calcium | At least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium |
|---|---|---|---|---|
| At least 2 μM Zinc | Var. 14 | Var. 15 | Var. 16 | Var. 17 |
| At least 5 μM Zinc | Var. 18 | Var. 19 | Var. 20 | Var. 21 |
| Between 2 μM and 12 μM zinc | Var. 22 | Var. 23 | Var. 24 | Var. 25 |
| Between 5 μM and 12 μM zinc | Var. 26 | Var. 27 | Var. 28 | Var. 29 |
| At least 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc | Var. 30 | Var. 31 | Var. 32 | Var. 33 |

*Var. = Variation

TABLE 4

Exemplary embodiments of culture mediums containing at least 7 mg/L nicotinamide (vitamin B3), which are useful for the expression of an ADAMTS13 protein.

| | At least 0.5 mM calcium | At least 1.5 mM calcium | Between 0.5 mM and 1.5 mM calcium | At least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium |
|---|---|---|---|---|
| At least 2 μM Zinc | Var. 34 | Var. 35 | Var. 36 | Var. 37 |
| At least 5 μM Zinc | Var. 38 | Var. 39 | Var. 40 | Var. 41 |
| Between 2 μM and 12 μM zinc | Var. 42 | Var. 43 | Var. 44 | Var. 45 |
| Between 5 μM and 12 μM zinc | Var. 46 | Var. 47 | Var. 48 | Var. 49 |
| At least 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc | Var. 50 | Var. 51 | Var. 52 | Var. 53 |

*Var. = Variation

TABLE 5

Exemplary embodiments of culture mediums containing between 2 and 7 mg/L nicotinamide (vitamin B3), which are useful for the expression of an ADAMTS13 protein.

| | At least 0.5 mM calcium | At least 1.5 mM calcium | Between 0.5 mM and 1.5 mM calcium | At least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium |
|---|---|---|---|---|
| At least 2 μM Zinc | Var. 54 | Var. 55 | Var. 56 | Var. 57 |
| At least 5 μM Zinc | Var. 58 | Var. 59 | Var. 60 | Var. 61 |

TABLE 5-continued

Exemplary embodiments of culture mediums containing between 2 and 7 mg/L nicotinamide (vitamin B3), which are useful for the expression of an ADAMTS13 protein.

| | At least 0.5 mM calcium | At least 1.5 mM calcium | Between 0.5 mM and 1.5 mM calcium | At least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium |
|---|---|---|---|---|
| Between 2 µM and 12 µM zinc | Var. 62 | Var. 63 | Var. 64 | Var. 65 |
| Between 5 µM and 12 µM zinc | Var. 66 | Var. 67 | Var. 68 | Var. 69 |
| At least 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc | Var. 70 | Var. 71 | Var. 72 | Var. 73 |

*Var. = Variation

TABLE 6

Exemplary embodiments of culture mediums containing at least 3 mg/L, 4 mg/L, 5 mg/L, 6 mg/L, 7 mg/L, 8 mg/L, 9 mg/L, 10 mg/L, 15 mg/L, 20 mg/L, or more nicotinamide (vitamin B3), which are useful for the expression of an ADAMTS13 protein.

| | At least 0.5 mM calcium | At least 1.5 mM calcium | Between 0.5 mM and 1.5 mM calcium | At least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium |
|---|---|---|---|---|
| At least 2 µM Zinc | Var. 74 | Var. 75 | Var. 76 | Var. 77 |
| At least 5 µM Zinc | Var. 78 | Var. 79 | Var. 80 | Var. 81 |
| Between 2 µM and 12 µM zinc | Var. 82 | Var. 83 | Var. 84 | Var. 85 |
| Between 5 µM and 12 µM zinc | Var. 86 | Var. 87 | Var. 88 | Var. 89 |
| At least 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc | Var. 90 | Var. 91 | Var. 92 | Var. 93 |

*Var. = Variation

B. Host Cells and Vectors

Recombinant ADAMTS proteins can be produced by expression in any suitable prokaryotic or eukaryotic host system. Examples of eukaryotic cells include, without limitation, mammalian cells, such as CHO, COS, HEK 293, BHK, SK-Hep, and HepG2; insect cells, for example SF9 cells, SF21 cells, S2 cells, and High Five cells; and yeast cells, for example Saccharomyces or Schizosaccharomyces cells. In one embodiment, the ADAMTS proteins can be expressed in bacterial cells, yeast cells, insect cells, avian cells, mammalian cells, and the like. For example, in a human cell line, a hamster cell line, or a murine cell line. In one particular embodiment, the cell line is a CHO, BHK, or HEK cell line. In a preferred embodiment, the cell line is a CHO cell line.

In one embodiment, the cells may be any mammalian cell that can be cultured, preferably in a manufacturing process (i.e., at least 1 liter), to produce a desired ADAMTS protein such as ADAMTS13. Examples include the monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells/-DHFR, such as the DUKX-B11 subclone (CHO, Uriaub and Chasin, *Proc. Natl. Acad. Sci. USA*, 77:4216 (1980)); mouse Sertoli cells (TM4, Mather, *Biol. Reprod*, 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065);

mouse mammary tumor (MMT 060562, ATCC CCL51); TRI cells (Mather et al., *Annals N. Y. Acad. Sci.,* 383:44-68 (1982)); MRC 5 cells; FS4 cells; and the human hepatoma line (Hep G2). Preferably, the cell line is a rodent cell line, especially a hamster cell line such as CHO or BHK.

A wide variety of vectors can be used for the expression of an ADAMTS protein (e.g., ADAMTS13) and can be selected from eukaryotic and prokaryotic expression vectors. In certain embodiments, a plasmid vector is contemplated for use in expressing an ADAMTS protein (e.g., ADAMTS13). In general, plasmid vectors containing replicon and control sequences which are derived from species compatible with the host cell are used in connection with these hosts. The vector can carry a replication site, as well as marking sequences which are capable of providing phenotypic selection in transformed cells. The plasmid will comprise a nucleotide sequence encoding an ADAMTS protein (e.g., ADAMTS13) operable linked to one or more control sequences, for example, a promoter.

A preferred method of preparing stable CHO cell clones expressing a recombinant ADAMTS protein is as follows. A DHFR deficient CHO cell line DUKX-B11 is transfected with a DHFR expression vector to allow for expression of the relevant recombinant protein, essentially as described in U.S. Pat. No. 5,250,421 (Kaufman et al., Genetics Institute, Inc.). Selection is carried out by growth in Hypoxanthine/Thymidine (HT) free media and amplification of the relevant region coding for expression of the recombinant ADAMTS protein and DHFR gene is achieved by propagation of the cells in increasing concentrations of methotrexate. Where appropriate, CHO cell lines may be adapted for growth in serum and/or protein free medium, essentially as described in U.S. Pat. No. 6,100,061 (Reiter et al, lmmuno Aktiengesellschaft).

In another preferred embodiment, stable HEK293 cells are prepared by transfecting with a construct containing a hygromycin selectable marker and selecting transformants by antibiotic resistance.

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Accordingly, in certain embodiments, a viral vector is used to introduce a nucleotide sequence encoding an ADAMTS protein (e.g., ADAMTS13) into a host cell for expression. The viral vector will comprise a nucleotide sequence encoding an ADAMTS protein (e.g., ADAMTS13) operable linked to one or more control sequences, for example, a promoter. Alternatively, the viral vector may not contain a control sequence and will instead rely on a control sequence within the host cell to drive expression of the ADAMTS protein. Non-limiting examples of virus vectors that may be used to deliver a nucleic acid include Adenoviral vectors, AAV vectors, and Retroviral vectors.

In one embodiment, an Adenovirus expression vector include those constructs containing adenovirus sequences sufficient to support packaging of the construct and to ultimately express an ADAMTS construct that has been cloned therein. Adenoviral vectors allow for the introduction of foreign sequences up to 7 kb (Grunhaus et al., Seminar in Virology, 200(2):535-546, 1992)).

In another embodiment, an adeno-associated virus (AAV) can be used to introduce a nucleotide sequence encoding an ADAMTS protein (e.g., ADAMTS13) into a host cell for expression. AAV systems have been described previously and are generally well known in the art (Kelleher and Vos, *Biotechniques,* 17(6):1110-7, 1994; Cotten et al., *Proc Natl Acad Sci USA,* 89(13):6094-6098, 1992; Curiel, *Nat Immun,* 13(2-3):141-64, 1994; Muzyczka, *Curr Top Microbiol Immunol,* 158:97-129, 1992). Details concerning the generation and use of rAAV vectors are described, for example, in U.S. Pat. Nos. 5,139,941 and 4,797,368, each incorporated herein by reference in their entireties for all purposes.

In one embodiment, a retroviral expression vector can be used to introduce a nucleotide sequence encoding an ADAMTS protein (e.g., ADAMTS13) into a host cell for expression. These systems have been described previously and are generally well known in the art (Mann et al., *Cell,* 33:153-159, 1983; Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). In a specific embodiment, the retroviral vector is a lentiviral vector (see, for example, Naldini et al., *Science,* 272(5259):263-267, 1996; Zufferey et al., *Nat Biotechnol,* 15(9):871-875, 1997; Blomer et al., *J Virol.,* 71(9):6641-6649, 1997; U.S. Pat. Nos. 6,013,516 and 5,994,136).

Non-limiting examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived form viral systems such as vaccinia virus, adeno-associated viruses, herpes viruses, retroviruses, etc., using promoters such as CMV, SV40, EF-1, UbC, RSV, ADV, BPV, and β-actin.

In certain embodiments, the cell-culture methods of the invention may comprise the use of a microcarrier. The present invention provides, among other aspect, methods of large-scale ADAMTS protein expression. In some embodiments, the cell-cultures of the embodiments can be performed in large bioreactors under conditions suitable for providing high volume-specific culture surface areas to achieve high cell densities and protein expression. One means for providing such growth conditions is to use microcarriers for cell-culture in stirred tank bioreactors. In another embodiment, these growth requirements are met via the use of a suspension cell culture.

C. Cultivation Methods

In certain embodiments, the methods of the present invention can comprise the use of a cell culture system operated under a batch or continuous mode of operation. For example, when batch cell cultures are utilized, they may be operated under single batch, fed-batch, or repeated-batch mode. Likewise, continuous cell cultures may be operated under, for example, perfusion, turbidostat or chemostat mode. Batch and continuous cell cultivation may be performed under either suspension or adherence conditions. When operated under suspension conditions, the cells will be freely suspended and mixed within the culture medium. Alternatively, under adherence conditions, the cells will be bound to a solid phase, for example, a microcarrier, a porous microcarrier, disk carrier, ceramic cartridge, hollow fiber, flat sheet, gel matrix, and the like.

A batch culture is typically a large scale cell culture in which a cell inoculum is cultured to a maximum density in a tank or fermenter, and harvested and processed as a single batch. A fed-batch culture it typically a batch culture which is supplied with either fresh nutrients (e.g., growth-limiting substrates) or additives (e.g., precursors to products). The feed solution is usually highly concentrated to avoid dilution of the bioreactor. In a repeated-batch culture, the cells are placed in a culture medium and grown to a desired cell density. To avoid the onset of a decline phase and cell death, the culture is then diluted with complete growth medium before the cells reach their maximum concentration. The amount and frequency of dilution varies widely and depends on the growth characteristics of the cell line and convenience of the culture process. The process can be repeated as many times as required and, unless cells and medium are discarded at subculture, the volume of culture will increase stepwise as each dilution is made. The increasing volume may be handled by having a reactor of sufficient size to allow dilutions within the vessel or by dividing the diluted culture into several vessels. The rationale of this type of culture is to maintain the cells in an exponentially growing state. Serial subculture is characterized in that the volume of culture is always increasing stepwise, there can be multiple harvests, the cells continue to grow and the process can continue for as long as desired. In certain embodiments, an ADAMTS protein (e.g., ADAMTS13) may be recovered after harvesting the supernatant of a batch culture.

A continuous culture can be a suspension culture that is continuously supplied with nutrients by the inflow of fresh medium, wherein the culture volume is usually kept constant by the concomitant removal of spent medium. In chemostat and turbidostat methods, the extracted medium contains cells. Thus, the cells remaining in the cell culture vessel must grow to maintain a steady state. In the chemostat method, the growth rate is typically controlled by controlling the dilution rate, i.e., the rate at which fresh medium is added. The growth rate of the cells in the culture may be controlled, for example, at a sub-maximal growth rate, by alteration of the dilution rate. In contrast, in the turbidostat method, the dilution rate is set to permit the maximum growth rate that the cells can achieve at the given operating conditions, such as pH and temperature.

In a perfusion culture, the extracted medium is depleted of cells, which are retained in the culture vessel, for example, by filtration or by centrifugal methods that lead to the reintroduction of the cells into the culture. However, typically membranes used for filtration do not retain 100% of cells, and so a proportion are removed when the medium is extracted. It may not be crucial to operate perfusion cultures at very high growth rates, as the majority of the cells are retained in the culture vessel.

Stirred-tank reactor system can be used for batch and continuous cell cultures operated under suspension or adherent modes. Generally, the stirred-tank reactor system can be operated as any conventional stirred-tank reactor with any type of agitator such as a Rushton, hydrofoil, pitched blade, or marine.

The methods of the invention may comprise the use of fed-batch cell-cultivation or continuous cell-cultivation, such as perfusion or chemostatic cell-cultivation, for the expression of an ADAMTS protein. In certain embodiments, it was found that fed-batch culture mediums supplemented with zinc at concentrations up to at least about 12 μM provided for expression of an ADAMTS protein with increased specific activities (Table 20). Notably, in fed-batch cultures supplemented with zinc at a final concentration of 12 μM, specific cell growth rates and total activity were unaffected, while the specific activities of the expressed ADAMTS13 proteins continued to increase. This is in contrast to what was seen in experiments employing chemostatic cell-cultivation. In these experiments, supplementation of the culture medium with zinc at a final concentration of 5 μM resulted in an increase in the specific activity of the ADAMTS13 in the supernatant (Table 21). However, at higher levels of supplementation, 8.5 μM and 12 μM, specific cell growth rates and total ADAMTS13 protein yields were decreased, although the specific activity of ADAMTS13 in the culture supernatant remained high.

Accordingly, in one embodiment the methods of the invention comprise the use of fed-batch cell-cultivation with a medium comprising zinc at a concentration of at least at or about 2 μM, at least at or about 5 μM, at or about between 2 μM and 12 μM, at or about between 2 μM and 5 μM, at or about between 5 μM and 12 μM, or at least at or about 3 μM, 4 μM, 5 μM, 6 μM, 7 μM, 8 μM, 9 μM, 10 μM, 11 μM, 12 μM, 13 μM, 14 μM, 15 μM, 20 μM, 25 μM, 30 μM, or more zinc. In some embodiments, the zinc concentration may be from at least about 5 μM to at least about 12 μM. In certain embodiments, the medium may be an animal protein-free, oligopeptide-free, or chemically defined medium.

1. Continuous Culture

Advantageously, the present invention provides methods of expressing an ADAMTS protein, for example ADAMTS13, with high specific activity in a continuous culture. These methods allow for the continued expression and purification of an ADAMTS proteins from a single culture over extended periods of time. Specifically, it was found that high levels of ADAMTS13 protein expression and specific activity could be maintained for at least 53 days in a 10 L chemostat bioreactor, under the conditions provided by the present invention (Example 3, see, Table 15). In a preferred embodiment, the ADAMTS protein is ADAMTS13.

Accordingly, in one embodiment, the present invention provides methods of expressing an ADAMTS protein (e.g., ADAMTS13) with high specificity for an extended period of time. In certain embodiments, the culture is maintained for at least at or about 7 days, or at least at or about 14 days, 21 days, 28 days, or at least at or about 5 weeks, 6 weeks, 7 weeks, or at least at or about 2 months, or 3, 4, 5, 6, 7, 8, 9, 10, 11, 12, 13, 14, 15, 16, 17, 18 months or longer. In some of these embodiments, the level of total ADAMTS protein expression, activity, or specific activity is maintained in the culture for an extended period of time. In other embodiments, the specific growth rate, cell density, and the like is maintained in the culture for an extended period of time. In some embodiments, the culture medium may be supplemented with at least one of calcium, zinc, or nicotinamide (vitamin B3), for example, at a concentration according to any one of Var. 1 to Var. 149 (Table 2 to Table 9). In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In one embodiment, a continuous cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 7 days. In another embodiment, a continuous cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 14 days. In another embodiment, a continuous cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 21 days. In another embodiment, a continuous cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 1 month. In another embodiment, a continuous cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 2 months. In another embodiment, a continuous cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 3, 4, 5, 6, 7, 8, 9, 10, 11, 12, 13, 14, 15, 16, 17, 18, or more months. In a preferred embodiment, the ADAMTS protein is ADAMTS13.

In certain embodiments, the methods of ADAMTS protein (e.g., ADAMTS13) expression may comprise the use of continuous cell-cultivation with a medium comprising zinc at a concentration at of at least at or about 2 µM zinc, at least at or about 5 µM zinc, at or about between 2 µM and 12 µM zinc, at or about between 2 µM and 5 µM zinc, at or about between 3 µM and 5 µM zinc, at or about between 5 µM and 12 µM zinc, or at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc for at least 7 days. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under continuous culture conditions, a cell harboring a nucleic acid encoding an ADAMTS protein (e.g., ADAMTS13) in a culture medium containing at least at or about 2 µM zinc for at least 7 days. In other embodiments, the culture medium will contain at least about 3 µM zinc. In another embodiment, the culture medium will contain at least about 5 µM zinc. In another embodiment, the culture medium will contain at or about between 2 µM zinc and 5 µM zinc. In another embodiment, the culture medium will contain at or about between 3 µM zinc and 5 µM zinc. In another embodiment, the culture medium will contain at or about between 2 µM zinc and 12 µM zinc. In another embodiment, the culture medium will contain at or about between 3 µM zinc and 12 µM zinc. In another embodiment, the culture medium will contain at or about between 5 µM zinc and 12 µM zinc. In another embodiment, the culture medium will contain at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc. In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under continuous culture conditions, a cell harboring a nucleic acid encoding an ADAMTS protein (e.g., ADAMTS13) in a culture medium containing at least at or about 0.5 mM calcium for at least 7 days. In other embodiments, the culture medium will contain at least about 1.0 mM calcium. In another embodiment, the culture medium will contain at least about 1.5 mM calcium. In another embodiment, the culture medium will contain at or about between 0.5 mM and 1.5 mM calcium. In another embodiment, the culture medium will contain at or about between 1.0 mM and 1.5 mM calcium. In another embodiment, the culture medium will contain at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under continuous culture conditions, a cell harboring a nucleic acid encoding an ADAMTS protein (e.g., ADAMTS13) in a culture medium containing at least at or about 2 mg/L nicotinamide (vitamin B3) for at least 7 days. In other embodiments, the culture medium will contain at least about 5 mg/L nicotinamide (vitamin B3). In another embodiment, the culture medium will contain at least about 7 mg/L nicotinamide (vitamin B3). In another embodiment, the culture medium will contain at or about between 2 mg/L and 7 mg/L nicotinamide (vitamin B3). In another embodiment, the culture medium will contain at or about between 5 mg/L and 7 mg/L nicotinamide (vitamin B3). In another embodiment, the culture medium will contain at least at or about 3 mg/L, 4 mg/L, 5 mg/L, 6 mg/L, 7 mg/L, 8 mg/L, 9 mg/L, 10 mg/L, 15 mg/L, 20 mg/L, or more nicotinamide (vitamin B3). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under continuous culture conditions, a cell harboring a nucleic acid encoding an ADAMTS protein (e.g., ADAMTS13) in a culture medium supplemented with both zinc and calcium for at least 7 days. In certain embodiments, the zinc and calcium concentrations can be any of those described herein. In certain embodiments, the zinc and calcium concentrations will be one of Var. 94 to Var. 113 (Table 7). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under continuous culture conditions, a cell harboring a nucleic acid encoding an ADAMTS protein (e.g., ADAMTS13) in a culture medium supplemented with both zinc and nicotinamide (vitamin B3) for at least 7 days. In certain embodiments, the zinc and nicotinamide (vitamin B3) concentrations can be any of those described herein. In certain embodiments, the zinc and nicotinamide (vitamin B3) concentrations will be one of Var. 114 to Var. 133 (Table 8). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under continuous culture conditions, a cell harboring a nucleic acid encoding an ADAMTS protein (e.g., ADAMTS13) in a culture medium supplemented with both calcium and nicotinamide (vitamin B3) for at least 7 days. In certain embodiments, the calcium and nicotinamide (vitamin B3) concentrations can be any of those described herein. In certain embodiments, the calcium and nicotinamide (vitamin B3) concentrations will be one of Var. 134 to Var. 149 (Table 9). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under continuous culture conditions, a cell harboring a nucleic acid encoding an ADAMTS protein (e.g., ADAMTS13) in a culture medium supplemented with zinc, calcium, and nicotinamide (vitamin B3) for at least 7 days. In certain embodiments, the zinc, calcium, and nicotinamide (vitamin B3) concentrations can be any of those described herein. In certain embodiments, the zinc, calcium, and nicotinamide (vitamin B3) concentrations will be one of Var. 14 to Var. 93 (Table 3 to Table 6). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In one embodiment, the culture is maintained at a cell density of between about $0.5 \times 10^6$ and $4 \times 10^7$ cells/ml for an extended period of time. In other embodiments, the cell density is maintained at a concentration of between about $1.0 \times 10^6$ and about $1.0 \times 10^7$ cells/ml for an extended period of time. In other embodiments, the cell density is maintained at a concentration of between about $1.0 \times 10^6$ and about $4.0 \times 10^6$ cells/ml for an extended period of time. In other embodiments, the cell density is maintained at a concentration of between about $1.0 \times 10^6$ and about $4.0 \times 10^6$ cells/ml for an extended period of time. In yet other embodiments, the cell density may be maintained at a concentration between about $2.0 \times 10^6$ and about $4.0 \times 10^6$, or between about $1.0 \times 10^6$ and about $2.5 \times 10^6$, or between about $1.5 \times 10^6$ and about $3.5 \times 10^6$, or any other similar range, for an extended period of time. The cell density at which a cell-culture is maintained at for production of a recombinant ADAMTS protein (e.g., ADAMTS13) will depend upon the culture-conditions and medium used for protein expression. One of skill in the art will readily be able to determine the optimal cell density for a cell-culture producing an ADAMTS protein. In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In other embodiments, the methods of ADAMTS13 expression allow for the production of at least at or about 500 units of ADAMTS13 activity per liter culture per day (500 U/L/D), for example FRETS-VWF73 activity units, with a specific activity of at least at or about 500 U/mg A13. In another embodiments, the methods of ADAMTS13 expression allow for the production of at least at or about 600 U/L/D. In another embodiments, the methods of ADAMTS13 expression allow for the production of at least at or about 700 U/L/D. In another embodiments, the methods of ADAMTS13 expression allow for the production of at least at or about 800 U/L/D. In another embodiments, the methods of ADAMTS13 expression allow for the production of at least at or about 900 U/L/D. In another embodiments, the methods of ADAMTS13 expression allow for the production of at least at or about 1000 U/L/D. In another embodiments, the methods of ADAMTS13 expression allow for the production of at least at or about 1100 U/L/D. In another embodiments, the methods of ADAMTS13 expression allow for the production of at least at or about 1200 U/L/D. In another embodiments, the methods of ADAMTS13 expression allow for the production of at least at or about 1300 U/L/D. In another embodiments, the methods of ADAMTS13 expression allow for the production of at least at or about 1400 U/L/D. In another embodiments, the methods of ADAMTS13 expression allow for the production of at least at or about 1500 U/L/D. In yet another embodiments, the methods of ADAMTS13 expression allow for the production of at least at or about 2000 U/L/D. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

In another embodiment, the methods allow for the extended expression of ADAMTS13 protein with high specific activities, for example, a specific activity of at least about 600 U/mg A13 protein, or at least about 700, 800, 900, 1000, 1100, 1200, 1300, 1400, 1500, 1600, 1700, 1800, 1900, 2000, or more U/mg A13 protein for an extended period of time. In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one particular embodiment, the method comprises the use of chemostat cell-cultivation. In another embodiment, the method comprises the use of turbidostat cell-cultivation. In yet another embodiment, the method comprises the use of perfusion cell-cultivation. In certain embodiments, the medium may be an animal protein-free, oligopeptide-free, or chemically defined medium. In a preferred embodiment, the ADAMTS protein is ADAMTS13.

2. Batch Culture

In another aspect, the present invention provides methods of expressing an ADAMTS protein, for example ADAMTS13, with high specific activity in a batch culture. In some embodiments, the culture medium may be supplemented with at least one of calcium, zinc, or nicotinamide (vitamin B3), for example, at a concentration according to any one of Var. 1 to Var. 149 (Table 2 to Table 9). In one particular embodiment, the method comprises the use of single-batch cell-cultivation. In another embodiment, the method comprises the use of fed-batch cell-cultivation. In yet another embodiment, the method comprises the use of repeated batch cell-cultivation. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In one embodiment, a fed-batch or repeated-batch cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 7 days. In another embodiment, a fed-batch or repeated-batch cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 14 days. In another embodiment, a fed-batch or repeated-batch cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 21 days. In another embodiment, a fed-batch or repeated-batch cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 1 month. In another embodiment, a fed-batch or repeated-batch cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 2 months. In another embodiment, a fed-batch or repeated-batch cell cultivation technique may be used to express an ADAMTS protein (e.g., ADAMTS13) in a cell culture containing zinc, calcium, and/or nicotinamide (vitamin B3) at a concentration according to any one of Var. 1 to Var. 149 (Table 2 to Table 9) for at least 3, 4, 5, 6, 7, 8, 9, 10, 11, 12, 13, 14, 15, 16, 17, 18, or more months. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In certain embodiments, the methods of ADAMTS protein (e.g., ADAMTS13) expression may comprise the use of fed-batch or repeated-batch cell-cultivation with a medium comprising zinc at a concentration at of at least at or about 2 µM zinc, at least at or about 5 µM zinc, at or about between 2 µM and 12 µM zinc, at or about between 2 µM and 5 µM zinc, at or about between 3 µM and 5 µM zinc, at or about between 5 µM and 12 µM zinc, or at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc for at least 7 days. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under fed-batch or repeated-batch culture conditions, a cell harboring a nucleic acid encoding an ADAMTS protein (e.g., ADAMTS13) in a culture medium containing at least at or about 0.5 mM calcium for at least 7 days. In other embodiments, the culture medium will contain at least about 1.0 mM calcium. In another embodiment, the culture medium will contain at least about 1.5 mM calcium. In another embodiment, the culture medium will contain at or about between 0.5 mM and 1.5 mM calcium. In another embodiment, the culture medium will contain at or about between 1.0 mM and 1.5 mM calcium. In another embodiment, the culture medium will contain at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under fed-batch or repeated-batch culture conditions, a cell harboring a nucleic acid encoding an ADAMTS protein (e.g., ADAMTS13) in a culture medium containing at least at or about 2 mg/L nicotinamide (vitamin B3) for at least 7 days. In other embodiments, the culture medium will contain at least about 5 mg/L nicotinamide (vitamin B3). In another embodiment, the culture medium will contain at least about 7 mg/L nicotinamide (vitamin B3). In another embodiment, the culture medium will contain at or about between 2 mg/L and 7 mg/L nicotinamide (vitamin B3). In another embodiment, the culture medium will contain at or about between 5 mg/L and 7 mg/L nicotinamide (vitamin B3). In another embodiment, the culture medium will contain at least at or about 3 mg/L, 4 mg/L, 5 mg/L, 6 mg/L, 7 mg/L, 8 mg/L, 9 mg/L, 10 mg/L, 15 mg/L, 20 mg/L, or more nicotinamide (vitamin B3). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under fed-batch or repeated-batch culture conditions, a cell harboring a nucleic acid encoding an ADAMTS protein (e.g., ADAMTS13) in a culture medium supplemented with both zinc and calcium for at least 7 days. In certain embodiments, the zinc and calcium concentrations can be any of those described herein. In certain embodiments, the zinc and calcium concentrations will be one of Var. 94 to Var. 113 (Table 7). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under fed-batch or repeated-batch culture conditions, a cell harboring a nucleic acid encoding an ADAMTS protein (e.g., ADAMTS13) in a culture medium supplemented with both zinc and nicotinamide (vitamin B3) for at least 7 days. In certain embodiments, the zinc and nicotinamide (vitamin B3) concentrations can be any of those described herein. In certain embodiments, the zinc and nicotinamide (vitamin B3) concentrations will be one of Var. 114 to Var. 133 (Table 8). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under fed-batch or repeated-batch culture conditions, a cell harboring a nucleic acid encoding an ADAMTS protein (e.g., ADAMTS13) in a culture medium supplemented with both calcium and nicotinamide (vitamin B3) for at least 7 days. In certain embodiments, the calcium and nicotinamide (vitamin B3) concentrations can be any of those described herein. In certain embodiments, the calcium and nicotinamide (vitamin B3) concentrations will be one of Var. 134 to Var. 149 (Table 9). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In one embodiment, a method for the expressing an ADAMTS protein comprises culturing, under fed-batch or repeated-batch culture conditions, a cell harboring a nucleic acid encoding an ADAMTS protein (e.g., ADAMTS13) in a culture medium supplemented with zinc, calcium, and nicotinamide (vitamin B3) for at least 7 days. In certain embodiments, the zinc, calcium, and nicotinamide (vitamin B3) concentrations can be any of those described herein. In certain embodiments, the zinc, calcium, and nicotinamide (vitamin B3) concentrations will be one of Var. 14 to Var. 93 (Table 3 to Table 6). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In one embodiment, the culture is maintained at a cell density of between about $0.5 \times 10^6$ and $4 \times 10^7$ cells/ml for an extended period of time. In other embodiments, the cell density is maintained at a concentration of between about $1.0 \times 10^6$ and about $1.0 \times 10^7$ cells/ml for an extended period of time. In other embodiments, the cell density is maintained at a concentration of between about $1.0 \times 10^6$ and about $4.0 \times 10^6$ cells/ml for an extended period of time. In other embodiments, the cell density is maintained at a concentration of between about $1.0 \times 10^6$ and about $4.0 \times 10^6$ cells/ml for an extended period of time. In yet other embodiments, the cell density may be maintained at a concentration between about $2.0 \times 10^6$ and about $4.0 \times 10^6$, or between about $1.0 \times 10^6$ and about $2.5 \times 10^6$, or between about $1.5 \times 10^6$ and about $3.5 \times 10^6$, or any other similar range, for an extended period of time. The cell density at which a cell-culture is maintained at for production of a recombinant ADAMTS protein (e.g., ADAMTS13) will depend upon the culture-conditions and medium used for protein expression. One of skill in the art will readily be able to determine the optimal cell density for a cell-culture producing an ADAMTS protein. In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In other embodiments, the methods of ADAMTS13 expression allow for the production of at least at or about 500 units of ADAMTS13 activity per liter culture per day (500 U/L/D), for example FRETS-VWF73 activity units, with a specific activity of at least at or about 500 U/mg A13. In another embodiments, the methods of ADAMTS13 expression allow for the production of at least at or about 600 U/L/D. In another embodiments, the methods of ADAMTS13 expression allow for the production of at least at or about 700 U/L/D. In another embodiments, the methods of ADAMTS13 expression allow for the production of at least at or about 800 U/L/D. In another embodiments, the methods of ADAMTS13 expression allow for the production of at least at or about 900 U/L/D. In another embodiments, the methods of ADAMTS13 expression allow for the production of at least at or about 1000 U/L/D. In another embodiments, the methods of ADAMTS13 expression allow for the production of at least at or about 1100 U/L/D. In another embodiments, the methods of ADAMTS13 expression allow for the production of at least at or about 1200 U/L/D. In another embodiments, the methods of ADAMTS13 expression allow for the production of at least at or about 1300 U/L/D. In another embodiments, the methods of ADAMTS13 expression allow for the production of at least at or about 1400 U/L/D. In another embodiments, the methods of ADAMTS13 expression allow for the production of at least at or about 1500 U/L/D. In yet another embodiments, the methods of ADAMTS13 expression allow for the production of at least at or about 2000 U/L/D. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

In another embodiment, the methods allow for the extended expression of ADAMTS13 protein with high specific activities, for example, a specific activity of at least about 600 U/mg A13 protein, or at least about 700, 800, 900, 1000, 1100, 1200, 1300, 1400, 1500, 1600, 1700, 1800, 1900, 2000, or more U/mg A13 protein for an extended period of time. In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In some embodiments, the cultures may be performed as suspension batch cultures. In other embodiments, the cultures may be performed as adherent batch cultures. In certain embodiments, the medium may be an animal protein-free, oligopeptide-free, or chemically defined medium. In a preferred embodiment, the ADAMTS protein is ADAMTS13.

3. Culture Conditions

Figure 2A:
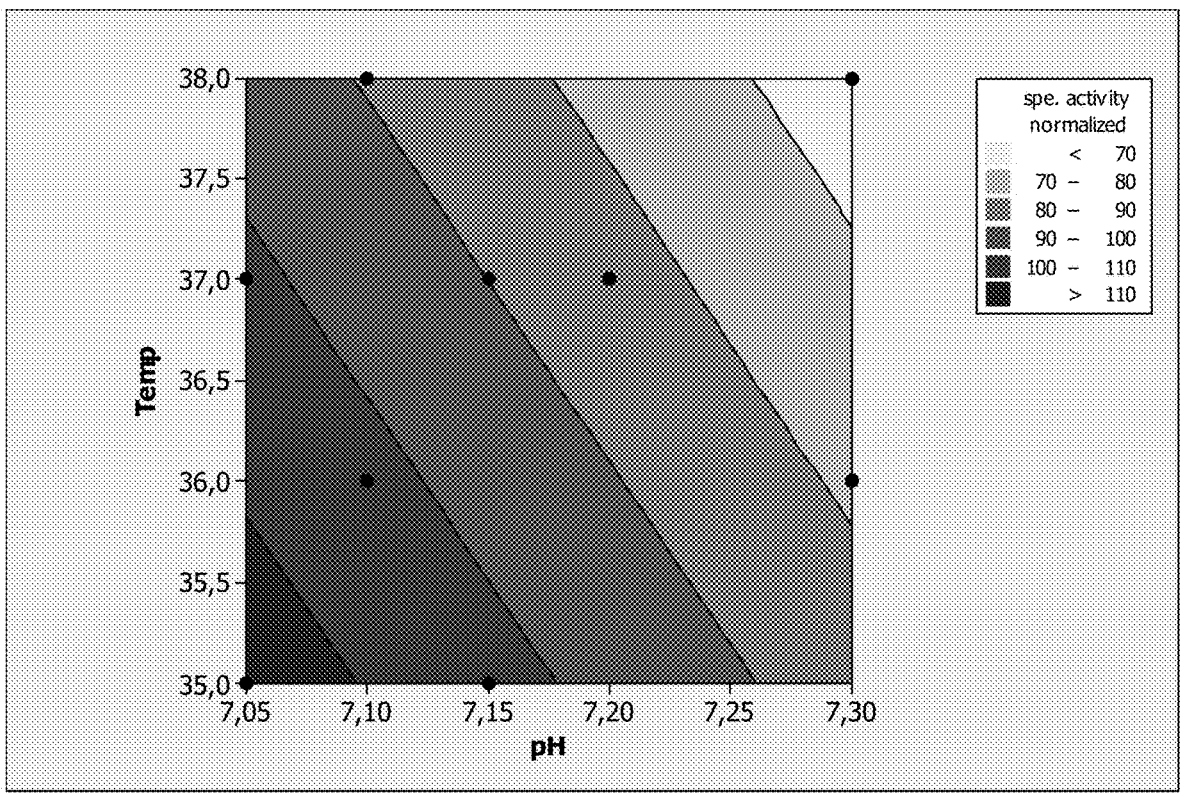
FIG. 2A and FIG. 2B. Specific activity levels (FRETS-VWF73/antigen by ELISA) of CHO cells expressing recombinant human ADAMTS13 cultured in animal protein-free medium under varying temperature and pH conditions. The results of the various cell-culture experiments are shown as (A) contour plot and (B) surface plot representations of specific activity as a function of culture temperature and pH.
Figure 2B:
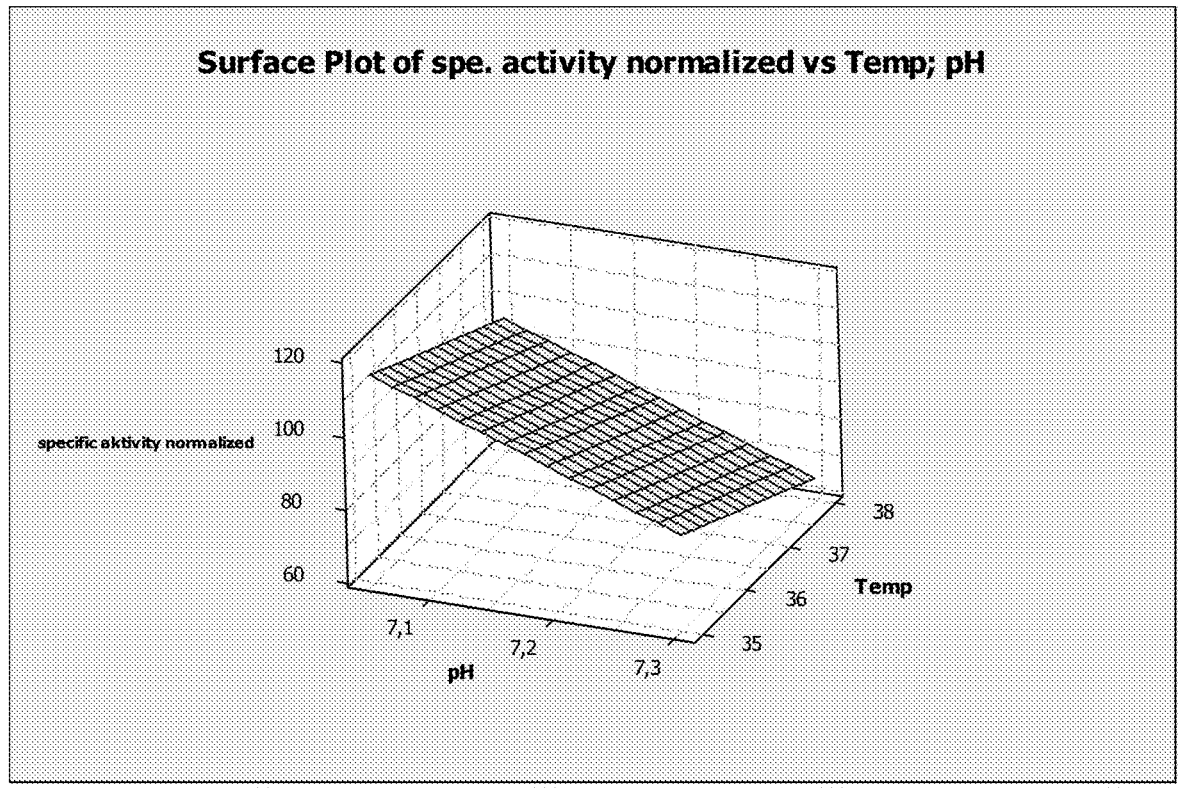

Surprisingly, it has also been found that cell viabilities and ADAMTS13 activities can be increased by small variations in the temperature and pH of the cell culture. As can be seen in FIG. 2, the specific activity of the expressed ADAMTS13 is greatly enhanced when cells harboring a nucleotide encoding an ADAMTS13 protein are cultured at a pH below about 7.30. Temperature, although to a lesser degree, is also a factor contributing to ADAMTS13 specific activity in these studies. Similarly, it was found that the volumetric productivity of A13 (measured by FRETS-VWF73) in the supernatants of cultures grown at a pH of between about 6.80 and about 7.3 was greatly increased as compared to pH levels above and below that range. ADAMTS13 productivity was also affected by the temperature of the culture. Maximum activity was found in cultures grown at temperature between about 34° C. and about 37° C.

In other embodiments, the methods of ADAMTS protein expression comprise a step of maintaining the temperature of the culture medium at a temperature of about 34° C. and about 37° C. In certain embodiments, the culture medium may be maintained at a temperature of 36.5° C. or less, 36.0° or less, 35.5° C. or less, or less than 35.0° C. In a specific embodiment, the temperature is maintained at a temperature of about 36° C. In a specific embodiment the culture is maintained at a combination of the temperature and pH ranges mentioned above, e.g. 36.5° C. or less and a pH of e.g. 7.15 or less. In a preferred embodiment the culture is maintained at a temperature of 36.0° C. and a pH of 7.10.

Accordingly, in some embodiments, the methods of ADAMTS protein expression comprise a step of maintaining the pH of the culture medium at a pH of between about 6.8 and 7.3. In certain embodiments, the pH may be between about 7.0 and about 7.25 or between about 7.05 and about 7.15. In certain embodiments the ph may be maintained at a pH of 7.20 or less, 7.15 or less, 7.10 or less or 7.05 or less. In one specific embodiment, the pH of the culture medium is maintained at a pH of about 7.1.

In one embodiment, the invention provides a method for the expressing an ADAMTS protein comprises culturing a cell harboring a nucleic acid encoding an ADAMTS protein (e.g., ADAMTS13) at a temperature at or about between 34° C. and about 37° C. at a pH of at or about between 6.8 and 7.3. In another embodiment, the temperature of the culture will be at or about between 35° C. and about 37° C. and the pH will be at or about between 6.8 and 7.3. In another embodiment, the temperature of the culture will be at or about between 35.5° C. and about 36.5° C. and the pH will be at or about between 6.8 and 7.3. In another embodiment, the temperature of the culture will be at or about 36° C. and the pH will be at or about between 6.8 and 7.3. In one embodiment, the culture medium will be supplemented with zinc. In another specific embodiment, the culture medium will be supplemented with calcium. In another specific embodiment, the culture medium will be supplemented with nicotinamide (vitamin B3). In one embodiment, the culture medium will be supplemented with zinc and calcium. In one embodiment, the zinc and calcium concentrations will be one of Var. 94 to Var. 113 (Table 7). In another embodiment, the culture medium will be supplemented with zinc and nicotinamide (vitamin B3). In one embodiment the zinc and nicotinamide (vitamin B3) concentrations will be one of Var.

114 to Var. 133 (Table 8). In another embodiment, the culture medium will be supplemented with calcium and nicotinamide (vitamin B3). In one embodiment, the calcium and nicotinamide (vitamin B3) concentrations will be one of Var. 134 to Var. 149 (Table 9). In yet another embodiment, the culture medium will be concentrated with zinc, calcium, and nicotinamide (vitamin B3). In one embodiment, the zinc, calcium, and nicotinamide (vitamin B3) concentrations will be one of Var. 14 to Var. 93 (Table 3 to Table 6).

In another embodiment, the invention provides a method for the expressing an ADAMTS protein comprises culturing a cell harboring a nucleic acid encoding an ADAMTS protein (e.g., ADAMTS13) at a temperature at or about between 34° C. and about 37° C. at a pH of at or about between 6.9 and 7.25. In another embodiment, the temperature of the culture will be at or about between 35° C. and about 37° C. and the pH will be at or about between 6.9 and 7.25. In another embodiment, the temperature of the culture will be at or about between 35.5° C. and about 36.5° C. and the pH will be at or about between 6.9 and 7.25. In another embodiment, the temperature of the culture will be at or about 36° C. and the pH will be at or about between 6.9 and 7.25. In one embodiment, the culture medium will be supplemented with zinc. In another specific embodiment, the culture medium will be supplemented with calcium. In another specific embodiment, the culture medium will be supplemented with nicotinamide (vitamin B3). In one embodiment, the culture medium will be supplemented with zinc and calcium. In one embodiment, the zinc and calcium concentrations will be one of Var. 94 to Var. 113 (Table 7). In another embodiment, the culture medium will be supplemented with zinc and nicotinamide (vitamin B3). In one embodiment the zinc and nicotinamide (vitamin B3) concentrations will be one of Var. 114 to Var. 133 (Table 8). In another embodiment, the culture medium will be supplemented with calcium and nicotinamide (vitamin B3). In one embodiment, the calcium and nicotinamide (vitamin B3) concentrations will be one of Var. 134 to Var. 149 (Table 9). In yet another embodiment, the culture medium will be concentrated with zinc, calcium, and nicotinamide (vitamin B3). In one embodiment, the zinc, calcium, and nicotinamide (vitamin B3) concentrations will be one of Var. 14 to Var. 93 (Table 3 to Table 6).

In another embodiment, the invention provides a method for the expressing an ADAMTS protein comprises culturing a cell harboring a nucleic acid encoding an ADAMTS protein (e.g., ADAMTS13) at a temperature at or about between 34° C. and about 37° C. at a pH of at or about between 7.0 and 7.20. In another embodiment, the temperature of the culture will be at or about between 35° C. and about 37° C. and the pH will be at or about between 7.0 and 7.20. In another embodiment, the temperature of the culture will be at or about between 35.5° C. and about 36.5° C. and the pH will be at or about between 7.0 and 7.20. In another embodiment, the temperature of the culture will be at or about 36° C. and the pH will be at or about between 7.0 and 7.20. In one embodiment, the culture medium will be supplemented with zinc. In another specific embodiment, the culture medium will be supplemented with calcium. In another specific embodiment, the culture medium will be supplemented with nicotinamide (vitamin B3). In one embodiment, the culture medium will be supplemented with zinc and calcium. In one embodiment, the zinc and calcium concentrations will be one of Var. 94 to Var. 113 (Table 7). In another embodiment, the culture medium will be supplemented with zinc and nicotinamide (vitamin B3). In one embodiment the zinc and nicotinamide (vitamin B3) concentrations will be one of Var. 114 to Var. 133 (Table 8). In another embodiment, the culture medium will be supplemented with calcium and nicotinamide (vitamin B3). In one embodiment, the calcium and nicotinamide (vitamin B3) concentrations will be one of Var. 134 to Var. 149 (Table 9). In yet another embodiment, the culture medium will be concentrated with zinc, calcium, and nicotinamide (vitamin B3). In one embodiment, the zinc, calcium, and nicotinamide (vitamin B3) concentrations will be one of Var. 14 to Var. 93 (Table 3 to Table 6).

The concept of cell-growth on microcarriers was first described by van Wezel (van Wezel A L., Nature 1967 Oct. 7; 216(5110):64-5) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing an ADAMTS protein can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal cell Biotechnology 3:283-303). Therefore, according to one embodiment of the invention cells expressing an ADAMTS protein are cultured on spherical microcarriers. According to another embodiment of the invention cells expressing an ADAMTS protein are cultured on porous microcarriers. It is also possible to grow the cells to a biomass on a spherical microcarriers and subculture the cells when they have reached final fermenter biomass and prior to production of the expressed protein on a porous microcarrier or vice versa. Spherical microcarrier are those selected from the group of smooth surface such as Cytodex™ 1, Cytodex™ 2, and Cytodex™ 3 (GE Healthcare) and macroporous microcarriers such as Cytopore™ 1, Cytopore™ 2, Cytoline™ 1, and Cytoline™ 2 (GE Healthcare).

IV. Culture Mediums

In one aspect, the present invention provides culture mediums that are useful for the expression of ADAMTS proteins having high specific activities. Advantageously, it has been found that by supplementing a culture medium with various components, such as combinations of zinc, calcium, and nicotinamide (vitamin B3), that the activities of ADAMTS (e.g., ADAMTS13) enzymes expressed in cells cultured in the medium are greatly enhanced, while the enzymes are expressed at levels as high, if not higher, that cells cultured in non-supplemented mediums.

Methods of preparing animal protein-free and chemically defined culture mediums are known in the art, for example in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes. In one embodiment, the culture medium used in the methods described herein is animal protein-free or oligopeptide-free medium. In certain embodiments, the culture medium may be chemically defined. In certain embodiments, the culture media may contain at least one polyamine at a concentration of about 0.5 mg/L to about 10 mg/L.

Accordingly, in one embodiment, culture medium is provided that is supplemented with additional calcium, zinc, and/or vitamin B3. In certain embodiments, the medium may be an animal protein-free, oligopeptide-free, or chemically defined medium. In certain embodiments, the animal protein-free or oligopeptide free medium is prepared as taught in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes, both of which are incorporated herein by reference in their entireties for all purposes, and supplemented with additional calcium, zinc, and/or vitamin B3. In a specific embodiment, the chemically defined culture medium may be similar to a Dulbecco's Modified Eagle's Media (DMEM), which has been supplemented with additional calcium, zinc, and/or vitamin B3, in order to increase the specific activity of an ADAMTS protein expressed in a cell cultured in the medium. In yet other embodiments, the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal.

In certain embodiments, the culture media contains at least one polyamine at a concentration of at or about between 0.5 mg/L and 30 mg/L. In another embodiment, the culture medium contains at least one polyamine at or about between 0.5 mg/L and 10 mg/L. In one embodiment, the culture medium contains at least one polyamine at or about between 2 mg/L and 8 mg/L. In certain embodiments the polyamine is from the group of ornithine, putrescine, spermine or spermidine, or the like. In a preferred embodiment, the polyamine is putrescine. In a specific embodiment, the culture medium contains at or about between 2 mg/L and 8 mg/L putrescine.

In one embodiment, a culture medium is provided for the expression of an ADAMTS protein (e.g., ADAMTS13) containing at least at or about 2 µM zinc. In another embodiment, the culture medium contains at least at or about 5 µM zinc. In one embodiment, the culture medium contains at or about between 2 µM and 12 µM zinc. In another embodiment, the culture medium contains at or about between 5 µM and 12 µM zinc. In yet other embodiments, the culture medium may contain at least at or about 2 µM, or at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc.

Generally, any zinc salt may be used to supplement the mediums of the invention, non-limiting examples of acceptable salts include, $ZnSO_4 \cdot 7H_2O$, $ZnSO_3 \cdot 2H_2O$, $(C_6H_5O_7)_2Zn_3 \cdot 2H_2O$, $ZnBr_2$, $ZnBr_2 \cdot 2H_2O$, $ZnCl_2$, $Zn(NO_3)_2 \cdot 6H_2O$, $Zn(H_2PO_4)_2 \cdot H_2O$, $(C_2H_3O_2)_2Zn \cdot 2H_2O$, and the like. In certain embodiments, a pharmaceutically acceptable salt of zinc is used to supplement the culture mediums of the invention. In other embodiments, a zinc containing peptide or protein preparation, for example insulin, may be used to the supplement the culture provided herein.

In another embodiment, a culture medium is provided for the expression of an ADAMTS protein (e.g., ADAMTS13) containing at least at or about 0.5 mM calcium. In another embodiment, the culture medium contains at least at or about 1.5 mM calcium. In one embodiment, the culture medium contains at or about between 0.5 mM and 1.5 mM calcium. In yet other embodiments, the culture medium may contain at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium.

Generally, any calcium salt may be used to supplement the mediums of the invention, non-limiting examples of acceptable salts include $CaC_{12}$, $CaC_{12}$, $CaFPO_3 \cdot 2H_2O$, $CaI_2$, $CaBr_2$, $(C_2H_3)O_2)_2Ca$, $(CHO_2)_2Ca$, $(C_6H_7O_6)_2Ca$, $(C_6H_5O_7)_2Ca_3 \cdot 2H_2O$, and the like. In certain embodiments, a pharmaceutically acceptable salt of calcium is used to supplement the culture mediums of the invention.

In another embodiment, a culture medium is provided for the expression of an ADAMTS protein (e.g., ADAMTS13) containing at least at or about 2 mg/L nicotinamide (vitamin B3). In another embodiment, the culture medium contains at least at or about 7 mg/L nicotinamide (vitamin B3). In one embodiment, the culture medium contains at or about between 2 mg/L and 10 mg/L nicotinamide (vitamin B3). In yet other embodiments, the culture medium may contain at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3).

Advantageously, it has been found that by supplementing a culture medium with both zinc and calcium, the specific activity of ADAMTS13 protein expressed in the culture medium is greatly increased. Accordingly, in one embodiment, the culture mediums provided herein for the expression of an ADAMTS protein (e.g., ADAMTS13) may be supplemented with both zinc and calcium. For example, a culture medium may be supplemented with zinc and calcium at levels provided in Table 7, i.e., at a level according to any one of Var. 94 to Var. 113.

TABLE 7

Exemplary embodiments of a culture mediums supplemented with both zinc and calcium, which are useful for the expression of an ADAMTS13 protein.

|  | At least 0.5 mM calcium | At least 1.5 mM calcium | Between 0.5 mM and 1.5 mM calcium | At least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium |
|---|---|---|---|---|
| At least 2 µM Zinc | Var. 94 | Var. 95 | Var. 96 | Var. 97 |
| At least 5 µM Zinc | Var. 98 | Var. 99 | Var. 100 | Var. 101 |

TABLE 7-continued

Exemplary embodiments of a culture mediums supplemented with both zinc and calcium, which are useful for the expression of an ADAMTS13 protein.

|  | At least 0.5 mM calcium | At least 1.5 mM calcium | Between 0.5 mM and 1.5 mM calcium | At least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium |
|---|---|---|---|---|
| Between 2 µM and 12 µM zinc | Var. 102 | Var. 103 | Var. 104 | Var. 105 |
| Between 5 µM and 12 µM zinc | Var. 106 | Var. 107 | Var. 108 | Var. 109 |
| At least 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc | Var. 110 | Var. 111 | Var. 112 | Var. 113 |

*Var. = Variation

Similarly, it has been found that by supplementing a culture medium with both zinc and nicotinamide (vitamin B3), the specific activity of ADAMTS13 protein expressed in the culture medium is synergistically increased. For example, this effect can be seen in Example 2 (compare Table 14 day 11 with Table 13 days 4 and 7). Accordingly, in one embodiment, the culture mediums provided herein for the expression of an ADAMTS protein (e.g., ADAMTS13) may be supplemented with both zinc and nicotinamide (vitamin B3). For example, a culture medium may be supplemented with zinc and nicotinamide (vitamin B3) at levels provided in Table 8, i.e., at a level according to any one of Var. 114 to Var. 133.

Advantageously, it has been found that by supplementing a culture medium with both nicotinamide and calcium, the specific activity of ADAMTS13 protein expressed in the culture medium is greatly increased. Accordingly, in one embodiment, the culture mediums provided herein for the expression of an ADAMTS protein (e.g., ADAMTS13) may be supplemented with both nicotinamide (vitamin B3) and calcium. For example, a culture medium may be supplemented with nicotinamide (vitamin B3) and calcium at levels provided in Table 9, i.e., at a level according to any one of Var. 134 to Var. 149.

TABLE 8

Exemplary embodiments of a culture mediums supplemented with both zinc and nicotinamide (vitamin B3), which are useful for the expression of an ADAMTS13 protein.

|  | At least 2 mg/L nicotinamide | At least 7 mg/L nicotinamide | Between 2 mg/L and 7 mg/L nicotinamide | At least 3 mg/L, 4 mg/L, 5 mg/L, 6 mg/L, 7 mg/L, 8 mg/L, 9 mg/L, 10 mg/L, 15 mg/L, 20 mg/L, or more nicotinamide |
|---|---|---|---|---|
| At least 2 µM Zinc | Var. 114 | Var. 115 | Var. 116 | Var. 117 |
| At least 5 µM Zinc | Var. 118 | Var. 119 | Var. 120 | Var. 121 |
| Between 2 µM and 12 µM zinc | Var. 122 | Var. 123 | Var. 124 | Var. 125 |
| Between 5 µM and 12 µM zinc | Var. 126 | Var. 127 | Var. 128 | Var. 129 |
| At least 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc | Var. 130 | Var. 131 | Var. 132 | Var. 133 |

Var. = Variation

TABLE 9

Exemplary embodiments of a culture mediums supplemented with both nicotinamide (vitamin B3) and calcium, which are useful for the expression of an ADAMTS13 protein.

| | At least 2 mg/L nicotinamide | At least 7 mg/L nicotinamide | Between 2 mg/L and 7 mg/L nicotinamide | At least 3 mg/L, 4 mg/L, 5 mg/L, 6 mg/L, 7 mg/L, 8 mg/L, 9 mg/L, 10 mg/L, 15 mg/L, 20 mg/L, or more nicotinamide |
|---|---|---|---|---|
| At least 0.5 mM calcium | Var. 134 | Var. 135 | Var. 136 | Var. 137 |
| At least 1.5 mM calcium | Var. 138 | Var. 139 | Var. 140 | Var. 141 |
| Between 0.5 mM and 1.5 mM calcium | Var. 142 | Var. 143 | Var. 144 | Var. 145 |
| At least 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium | Var. 146 | Var. 147 | Var. 148 | Var. 149 |

Var. = Variation

In some embodiments, the culture medium provided by the invention may be provided in a liquid or a dry or powder form. The medium may be pre-aliquoted in an amount suitable for single use or provided in a larger quantity that may be used for more than one cell-culture. Generally, the medium of the invention will be provided in a sterile fashion. Accordingly, the present invention also provides kits for the expression or production of an ADAMTS13 protein, the kits comprising a culture medium suitable for the expression of an ADAMTS protein having high specific activity.

In one aspect, the present invention provides culture mediums useful for the expression of ADAMTS protein (e.g., ADAMTS13) with high specific activities. In one embodiment, the culture medium contains at least about 2 µM zinc. In another embodiment, the culture medium contains between about 2 µM to about 12 µM zinc. In yet another embodiment, the culture medium contains at least about 5 µM zinc. In one embodiment, the culture medium contains between about 5 µM to about 12 µM zinc. In another embodiment, the culture medium contains at least about 0.5 mM calcium. In yet another embodiment, the culture medium contains between about 0.5 mM and about 1.5 mM calcium. In one embodiment, the culture medium contains at least about 2 µM zinc and at least about 0.5 mM calcium.

In yet other embodiments, it has been found that the addition of nicotinamide (vitamin B3) further enhances the expression and specific activity of ADAMTS proteins in cell culture. In one embodiment, the culture medium further comprises at least about 2 mg/L nicotinamide (vitamin B3). In another embodiment, the culture medium further comprises at least about 7 mg/L nicotinamide (vitamin B3). In yet another embodiment, the culture medium contains between about 2 mg/L and about 10 mg/L nicotinamide (vitamin B3).

In certain embodiments, the culture medium is an animal protein free culture medium. In another embodiment, the culture medium is a chemically defined medium. In certain embodiments, the culture medium may comprise one or more polyamines. In a particular embodiment, the polyamine is putrescine, for example, at a concentration of at least 0.5 mg/L. In a specific embodiment, the culture medium contains between about 2 mg/L and about 8 mg/L putrescine.

1. Protein Free Culture Mediums

In certain aspects, the present invention provides culture mediums for the expression of an ADAMTS protein (e.g., ADAMTS13), which are free of exogenously added protein. "Protein free culture medium" and related terms refers to culture medium lacking protein that is from a source exogenous to or other than the cells in the culture, which naturally shed proteins during growth. In one embodiment, a culture medium is provided for the expression of an ADAMTS protein (e.g., ADAMTS13), which is free of exogenously added protein (i.e., protein-free) and is supplemented with zinc, calcium, and/or nicotinamide (vitamin B3). In certain embodiments, the protein free culture medium contains a polyamine. For example, at a concentration of at least 2 mg/L, or at or about between 2 mg/L and 30 mg/L, or at or about between 2 mg/L and 8 mg/L. In a specific embodiment, the polyamine is putrescine. Exemplary protein free culture mediums are taught in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

In one embodiment, a protein-free culture medium is provided for the expression of an ADAMTS protein (e.g., ADAMTS13) contains at least at or about 2 µM zinc, at least at or about 5 µM zinc, at or about between 2 µM and 12 µM zinc, or at or about between 5 µM and 12 µM zinc. In yet other embodiments, a protein-free culture medium is provided for the expression of an ADAMTS protein (e.g., ADAMTS13) containing at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc.

In another embodiment, a protein-free culture medium is provided for the expression of an ADAMTS protein (e.g., ADAMTS13) contains at least at or about 0.5 mM calcium, at least at or about 1.5 mM calcium, or at or about between 0.5 and 1.5 mM calcium. In yet other embodiments, a protein-free culture medium is provided for the expression of an ADAMTS protein (e.g., ADAMTS13) containing at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium.

In yet another embodiment, a protein-free culture medium is provided for the expression of an ADAMTS protein (e.g., ADAMTS13) contains at least at or about 2 mg/L nicotinamide (vitamin B3), at least at or about 7 mg/L nicotinamide (vitamin B3), or at or about between 2 mg/L nicotinamide (vitamin B3). In yet other embodiments, a protein-free culture medium is provided for the expression of an ADAMTS protein (e.g., ADAMTS13) containing at least at or about 3 mg/L, 4 mg/L, 5 mg/L, 6 mg/L, 7 mg/L, 8 mg/L, 9 mg/L, 10 mg/L, 15 mg/L, 20 mg/L, or more nicotinamide (vitamin B3).

2. Oligopeptide Free Culture Mediums

In certain aspects, the present invention provides culture mediums for the expression of an ADAMTS protein (e.g., ADAMTS13), which are free of exogenously added oligopeptides. In one embodiment, a culture medium is provided for the expression of an ADAMTS protein (e.g., ADAMTS13), which is free of exogenously added oligopeptides (i.e., polypeptide-free) and is supplemented with zinc, calcium, and/or nicotinamide (vitamin B3). In certain embodiments, the oligopeptide free culture medium contains a polyamine. For example, at a concentration of at least 2 mg/L, or at or about between 2 mg/L and 30 mg/L, or at or about between 2 mg/L and 8 mg/L. In a specific embodiment, the polyamine is putrescine. Exemplary oligopeptide free culture mediums are taught in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

In one embodiment, an oligopeptide free culture medium is provided for the expression of an ADAMTS protein (e.g., ADAMTS13) contains at least at or about 2 µM zinc, at least at or about 5 µM zinc, at or about between 2 µM and 12 µM zinc, or at or about between 5 µM and 12 µM zinc. In yet other embodiments, an oligopeptide free culture medium is provided for the expression of an ADAMTS protein (e.g., ADAMTS13) containing at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc.

In another embodiment, an oligopeptide free culture medium is provided for the expression of an ADAMTS protein (e.g., ADAMTS13) contains at least at or about 0.5 mM calcium, at least at or about 1.5 mM calcium, or at or about between 0.5 and 1.5 mM calcium. In yet other embodiments, an oligopeptide free culture medium is provided for the expression of an ADAMTS protein (e.g., ADAMTS13) containing at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium.

In yet another embodiment, an oligopeptide free culture medium is provided for the expression of an ADAMTS protein (e.g., ADAMTS13) contains at least at or about 2 mg/L nicotinamide (vitamin B3), at least at or about 7 mg/L nicotinamide (vitamin B3), or at or about between 2 mg/L nicotinamide (vitamin B3). In yet other embodiments, an oligopeptide free culture medium is provided for the expression of an ADAMTS protein (e.g., ADAMTS13) containing at least at or about 3 mg/L, 4 mg/L, 5 mg/L, 6 mg/L, 7 mg/L, 8 mg/L, 9 mg/L, 10 mg/L, 15 mg/L, 20 mg/L, or more nicotinamide (vitamin B3).

3. Serum Free Culture Mediums

In certain aspects, the present invention provides culture mediums for the expression of an ADAMTS protein (e.g., ADAMTS13), which are free of serum. In one embodiment, a culture medium is provided for the expression of an ADAMTS protein (e.g., ADAMTS13), which is free of exogenously added serum (i.e., serum-free) and is supplemented with zinc, calcium, and/or nicotinamide (vitamin B3). In certain embodiments, the serum-free culture medium contains a polyamine. For example, at a concentration of at least 2 mg/L, or at or about between 2 mg/L and 30 mg/L, or at or about between 2 mg/L and 8 mg/L. In a specific embodiment, the polyamine is putrescine. Exemplary serum-free culture mediums are taught in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

In one embodiment, a serum-free culture medium is provided for the expression of an ADAMTS protein (e.g., ADAMTS13) contains at least at or about 2 µM zinc, at least at or about 5 µM zinc, at or about between 2 µM and 12 µM zinc, or at or about between 5 µM and 12 µM zinc. In yet other embodiments, a serum-free culture medium is provided for the expression of an ADAMTS protein (e.g., ADAMTS13) containing at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc.

In another embodiment, a serum-free culture medium is provided for the expression of an ADAMTS protein (e.g., ADAMTS13) contains at least at or about 0.5 mM calcium, at least at or about 1.5 mM calcium, or at or about between 0.5 and 1.5 mM calcium. In yet other embodiments, a serum-free culture medium is provided for the expression of an ADAMTS protein (e.g., ADAMTS13) containing at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium.

In yet another embodiment, a serum-free culture medium is provided for the expression of an ADAMTS protein (e.g., ADAMTS13) contains at least at or about 2 mg/L nicotinamide (vitamin B3), at least at or about 7 mg/L nicotinamide (vitamin B3), or at or about between 2 mg/L nicotinamide (vitamin B3). In yet other embodiments, a serum-free culture medium is provided for the expression of an ADAMTS protein (e.g., ADAMTS13) containing at least at or about 3 mg/L, 4 mg/L, 5 mg/L, 6 mg/L, 7 mg/L, 8 mg/L, 9 mg/L, 10 mg/L, 15 mg/L, 20 mg/L, or more nicotinamide (vitamin B3).

4. Animal Protein Free Culture Mediums

In certain aspects, the present invention provides culture mediums for the expression of an ADAMTS protein (e.g., ADAMTS13), which are free of animal proteins. In one embodiment, a culture medium is provided for the expression of an ADAMTS protein (e.g., ADAMTS13), which is free of exogenously added animal proteins or polypeptides (i.e., animal protein free) and is supplemented with zinc, calcium, and/or nicotinamide (vitamin B3). In certain embodiments, the animal protein free culture medium contains a polyamine. For example, at a concentration of at least 2 mg/L, or at or about between 2 mg/L and 30 mg/L, or at or about between 2 mg/L and 8 mg/L. In a specific embodiment, the polyamine is putrescine. Exemplary animal protein free culture mediums are taught in U.S. Pat. Nos. 6,171,825 and 6,936,441, WO 2007/077217, and U.S. Patent Application Publication Numbers 2008/0009040 and 2007/0212770, the disclosures of which are incorporated herein by reference in their entireties for all purposes.

In one embodiment, an animal protein free culture medium is provided for the expression of an ADAMTS protein (e.g., ADAMTS13) contains at least at or about 2 µM zinc, at least at or about 5 µM zinc, at or about between 2 µM and 12 µM zinc, or at or about between 5 µM and 12 µM zinc. In yet other embodiments, an animal protein free culture medium is provided for the expression of an ADAMTS protein (e.g., ADAMTS13) containing at least at or about 3 µM, 4 µM, 5 µM, 6 µM, 7 µM, 8 µM, 9 µM, 10 µM, 11 µM, 12 µM, 13 µM, 14 µM, 15 µM, 20 µM, 25 µM, 30 µM, or more zinc.

In another embodiment, an animal protein free culture medium is provided for the expression of an ADAMTS protein (e.g., ADAMTS13) contains at least at or about 0.5 mM calcium, at least at or about 1.5 mM calcium, or at or about between 0.5 and 1.5 mM calcium. In yet other embodiments, an animal protein free culture medium is provided for the expression of an ADAMTS protein (e.g., ADAMTS13) containing at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium.

In yet another embodiment, an animal protein free culture medium is provided for the expression of an ADAMTS protein (e.g., ADAMTS13) contains at least at or about 2 mg/L nicotinamide (vitamin B3), at least at or about 7 mg/L nicotinamide (vitamin B3), or at or about between 2 mg/L nicotinamide (vitamin B3). In yet other embodiments, an animal protein free culture medium is provided for the expression of an ADAMTS protein (e.g., ADAMTS13) containing at least at or about 3 mg/L, 4 mg/L, 5 mg/L, 6 mg/L, 7 mg/L, 8 mg/L, 9 mg/L, 10 mg/L, 15 mg/L, 20 mg/L, or more nicotinamide (vitamin B3).

V. ADAMTS Protein Purification

ADAMTS13 is secreted into the plasma in vivo, where it functions to regulate clotting activity by cleaving large multimers of vWF. The ability of mammalian cells to secrete ADAMTS13 after expression can be exploited during the production and purification of ADAMTS13 compositions in cell culture. For example, by expressing recombinant ADAMTS13 in mammalian cell culture, ADAMTS13 compositions can readily be recovered directly from the culture supernatant without the need to harvest and lyse cells. This permits the use of techniques such as continuous cell culture (e.g., perfusion or chemostatic cell culture) to produce large amounts of the protein without multiple culture lag and recovery periods. In one aspect of the invention, methods are provided for the purification of ADAMTS proteins having high specific activity from cell culture.

Accordingly, in one embodiment, ADAMTS13 proteins are expressed in culture and recovered directly from the culture supernatant. In this fashion, ADAMTS13 proteins are recovered by removing a fraction of the culture and purifying ADAMTS13 away from the other components of the supernatant. Generally, this involves separating any cells that are recovered along with the supernatant by filtration or centrifugation and subjecting the supernatant to one or more ADAMTS13 purification steps.

U.S. Patent Application Publication Number 2005/0266528 and Zheng et al., (2001, Blood, 98:1662-1666), the disclosures of which are herein incorporated by reference in their entireties for all purposes) provide exemplary methods for purifying ADAMTS13. Purified ADAMTS13 may be formulated according to conventional methods and used therapeutically, for example, to treat TTP.

In one aspect, the present invention provides methods for producing an ADAMTS protein composition (e.g., an ADAMTS13 composition). In a first embodiment, the method comprises the steps of: (a) culturing a cell harboring a nucleic acid encoding an ADAMTS protein in an animal protein-free culture medium; (b) removing a fraction of the supernatant from the culture; (c) performing a filtration or centrifugation step to remove any residual cells; (d) performing an ultrafiltration step to concentrate the ADAMTS protein; and (e) performing a diafiltration step with a buffer comprising at least about 0.5 µM zinc and at least about 0.1 mM calcium; thereby preparing an ADAMTS composition.

In certain embodiments, the step of culturing a cell comprises batch cell cultivation. In other embodiments, the step of culturing a cell comprises continuous cell cultivation.

In certain embodiments, the culture medium contains calcium. In a specific embodiment, the culture medium contains at least 0.5 mM calcium. In other embodiments, the culture medium contains zinc. In a specific embodiment, the culture medium contains at least 2 µM zinc. In yet other embodiments, the culture medium contains nicotinamide (vitamin B3). In a specific embodiment, the culture medium contains at least 2 mg/L nicotinamide (vitamin B3). In certain embodiments, the diafiltration buffer contains at least about 5 µM zinc and at least 2 mM calcium.

In certain embodiments, less than about 20% of the ADAMTS13 specific activity is lost between the end of step (c) and the end of step (e). In other embodiments, less than about 10% of the ADAMTS13 specific activity is lost between the end of step (c) and the end of step (e). In yet other embodiments, the ADAMTS13 composition has a specific activity of at least about 1000 U/mg. In another embodiment, the ADAMTS13 composition has a specific activity of at least about 1500 U/mg.

A. Buffer Exchange

Typically, when purifying a secreted protein from a culture supernatant, the first step of the purification process involves exchanging the culture medium for a buffered solution, which facilitates further purification of the protein of interest. Several options exist for exchanging the culture medium for a buffer, including without limitation, diafiltration, dialysis, buffer exchange techniques, gel filtration, chromatography, and the like.

It was found that ADAMTS13 protein compositions lost a significant fraction of their specific activity during such purification steps that require the introduction of new buffers, e.g., diafiltration, dialysis, buffer exchange, chromatography, and similar steps, regardless of the length of time between harvesting the supernatant from the culture and the purification step. Advantageously, however, the present inventors have discovered that by including zinc and calcium in the buffer being introduced into the system, such as in diafiltration, dialysis, buffer exchange, gel filtration, and chromatographic steps, that the high specific activities of the ADAMTS13 composition is retained. As evidence of this, Example 6 demonstrates that diafiltration of an ADAMTS13 composition with a buffer lacking calcium and zinc results in an average loss of almost 25% of the specific activity of the composition, while inclusion of calcium and zinc almost entirely prevent this loss (Table 22). Accordingly, the present invention provides methods for reducing the loss of activity for an ADAMTS protein compositions after diafiltration, or similar methods, e.g., dialysis, buffer exchange, chromatography, by the inclusion of zinc and calcium into the buffer system.

In one embodiment, a method is provided for purifying an ADAMTS protein (e.g., ADAMTS13) composition, the method comprising the steps of (a) culturing a cell harboring a nucleic acid encoding an ADAMTS protein (e.g., ADAMTS13) in a culture medium; (b) recovering a portion of the culture medium supernatant containing an ADAMTS protein (e.g., ADAMTS13); and (c) exchanging the culture medium supernatant with a buffered solution containing zinc and calcium, thereby preparing an ADAMTS protein (e.g., ADAMTS13) composition. In one embodiment, the culture medium contains zinc, calcium, and optionally nicotinamide (vitamin B3). In a preferred embodiment, the step of culturing a cell comprises a continuous culture (e.g., perfusion or chemostatic culture). In another preferred embodiment, the culture is maintained at a temperature between 34° C. and 37° C. In yet another preferred embodiment, the culture is maintained at a pH between 6.9 and 7.2.

In one specific embodiment, the step of exchanging the culture medium supernatant with a buffered solution comprises the use of a buffer containing at least at or about 0.5 mM calcium and at least at or about 0.5 µM zinc. In another embodiment, the buffer contains at least at or about 2 mM calcium and at least at or about 5 µM zinc. In certain embodiments, the concentration of calcium may be at least about 0.1 mM, 0.3 mM, 0.5 mM, 0.75 mM, 1 mM, 1.5 mM, 2 mM, 3 mM, 5 mM or more calcium. In certain embodiments, the concentration of zinc may be at least about 0.5 µM, 1 µM, 2 µM, 3 µM, 5 µM, 10 µM or more zinc. Generally, any combination of the concentrations above is suitable for use in the present methods.

In one embodiment, a method is provided for the buffer exchange of an ADAMTS protein composition (e.g., ADAMTS13) by performing the buffer exchange (e.g., diafiltration, dialysis, gel filtration, etc.) with a buffer containing calcium and zinc. In one specific embodiment, the method comprises the use of a buffer containing at least at or about 0.5 mM calcium and at least at or about 0.5 µM zinc. In another embodiment, the buffer contains at least at or about 1 mM calcium and at least at or about 1 µM zinc. In one embodiment, the buffer contains at least at or about 2 mM calcium and at least at or about 2 µM zinc. In another embodiment, the buffer contains at least at or about 2 mM calcium and at least at or about 5 µM zinc. In yet other embodiments, the buffer contains between 0.5 mM and 5 mM calcium and between 0.5 µM and 5 µM zinc. In certain embodiments, the concentration of calcium may be at least about 0.1 mM, 0.3 mM, 0.5 mM, 0.75 mM, 1 mM, 1.5 mM, 2 mM, 3 mM, 5 mM or more calcium. In certain embodiments, the concentration of zinc may be at least about 0.5 µM, 1 µM, 2 µM, 3 µM, 5 µM, 10 µM or more zinc. In a certain embodiment the harvest, cell free supernatant or the diafiltration buffer contains combinations of calcium and zinc in the above mentioned concentrations.

In another embodiment, a method is provided for stabilizing the enzymatic activity of an ADAMTS protein (e.g., ADAMTS13) after expression in cell culture comprising supplementing the cell containing harvest, the cell free supernatant or a diafiltration buffer used to concentrate or for exchange of buffer of an ADAMTS solution with calcium and zinc. In one specific embodiment, the method comprises the use of a buffer containing at least at or about 0.5 mM calcium and at least at or about 0.5 µM zinc. In another embodiment, the buffer contains at least at or about 2 mM calcium and at least at or about 5 µM zinc. In certain embodiments, the concentration of calcium may be at least about 0.1 mM, 0.3 mM, 0.5 mM, 0.75 mM, 1 mM, 1.5 mM, 2 mM, 3 mM, 5 mM or more calcium. In certain embodiments, the concentration of zinc may be at least about 0.5 µM, 1 µM, 2 µM, 3 µM, 5 µM, 10 µM or more zinc. In a certain embodiment the harvest, cell free supernatant or the diafiltration buffer contains combinations of calcium and zinc in the above mentioned concentrations.

In other embodiments, the methods provided herein result in a loss of less than 15% of the specific activity present during any individual step. In a preferred embodiment, the methods provided herein result in a loss of less than 10% of the specific activity after present during any individual step. In a particular embodiment, less than 15% of the specific activity present in the recovered culture supernatant is lost during an initial buffer exchange step (e.g., diafiltration or dialysis). In a preferred embodiment, less than 10% of the specific activity present in the recovered culture supernatant is lost during an initial buffer exchange step (e.g., diafiltration or dialysis).

B. Chromatography

In certain embodiments, the ADAMTS protein (e.g., ADAMTS13) composition is further enriched by one or more chromatographic steps. In one embodiment, a method is provided for providing an enriched ADAMTS protein (e.g., ADAMTS13) composition, the method comprising the steps of (a) culturing a cell harboring a nucleic acid encoding an ADAMTS protein (e.g., ADAMTS13) in a culture medium; (b) recovering a portion of the culture medium supernatant containing an ADAMTS protein (e.g., ADAMTS13); (c) exchanging the culture medium supernatant with a buffered solution containing zinc and calcium, to form a first ADAMTS protein (e.g., ADAMTS13) composition; and (d) further enriching the ADAMTS protein (e.g., ADAMTS13) with a chromatographic step, thereby providing an enriched ADAMTS (e.g., ADAMTS13) composition. In one embodiment, the culture medium contains zinc, calcium, and optionally nicotinamide (vitamin B3). In a preferred embodiment, the step of culturing a cell comprises a continuous culture (e.g., perfusion or chemostatic culture). In another preferred embodiment, the culture is maintained at a temperature between 34° C. and 37° C. In yet another preferred embodiment, the culture is maintained at a pH between 6.9 and 7.2.

In one specific embodiment, the step of exchanging the culture medium supernatant with a buffered solution and/or the chromatographic step comprises the use of a buffer containing at least at or about 0.5 mM calcium and at least at or about 0.5 µM zinc. In a preferred embodiment, both steps comprise the use of buffers containing at least at or about 0.5 mM calcium and at least at or about 0.5 µM zinc. In another embodiment, the buffer contains at least at or about 2 mM calcium and at least at or about 5 µM zinc. In certain embodiments, the concentration of calcium may be at least about 0.1 mM, 0.3 mM, 0.5 mM, 0.75 mM, 1 mM, 1.5 mM, 2 mM, 3 mM, 5 mM or more calcium. In certain embodiments, the concentration of zinc may be at least about 0.5 µM, 1 µM, 2 µM, 3 µM, 5 µM, 10 µM or more zinc. Generally, any combination of the concentrations above is suitable for use in the present methods.

In one embodiment, a method is provided for maintaining the specific activity of an ADAMTS protein (e.g., ADAMTS13) composition during a chromatographic step by supplementing the buffer(s) used in the chromatographic step with zinc and calcium. In one specific embodiment, the method comprises the use of a buffer containing at least at or about 0.5 mM calcium and at least at or about 0.5 µM zinc. In another embodiment, the buffer contains at least at or about 2 mM calcium and at least at or about 5 µM zinc. In certain embodiments, the concentration of calcium may be at least about 0.1 mM, 0.3 mM, 0.5 mM, 0.75 mM, 1 mM, 1.5 mM, 2 mM, 3 mM, 5 mM or more calcium. In certain embodiments, the concentration of zinc may be at least about 0.5 µM, 1 µM, 2 µM, 3 µM, 5 µM, 10 µM or more zinc. Generally, any combination of the concentrations above is suitable for use in the present methods.

Non-limiting examples of chromatographic techniques that may be used to purify an ADAMTS protein composition (e.g., an ADAMTS13 composition) include anion exchange chromatography (AEC), cation exchange chromatography (CEC), hydrophobic exchange chromatography (HIC), hydroxyapatite chromatography (HAP), immuno-affinity chromatography, size exclusion chromatography (i.e., gel filtration), or other suitable chromatographic step. Chromatographic steps may be performed in either batch or column mode. In certain embodiments, buffers used to perform any of these chromatographic techniques will include zinc and calcium. In one specific embodiment, the method comprises the use of a buffer containing at least at or about 0.5 mM calcium and at least at or about 0.5 µM zinc. In another embodiment, the buffer contains at least at or about 2 mM calcium and at least at or about 5 µM zinc. In certain embodiments, the concentration of calcium may be at least about 0.1 mM, 0.3 mM, 0.5 mM, 0.75 mM, 1 mM, 1.5 mM, 2 mM, 3 mM, 5 mM or more calcium. In certain embodiments, the concentration of zinc may be at least about 0.5 µM, 1 µM, 2 µM, 3 µM, 5 µM, 10 µM or more zinc. Generally, any combination of the concentrations above is suitable for use in the present methods.

Any suitable anion exchange resin may be used in the methods provided herein. Non-limiting examples of anion exchange resins suitable for use include, diethylaminoethyl (DEAE), quaternary aminoethyl (QAE), and quaternary ammonium (Q) resins.

Any suitable cation exchange resin may be used in the methods provided herein. Non-limiting examples of cation exchange resins suitable for use include, carboxymethyl (CM), sulfopropyl (SP), methyl sulfonate (S) resins.

Any suitable hydroxyapatite or other calcium-based resin may be used in the methods provided herein. Non-limiting examples of suitable resins include hydroxyapatite resins, fluorapatite resins, fluorhydroxyapatite resins, and the like.

Any suitable hydrophobic interaction chromatography resin may be used in the methods provided herein. Non-limiting examples of suitable resins include phenyl-resins, methyl-resins, butyl-resins, octyl-resins, and the like.

In certain embodiments, an ADAMTS13 protein (e.g., ADAMTS13) may be further enriched by immuno-affinity chromatography, for example with resins conjugated to an antibody, aptamer, or other binding molecule highly specific for the ADAMTS13 protein (e.g., ADAMTS13).

In one embodiment, the method of reducing the loss of ADAMTS activity results in a net loss of less than 20% during any individual step, including but not-limited to, buffer exchange, diafiltration, dialysis, gel filtration, ion exchange chromatography, affinity chromatography, nanofiltration, ultrafiltration, sterile filtration, and the like. In other embodiments, the methods provided herein result in a loss of less than 15% of the specific activity present during any individual step. In a preferred embodiment, the methods provided herein result in a loss of less than 10% of the specific activity after present during any individual step. In a particular embodiment, less than 15% of the specific activity present in the recovered culture supernatant is lost during an initial buffer exchange step (e.g., diafiltration or dialysis). In a preferred embodiment, less than 10% of the specific activity present in the recovered culture supernatant is lost during an initial buffer exchange step (e.g., diafiltration or dialysis).

C. Virus Inactivation and/or Removal

In certain embodiments, the methods provided herein for the preparation of an ADAMTS (e.g., ADAMTS13) composition will further include at least one viral inactivation or removal steps. In certain embodiments, the methods provided herein will include at least two or at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3): S21-S28 and Kreil et al., *Transfusion* 2003 (43):1023-1028, the disclosures of which are expressly incorporated by reference herein in their entireties for all purposes), nanofiltration (Hamamoto et al., *Vox Sang* 1989 (56)230-236 and Yuasa et al., *J Gen Virol.* 1991 (72 (pt 8)):2021-2024, the disclosures of which are expressly incorporated by reference herein in their entireties for all purposes). In a preferred embodiment, the present invention provides methods for the preparation of an ADAMTS (e.g., ADAMTS13) composition comprising solvent detergent treatment and nanofiltration.

In one embodiment, a method is provided for providing a virally safe ADAMTS protein (e.g., ADAMTS13) composition, the method comprising the steps of (a) culturing a cell harboring a nucleic acid encoding an ADAMTS protein (e.g., ADAMTS13) in a culture medium; (b) recovering a portion of the culture medium supernatant containing an ADAMTS protein (e.g., ADAMTS13); (c) exchanging the culture medium supernatant with a buffered solution containing zinc and calcium, to form a first ADAMTS protein (e.g., ADAMTS13) composition; (d) optionally further enriching the ADAMTS protein (e.g., ADAMTS13) with a chromatographic step; and (e) performing at least one virus inactivation or removal step, thereby providing a virally safe ADAMTS (e.g., ADAMTS13) composition. In one embodiment, the culture medium contains zinc, calcium, and optionally nicotinamide (vitamin B3). In a preferred embodiment, the step of culturing a cell comprises a continuous culture (e.g., perfusion or chemostatic culture). In another preferred embodiment, the culture is maintained at a temperature between 34° C. and 37° C. In yet another preferred embodiment, the culture is maintained at a pH between 6.9 and 7.2. In one embodiment, the virus removal step is nanofiltration.

1. Solvent and Detergent (S/D) Treatment

In order to inactivate various viral contaminants which may be present in ADAMTS culture, one or more ADAMTS (e.g., ADAMTS13) intermediate solutions may be subjected to a solvent detergent (S/D) treatment. Methods for the detergent treatment of solutions are well known in the art (for review see, Pelletier J P et al., *Best Pract Res Clin Haematol.* 2006; 19(1):205-42, the disclosure of which is expressly incorporated by reference herein in its entirety for all purposes). Generally, any standard S/D treatment may be used in conjunction with the methods provided herein. For example, an exemplary protocol for an S/D treatment is provided below.

In one embodiment, Triton X-100, Tween-20, and tri(n-butyl)phosphate (TNBP) are added to an ADAMTS (e.g., ADAMTS13) intermediate solution at final concentrations of at or about 1.0%, 0.3%, and 0.3%, respectively. The mixture is then stirred at a temperature at or about between 18° C. and 25° C. for at least about an hour.

2. Nanofiltration and Ultra/Diafiltration

In order to reduce the viral load of an ADAMTS protein (e.g., ADAMTS13) composition provided herein, the composition may be nanofiltered using a suitable nanofiltration device. In certain embodiments, the nanofiltration device will have a mean pore size of at or about between 15 nm and 200 nm. Examples of nanofilters suitable for this use include, without limitation, DVD, DV 50, DV 20 (Pall), Viresolve NFP®, Viresolve NFR® (Millipore), Planova® 15N, 20N, 35N, and 75N (Planova). In a specific embodiment, the nanofilter may have a mean pore size of at or about between 15 and 72 nm, or at or about between 19 and 35 nm, or of at or about 15 nm, 19 nm, 20 nm, 35 nm, or 72 nm. In a preferred embodiment, the nanofilter will have a mean pore size of at or about 19 nm, 20 nm, or 35 nm, such as an Asahi PLANOVA® 20N or PLANOVA® 35N filter or equivalent thereof.

Subsequent to nanofiltration, the filtrate may optionally be concentrated by ultrafiltration and/or the buffer composition adjusted by diafiltration. In certain embodiments, the ultrafiltration is carried out in a cassette with an open channel screen and the ultrafiltration membrane has a nominal molecular weight cut off (NMWCO) of less than at or about 175 kDa or less than at or about 170, 160, 150, 140, 130, 120, 110, 100, 90, 80, 70, 60, 50, 40, 30, or fewer kDa. In a preferred embodiment, the ultrafiltration membrane has a NMWCO of no more than 30 kDa. In another preferred embodiment, the ultrafiltration membrane has a NMWCO of no more than 30 kDa.

3. Lyophilization and Heat Treatment

In yet other embodiments, the viral activity of a lyophilized ADAMTS13 protein (e.g., ADAMTS13) composition, which may have previously been subjected to other viral inactivation or removal steps such as nanofiltration, may be further reduced by heat treatment of the lyophilized composition. Heat treatments for the inactivation of viral loads in blood factors are well known in the art (for example, see, Piszkiewicz et al., *Thromb Res.* 1987 Jul. 15; 47(2): 235-41; Piszkiewicz et al., *Curr Stud Hematol Blood Transfus.* 1989; (56):44-54; Epstein and Fricke, *Arch Pathol Lab Med.* 1990 March; 114(3):335-40).

VI. ADAMTS Compositions

Advantageously, it has been found that ADAMTS proteins, such as ADAMTS13, expressed in cell cultures supplemented with zinc, calcium, and/or nicotinamide (vitamin B3) have unexpectedly high specific activities. As provided herein, methods have been developed for the continuous expression and recovery of such ADAMTS proteins with high specific activities. For example, continuous cell culture methods provided herein allow for the expression of greater than 1 mg ADAMTS13 per liter per day with specific activities of greater than 1000 U/mg for more than a week or longer. Similarly, methods for reducing the loss of activity typically encountered during the purification of ADAMTS13 protein are also provided herein.

Accordingly, in one aspect, the present invention provides ADAMTS protein compositions (e.g., ADAMTS13 compositions) expressed in cell culture according to the methods provided herein. For example, ADAMTS protein compositions are provided, wherein the protein is expressed by culturing a cell harboring a nucleic acid encoding an ADAMTS protein in culture medium supplemented with at least one component selected from calcium, zinc, and nicotinamide (Vitamin B3). Also provided, are ADAMTS protein compositions (e.g., ADAMTS13 compositions) that are purified according to a method provided herein. For example, ADAMTS protein compositions are provided that have been purified according to a method comprising a buffer exchange step, wherein the exchange buffer includes zinc and calcium. In preferred embodiments of the invention, the ADAMTS protein composition is an ADAMTS13 composition.

In another aspect, the present invention provides ADAMTS protein compositions (e.g., ADAMTS13 compositions) that are prepared by a method comprising the expression of the ADAMTS protein in a cell culture according to any method provided herein. In a preferred embodiment, the ADAMTS protein is ADAMTS13.

In a related aspect, the present invention provides ADAMTS protein compositions (e.g., ADAMTS13 compositions) that are prepared by a method comprising the inclusion of both zinc and calcium in at least one buffer during the purification of the ADAMTS protein from a culture medium. In a preferred embodiment, the ADAMTS protein is ADAMTS13.

The present invention provides ADAMTS protein compositions (e.g., ADAMTS13 compositions) prepared by a method provided herein. In one embodiment, the ADAMTS composition (e.g., ADAMTS13 composition) is prepared by culturing a cell harboring a nucleic acid encoding an ADAMTS protein in culture medium supplemented with at least one component selected from calcium, zinc, and nicotinamide (Vitamin B3). In a specific embodiment, an ADAMTS composition is prepared by culturing a cell harboring a nucleic acid encoding an ADAMTS protein in culture medium supplemented with at least two components selected from calcium, zinc, and nicotinamide (Vitamin B3). In yet another embodiment, the culture medium is supplemented with calcium, zinc, and nicotinamide (Vitamin B3). In some embodiments, the culture medium may be an animal protein-free, an oligopeptide-free, or a chemically defined culture medium. In a preferred embodiment, the ADAMTS protein is ADAMTS13.

In one embodiment, an ADAMTS protein composition (e.g., ADAMTS13 composition) is prepared by culturing a cell harboring a nucleic acid encoding an ADAMTS protein in a culture medium comprising at least at or about 2 $\mu$M zinc. In another embodiment, the composition is prepared by culturing a mammalian cell harboring a nucleic acid encoding an ADAMTS protein in a culture medium comprising at least at or about 5 $\mu$M zinc. In one embodiment, the composition is prepared by culturing a mammalian cell harboring a nucleic acid encoding an ADAMTS protein in a culture medium comprising at or about between 2 $\mu$M and 12 $\mu$M zinc. In another embodiment, the composition is prepared by culturing a mammalian cell harboring a nucleic acid encoding an ADAMTS protein in a culture medium comprising at or about between 5 $\mu$M and 12 $\mu$M zinc. In yet other embodiments, the composition is prepared by culturing a mammalian cell harboring a nucleic acid encoding an ADAMTS protein in a culture medium comprising at least at or about 2 $\mu$M, or at least at or about 3 $\mu$M, 4 $\mu$M, 5 $\mu$M, 6 $\mu$M, 7 $\mu$M, 8 $\mu$M, 9 $\mu$M, 10 $\mu$M, 11 $\mu$M, 12 $\mu$M, 13 $\mu$M, 14 $\mu$M, 15 $\mu$M, 20 $\mu$M, 25 $\mu$M, 30 $\mu$M, or more zinc. In one embodiment, the culture is maintained at or about between 35° C. and 37° C. In a specific embodiment, the culture is maintained at or about 36° C. In another embodiment, the pH of the culture is maintained at or about between 6.9 and 7.3. In one embodiment, the temperature and/or pH of the culture is maintained for at least 7 days. In one embodiment, the method is performed under continuous culture conditions. In a specific embodiments, the method is performed under chemostat, turbidostat, or perfusion culture conditions operated in suspension mode. In other specific embodiments, the method is performed under chemostat, turbidostat, or perfusion culture conditions operated in adherent mode. In another embodiment, the method is performed under batch culture conditions. In specific embodiments, the method is performed under single-batch, repeated-batch, or fed-batch culture conditions operated in suspension mode. In other specific embodiments, the method is performed under single-batch, repeated-batch, or fed-batch culture conditions operated in adherent mode. In one embodiment, the cell harboring the nucleic acid encoding an ADAMTS protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine. In a preferred embodiment, the ADAMTS protein is ADAMTS13.

In one embodiment of an ADAMTS protein composition (e.g., ADAMTS13 composition), culture medium used for the expression of the ADAMTS protein may be supplemented with zinc at a final concentration of at least about 2 $\mu$M to at least about 12 $\mu$M. In certain embodiments, the culture medium may be supplemented with zinc at a final concentration of at least about 2 $\mu$M, or at least about 3 $\mu$M, 4 $\mu$M, 5 $\mu$M, 6 $\mu$M, 7 $\mu$M, 8 $\mu$M, 9 $\mu$M, 10 $\mu$M, 11 $\mu$M, 12 $\mu$M, 13 $\mu$M, 14 $\mu$M, 15 $\mu$M, 20 $\mu$M, 25 $\mu$M, 30 $\mu$M, or higher levels of zinc. Generally, any zinc salt may be used to supplement the mediums of the invention, non-limiting examples of acceptable salts include, $ZnSO_4.7H_2O$, $ZnSO_3.2H_2O$, $(C_6H_5O_7)_2Zn_3.2H_2O$, $ZnBr_2$, $ZnBr_2.2H_2O$, $ZnCl_2$, $Zn(NO_3)_2.6H_2O$, $Zn(H_2PO_4)_2.H_2O$, $(C_2H_3O_2)_2Zn.2H_2O$, and the like. In certain embodiments, a pharmaceutically acceptable salt of zinc is used to supplement the culture mediums of the invention. In a preferred embodiment, the ADAMTS protein is ADAMTS13.

In another embodiment, an ADAMTS protein composition (e.g., ADAMTS13 composition) is prepared by culturing a cell harboring a nucleic acid encoding an ADAMTS protein in a culture medium comprising at least at or about 0.5 mM calcium. In another embodiment, an ADAMTS composition is prepared by culturing a mammalian cell harboring a nucleic acid encoding an ADAMTS protein in a culture medium comprising at least at or about 1.5 mM calcium. In one embodiment, an ADAMTS composition is prepared by culturing a mammalian cell harboring a nucleic acid encoding an ADAMTS protein in a culture medium comprising at or about between 0.5 mM and 1.5 mM calcium. In yet other embodiments, an ADAMTS composition is prepared by culturing a mammalian cell harboring a nucleic acid encoding an ADAMTS protein in a culture medium comprising at least at or about 0.5 mM, or at least at or about 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.25 mM, 2.5 mM, 2.75 mM, 3.0 mM, 3.5 mM, 4.0 mM, 4.5 mM, 5.0 mM, or more calcium. In one embodiment, the culture is maintained at or about between 35° C. and 37° C. In a specific embodiment, the culture is maintained at or about 36° C. In another embodiment, the pH of the culture is maintained at or about between 6.9 and 7.3. In one embodiment, the temperature and/or pH of the culture is maintained for at least 7 days. In one embodiment, the method is performed under continuous culture conditions. In a specific embodiments, the method is performed under chemostat, turbidostat, or perfusion culture conditions operated in suspension mode. In other specific embodiments, the method is performed under chemostat, turbidostat, or perfusion culture conditions operated in adherent mode. In another embodiment, the method is performed under batch culture conditions. In specific embodiments, the method is performed under single-batch, repeated-batch, or fed-batch culture conditions operated in suspension mode. In other specific embodiments, the method is performed under single-batch, repeated-batch, or fed-batch culture conditions operated in adherent mode. In one embodiment, the cell harboring the nucleic acid encoding an ADAMTS protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine. In a preferred embodiment, the ADAMTS protein is ADAMTS13.

Generally, any calcium salt may be used to supplement the mediums of the invention. Non-limiting examples of acceptable salts include $CaCl_2$, $CaCl_2$, $CaFPO_3.2H_2O$, $CaI_2$, $CaBr_2$, $(C_2H_3O)_2)_2Ca$, $(CHO_2)_2Ca$, $(C_6H_7O_6)_2Ca$, $(C_6H_5O_7)_2Ca_3.2H_2O$, and the like. In certain embodiments, a pharmaceutically acceptable salt of calcium is used to supplement the culture mediums of the invention.

In another embodiment, an ADAMTS protein composition (e.g., ADAMTS13 composition) is prepared by culturing a cell harboring a nucleic acid encoding an ADAMTS protein in a culture medium comprising at least at or about 2 mg/L nicotinamide (vitamin B3). In another embodiment, an ADAMTS composition is prepared by culturing a mammalian cell harboring a nucleic acid encoding an ADAMTS protein in a culture medium comprising at least at or about 7 mg/L nicotinamide (vitamin B3). In one embodiment, an ADAMTS composition is prepared by culturing a mammalian cell harboring a nucleic acid encoding an ADAMTS protein in a culture medium comprising at or about between 2 mg/L and 10 mg/L nicotinamide (vitamin B3). In yet other embodiments, an ADAMTS composition is prepared by culturing a mammalian cell harboring a nucleic acid encoding an ADAMTS protein in a culture medium comprising at least at or about 2 mg/L, 3 mg/L, 4 mg/L, 5 mg/L, 6 mg/L, 7 mg/L, 8 mg/L, 9 mg/L, 10 mg/L, 15 mg/L, 20 mg/L, or higher concentrations of nicotinamide (vitamin B3). In one embodiment, the culture is maintained at or about between 35° C. and 37° C. In a specific embodiment, the culture is maintained at or about 36° C. In another embodiment, the pH of the culture is maintained at or about between 6.9 and 7.3. In one embodiment, the temperature and/or pH of the culture is maintained for at least 7 days. In one embodiment, the method is performed under continuous culture conditions. In a specific embodiments, the method is performed under chemostat, turbidostat, or perfusion culture conditions operated in suspension mode. In other specific embodiments, the method is performed under chemostat, turbidostat, or perfusion culture conditions operated in adherent mode. In another embodiment, the method is performed under batch culture conditions. In specific embodiments, the method is performed under single-batch, repeated-batch, or fed-batch culture conditions operated in suspension mode. In other specific embodiments, the method is performed under single-batch, repeated-batch, or fed-batch culture conditions operated in adherent mode. In one embodiment, the cell harboring the nucleic acid encoding an ADAMTS protein is a mammalian cell. In particular embodiments, the mammalian cell is a hamster, human, or murine cell. In a specific embodiment, the cell is a CHO cell line, an HEK 293 cell line, or a BHK cell line. In another embodiment, the mammalian cell is cultured in an animal protein and/or polypeptide free culture medium. In yet another embodiment, the mammalian cell is cultured in a synthetic culture medium, which may or may not be free of animal proteins and polypeptides. In one embodiment, the culture medium further comprises a polyamine at or about between 0.5 mg/L and 30 mg/L. In another embodiment, the culture medium further comprises a polyamine at or about between 2 mg/L and 8 mg/L. In a specific embodiment, the polyamine is putrescine. In a preferred embodiment, the ADAMTS protein is ADAMTS13.

In one embodiment, an ADAMTS composition is prepared by culturing a cell harboring a nucleic acid encoding an ADAMTS protein (e.g., ADAMTS13) in a culture medium supplemented with both zinc and calcium. In certain embodiments, the zinc and calcium concentrations can be any of those described herein. In certain embodiments, the zinc and calcium concentrations will be one of Var. 94 to Var. 113 (Table 7). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one embodiment, the culture is a perfusion culture. In another embodiment, the culture is a chemostatic culture. In other embodiments, the culture is a fed-batch or repeated-batch culture. In a preferred embodiment, the ADAMTS protein is ADAMTS13.

In one embodiment, an ADAMTS composition is prepared by culturing a cell harboring a nucleic acid encoding an ADAMTS protein (e.g., ADAMTS13) in a culture medium supplemented with both zinc and nicotinamide (vitamin B3). In certain embodiments, the zinc and nicotinamide (vitamin B3) concentrations can be any of those described herein. In certain embodiments, the zinc and nicotinamide (vitamin B3) concentrations will be one of Var. 114 to Var. 133 (Table 8). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one embodiment, the culture is a perfusion culture. In another embodiment, the culture is a chemostatic culture. In other embodiments, the culture is a fed-batch or repeated-batch culture. In a preferred embodiment, the ADAMTS protein is ADAMTS13.

In one embodiment, an ADAMTS composition is prepared by culturing a cell harboring a nucleic acid encoding an ADAMTS protein (e.g., ADAMTS13) in a culture medium supplemented with both calcium and nicotinamide (vitamin B3). In certain embodiments, the calcium and nicotinamide (vitamin B3) concentrations can be any of those described herein. In certain embodiments, the calcium and nicotinamide (vitamin B3) concentrations will be one of Var. 134 to Var. 149 (Table 9). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one embodiment, the culture is a perfusion culture. In another embodiment, the culture is a chemostatic culture. In other embodiments, the culture is a fed-batch or repeated-batch culture. In a preferred embodiment, the ADAMTS protein is ADAMTS13.

In one embodiment, an ADAMTS composition is prepared by culturing a cell harboring a nucleic acid encoding an ADAMTS protein (e.g., ADAMTS13) in a culture medium supplemented with zinc, calcium, and nicotinamide (vitamin B3). In certain embodiments, the zinc, calcium, and nicotinamide (vitamin B3) concentrations can be any of those described herein. In certain embodiments, the zinc, calcium, and nicotinamide (vitamin B3) concentrations will be one of variations Var. 14 to Var. 93 (Table 3 to Table 6). In certain embodiments, the culture is maintained for at least 7 days, or at least 14 days, 21 days, 28 days, or at least 5 weeks, 6 weeks, 7 weeks, or at least 2 months, or 3, 4, 5, 6, 7, 8, 9, 10, 11, 12, 13, 14, 15, 16, 17, 18 months or longer. In one embodiment, the culture is a perfusion culture. In another embodiment, the culture is a chemostatic culture. In other embodiments, the culture is a fed-batch or repeated-batch culture. In a preferred embodiment, the ADAMTS protein is ADAMTS13.

In another embodiment, ADAMTS13 compositions are provided with high specific activities, for example, a specific activity of at least 600 U/mg A13 protein. In another embodiment, the ADAMTS13 composition has a specific activity of at least 700 U/mg. In another embodiment, the ADAMTS13 composition has a specific activity of at least 800 U/mg. In another embodiment, the ADAMTS13 composition has a specific activity of at least 900 U/mg. In another embodiment, the ADAMTS13 composition has a specific activity of at least 1000 U/mg. In another embodiment, the ADAMTS13 composition has a specific activity of at least 1100 U/mg. In another embodiment, the ADAMTS13 composition has a specific activity of at least 1200 U/mg. In another embodiment, the ADAMTS13 composition has a specific activity of at least 1300 U/mg. In another embodiment, the ADAMTS13 composition has a specific activity of at least 1400 U/mg. In another embodiment, the ADAMTS13 composition has a specific activity of at least 1500 U/mg. In another embodiment, the ADAMTS13 composition has a specific activity of at least 1600 U/mg. In another embodiment, the ADAMTS13 composition has a specific activity of at least 1700 U/mg. In another embodiment, the ADAMTS13 composition has a specific activity of at least 1800 U/mg. In another embodiment, the ADAMTS13 composition has a specific activity of at least 1900 U/mg. In another embodiment, the ADAMTS13 composition has a specific activity of at least 2000 U/mg. In another embodiment, the ADAMTS13 composition has a specific activity of at least 2100 U/mg. In another embodiment, the ADAMTS13 composition has a specific activity of at least 2200 U/mg. In another embodiment, the ADAMTS13 composition has a specific activity of at least 2300 U/mg. In another embodiment, the ADAMTS13 composition has a specific activity of at least 2400 U/mg. In another embodiment, the ADAMTS13 composition has a specific activity of at least 2500 U/mg.

VII. Examples

Example 1

Fed-batch experiments were performed using bioreactor cultures of the recombinant HEK293 cell line 1020/1 013-2 expressing human ADAMTS13 in chemically defined BACD-A13 medium. The effect of supplementing the culture medium with additional zinc was investigated.

Recombinant HEK293 cells expressing human ADAMTS13 were cultivated by fed-batch cell-cultures in 1.5 L bioreactors with blade impellers under an inline controlled pH of 7.20 at 37° C. with a dissolved oxygen concentration of 20% air saturation. Cell suspension was transferred to 2 identical bioreactors containing a DMEM/F12 based chemically defined culture medium (BACD-A13; Table 12). The two cultures were grown in BACD-A13 mediums prepared with either 0.432 mg/L $ZnSO_4.7H_2O$, as in DMEM/F12, or with an additional supplementation of 1 mg/L $ZnSO_4.7H_2O$ for a final concentration of 1.432 mg/L. The two fed-batch cultures were otherwise treated the same and thus may be compared directly to one another.

The activity of A13 in culture supernatants were measured by FRETS-VWF73 assay after centrifuging or filtering the supernatants to remove residual cells. The total amount of A13 was measured by ELISA, using an A13-specific antibody (Table 10). Supernatant from the culture employing BACD-A13 medium with a standard DMEM/F12 zinc concentration had an A13 activity of 728 and 826 mU/mL on days 3 and 6, respectively. Specific activities for the cultures were 482 mU/µg and 526 mU/µg A13, respectively. In contrast, supernatants from cultures having additional supplementation of Zn, while having only slightly improved yields of A13 expression (7% and 19% greater at days 3 and 6, respectively), showed dramatically improved total and specific activities A13 activities (Table 11). As can be seen by comparing the results in Table 10 and Table 11, total A13 FRETS-VWF73 activity was 118% higher (1589 vs. 728) at day 3 and 61% higher (1381 vs. 728) at day 6 for cultures grown in the presence of 1.432 mg/L $ZnSO_4.7H_2O$ as compared to cultures grown at 0.432 mg/L $ZnSO_4.7H_2O$. Similarly, the specific activity of the A13 protein in the supplemented cultures was 104% higher (981 vs. 482 mU/µg) at day 3 and 42% higher (739 vs. 526 mU/µg) at day 6.

Samples from the bioreactors were taken and analyzed for A13 by ELISA, A13 activity was measured by FRETS-VWF73 assay. Cell counts were determined by Nucleocounter technology. Dilution rates were measured and used for calculation of growth rates and volumetric productivities.

TABLE 10

Fermentation data for fed-batch culture 1 performed in a 1.5 L bioreactor with BACD-A13 medium without zinc supplementation.

| Day Supernatant Harvested | Cell Concentration [10⁶ Cells/ml] | Specific Growth Rate [1/d] | A13 FRETS [mU/ml] | A13 ELISA [µg/ml] | Specific Activity [mU/µg] | FRETS Yield [U/L/d] | A13 Yield [mg/L/d] |
|---|---|---|---|---|---|---|---|
| 3 | 2.18 | 0.619 | 728 | 1.51 | 482 | 228 | 0.41 |
| 6 | 1.88 | 0.256 | 826 | 1.57 | 526 | 178 | 0.32 |

TABLE 11

Fermentation data for fed-batch experiment performed in a 1.5 L bioreactor with BACD-A13 medium with zinc supplementation.

| Day Supernatant Harvested | Cell Concentration [10⁶ Cells/ml] | Specific Growth Rate [1/d] | A13 FRETS [mU/ml] | A13 ELISA [µg/ml] | Specific Activity [mU/µg] | FRETS Yield [U/L/d] | A13 Yield [mg/L/d] |
|---|---|---|---|---|---|---|---|
| 3 | 2.48 | 0.662 | 1589 | 1.62 | 981 | 515 | 0.45 |
| 6 | 1.38 | 0.11 | 1381 | 1.87 | 739 | 249 | 0.41 |

TABLE 12

Composition of the chemically defined BACD-A13 cell culture medium.

| BACD-A13 Cell Culture Medium Composition | Standard concentration mg/L |
|---|---|
| Amino Acids | |
| L-Alanine | 13.3500 |
| L-Arginine HCl | 147.5000 |
| L-Asparagine-$H_2O$ | 45.1600 |
| L-Aspartic Acid | 19.9500 |
| L-Cysteine HCl-$H_2O$ | 32.5500 |
| L-Cystine 2HCl | 102.3500 |
| L-Glutamic Acid | 22.0500 |
| Glycine | 26.2500 |
| L-Histidine-$H_2O$ HCl | 51.4800 |
| L-Isoleucine | 74.4700 |
| L-Leucine | 119.0500 |
| L-Lysine HCl | 146.2500 |
| L-Methionine | 100.0000 |
| L-Phenylalanine | 60.4800 |
| L-Proline | 63.7400 |
| L-Serine | 36.7500 |
| L-Threonine | 53.4500 |
| L-Tryptophan | 29.0100 |
| L-Tyrosine 2Na 2H2O | 75.7900 |
| L-Valine | 82.8500 |
| salts | |
| Calcium Chloride (CaCl2) | Variable (58.3-174.9) |
| Copper Sulfate ($CuSO_4$—$5H_2O$) | 0.0026 |
| Ferric Nitrate ($Fe(NO_3)_3$—$9H_2O$) | 0.0500 |
| Ferrous Sulfate ($FeSO_4$—$7H_2O$) | 1.0170 |
| Magnesium Chloride (MgCl2) | 28.6400 |
| Magnesium Sulfate (MgSO4) | 48.8400 |
| Potassium Chloride (KCl) | 311.8000 |
| Sodium Chloride (NaCl) | 5495.5000 |
| Na2HPO4 Anhydrous | 106.5100 |
| NaH2PO4 Anhydrous | 54.3500 |
| Zinc Sulfate Heptahydrate (ZnSO4—27H2O) | Variable (0.432-3.432) |
| Sodium selenite•anhydrous | 0.0087 |
| Vitamins | |
| Ascorbic Acid | 3.499 |
| Biotin | 0.0035 |
| Choline Chloride | 8.980 |
| D-Ca-Pantothenate | 2.240 |
| Folic Acid | 2.650 |
| I-Inositol | 12.600 |
| Nicotinamide | Variable (2.0-7.0) |
| Pyridoxine HCl | 2.031 |
| Riboflavin | 0.219 |
| Thiamine HCl | 2.170 |
| Vitamin B12 | 0.680 |
| miscellaneous | |
| D-Glucose | 5000.00 |
| Linoleic Acid | 0.042 |
| Lipoic Acid | 0.105 |
| Putrescine 2HCl | 3.681 |
| Thymidine | 0.365 |
| Hypoxanthine Na | 2.390 |
| Sodium Pyruvate | 55.000 |
| L-Glutamin | 1000.0000 |
| Pluronic F68 | 1000.0000 |
| Ethanolamin | 1.5300 |
| Na-Hydrogencarbonat | 1.5000 |

Example 2

Fed-batch experiments were performed using bioreactor cultures of the recombinant CHO cell line #938 expressing human ADAMTS13 in chemically defined BACD-A13 medium. The effect of supplementing the culture medium with additional zinc and/or vitamin B3 was investigated.

Recombinant CHO cells expressing human ADAMTS13 were adapted to a chemically defined BCS medium (BCS medium). Clone #938 from Development Working Cell Bank #01 (DWCB #01) was thawed and cell inoculum was prepared in BCS medium. Cells were transferred to two 1.5 L bioreactors with blade impellers and grown under fed-batch cell-culture in proprietary BACD-A13 medium with an inline controlled pH of 7.20 at 37° C. with a dissolved oxygen concentration of 20% air saturation. The two cultures were grown in BACD-A13 mediums prepared with either 0.432 mg/L $ZnSO_4.7H_2O$, as in DMEM/F12, or with an additional supplementation of 1 mg/L $ZnSO_4.7H_2O$ for a final concentration of 1.432 mg/L. The two fed-batch cultures were otherwise treated the same and thus may be compared directly to one another. Supernatants were harvested at 4 and 7 days and assayed for A13 protein and activity levels. After the harvest on day 7, both cultures were supplemented with an additional 5 mg/L nicotinamide (vitamin B3), for a final concentration of 7.02 mg/L, and grown under identical conditions for an additional 4 days. Supernatants were again harvested at day 11 and A13 protein and activity levels were assayed.

In the first culture, grown without zinc supplementation, A13 activity levels in the harvested supernatant were 642 and 488 mU/ml on days 4 and 7, respectively (Table 13). Specific activities for these supernatants were 371 and 273 mU/µg on days 4 and 7, respectively. As seen previously in example 1, the total and specific activities of the A13 in the culture supernatant supplemented with additional zinc were significantly increased (compare Table 13 and Table 14 at harvest days 4 and 7). As before, the total A13 produced in both cultures was similar, however, A13 from the supernatant of the second culture, supplemented with additional zinc, had 40% and 104% greater total activity at days 4 and 7, respectively, as well as 78% and 75% greater specific activity at days 4 and 7 (Table 14 vs. Table 13). Other parameters, including total A13 yield and cell growth rate appeared to be unaffected by the additional zinc supplementation.

After harvesting the supernatants on day 7, both cultures were further supplemented with an additional 5 mg/L nicotinamide (vitamin B3) and grown under identical conditions for an additional 4 days. Supernatants were harvested as before on day 11. Vitamin B3 supplementation resulted in an increase in the total FRETS-VWF73 activity and the specific activity of A13 found in the supernatants of both cultures (Table 13 and Table 14, day 11). Notably, these values approximately doubled in both cultures. At day 11, the supernatant from culture 2, supplemented with addition zinc and vitamin B3, demonstrated nearly 200% greater (2366 vs. 791 mU/mL) total activity and 174% greater (1189 vs. 432 mU/µg) specific activity than did supernatant harvested from culture 1.

Supplementation of the medium with nicotinamide alone resulted in about a 60% increase in the total activity (791 mU/ml vs. 488 mU/ml; compare Table 13 at days 7 and 11) and specific activity (432 mU/µg vs. 273 mU/µg; compare Table 13 at days 7 and 11) of A13. Similarly, supplementation of the medium with zinc alone resulted in increases of between about 70% and 80% in the total activity and specific activity of A13 (compare Table 13 and Table 14 at days 4 and 7). Surprisingly, supplementation of the culture medium with both nicotinamide and zinc resulted in a synergistic increase of between about 300% to 400% total activity (compare Table 14 day 11 with Table 13 days 4 and 7) and between about 200% to 300% specific activity (compare Table 14 day 11 with Table 13 days 4 and 7) of A13, demonstrating an unexpected synergistic interaction between the effects of zinc and nicotinamide.

TABLE 13

Fermentation data for batch experiment CP_07/18_M04: hA13 CHO Klon #985/1 938 DWCB#01.

| Day Supernatant Harvested | Cell Concentration [$10^6$ Cells/ml] | Specific Growth Rate [1/d] | A13 FRETS [mU/ml] | A13 ELISA [µg/ml] | Specific Activity [mU/µg] | FRETS Yield [U/L/d] | A13 Yield [mg/L/d] |
|---|---|---|---|---|---|---|---|
| 4* | 2.33 | 0.539 | 642 | 1.73 | 371 | 161 | 0.43 |
| 7* | 1.58 | 0.407 | 488 | 1.79 | 273 | 120 | 0.48 |
| 11† | 1.65 | 0.413 | 791 | 1.83 | 432 | 173 | 0.37 |

*BAV-CD-A13; 0.432 mg/L ZnSO$_4$•7H$_2$O; 2 mg/L nicotinamide
†BAV-CD-A13; 0.432 mg/L ZnSO$_4$•7H$_2$O; 7 mg/L nicotinamide

TABLE 14

Fermentation data for batch experiment CP_07/18_M07: hA13 CHO Klon #985/1 985 DWCB#01.

| Day Supernatant Harvested | Cell Concentration [$10^6$ Cells/ml] | Specific Growth Rate [1/d] | A13 FRETS [mU/ml] | A13 ELISA [µg/ml] | Specific Activity [mU/µg] | FRETS Yield [U/L/d] | A13 Yield [mg/L/d] |
|---|---|---|---|---|---|---|---|
| 4* | 1.73 | 0.527 | 898 | 1.36 | 660 | 224 | 0.34 |
| 7* | 2.10 | 0.505 | 996 | 2.08 | 479 | 252 | 0.57 |
| 11† | 1.88 | 0.420 | 2366 | 1.99 | 1189 | 550* | 0.41 |

*BAV-CD-A13; 1.432 mg/L ZnSO$_4$•7H$_2$O; 2 mg/L nicotinamide
†BAV-CD-A13; 1.432 mg/L ZnSO$_4$•7H$_2$O; 7 mg/L nicotinamide Example 3

A Chemostat cell-culture of the recombinant CHO cell line #640-2 expressing human ADAMTS13, was grown in chemically defined BACD-A13 medium supplemented with additional zinc and vitamin B3. The 10 L culture was maintained for 53 days and A13 protein and activity production was monitored over time.

Recombinant CHO cells expressing human ADAMTS13 were adapted to a chemically defined proprietary medium (BCS medium). A cell bank vial was thawed and cell inoculum was prepared in BCS medium. Cells propagated from the A13 expression clone #640-2 were transferred to a 10 L bioreactor with Rushton type impellers and cultivated in repeated batch cultures with proprietary BACD-A13 medium under an inline controlled pH of 7.15-7.20 at 37° C. with a dissolved oxygen concentration of 20% air saturation. After 2 batch cultures were grown to the final working volume of 10 L, the bioreactor was switched to continuous medium feed on day 5 and operated for an additional 48 days in a chemostat mode.

Samples of the supernatant from the bioreactors were taken weekly and analyzed for A13 protein production by ELISA and A13 activity by FRETS-VWF73 assay. Cell counts were determined by Nucleocounter technology. Dilution rates were measured and used for calculation of growth rates and volumetric productivities.

Under continuous culture conditions using chemically defined BACD-A13 medium supplemented with zinc and nicotinamide at a final concentration of 1.432 mg/L ZnSO$_4$.7H$_2$O and 7.02 mg/L nicotinamide, high levels of A13 protein production, between 0.9 and 1.3 mg/L/D, and specific activities, between about 800 and 1100 mU/µg A13, were achieved (Table 15). These results were consistent with protein production and specific activities achieved with CHO clone #938, as in example 2. Notably, volumetric and cell specific productivities increased over time in the long term culture, likely due to increasing growth and dilution rates over time. The high specific activity of the expressed A13 could be at least maintained at a constantly high level over at least entire 7 weeks the culture was grown under chemostatic conditions. In fact, the specific activity of the A13 produced in the culture actually increased from about 800 mU/µg A13 at week 2 to about 1100 mU/µg A13 at week 7.

TABLE 15

Fermentation data for continuous culture experiment
CP_07/30_F02: hA13 CHO Klon #987/1 640-2.

| Chemostat Culture Week No. | Cell Concentration [10$^6$ Cells/ml] | Specific Growth Rate [1/d] | Dilution Rate [1/d] | A13 FRETS [mU/ml] | A13 ELISA [µg/ml] | Specific Activity [mU/µg] | FRETS Yield [U/L/d] | A13 Yield [mg/L/d] |
|---|---|---|---|---|---|---|---|---|
| 2 | 1.43 | 0.36 | 0.36 | 1954 | 2.48 | 788 | 713 | 0.91 |
| 3 | 1.56 | 0.41 | 0.40 | 2254 | 2.32 | 972 | 913 | 0.94 |
| 4 | 1.46 | 0.38 | 0.40 | 2244 | 2.41 | 931 | 889 | 0.95 |
| 5 | 1.58 | 0.43 | 0.43 | 2514 | 2.88 | 873 | 1086 | 1.24 |
| 6 | 1.70 | 0.51 | 0.46 | 2737 | 2.71 | 1010 | 1270 | 1.26 |
| 7 | 1.76 | 0.53 | 0.52 | 2322 | 2.18 | 1065 | 1200 | 1.13 |

Example 4

Fed-batch and chemostat cell-culture experiments were performed using bioreactor cultures of the recombinant CHO cell line #640-2 expressing human ADAMTS13 in chemically defined BACD-A13 medium. The effect of supplementing the culture medium with different levels of zinc was investigated.

Recombinant CHO cells expressing human ADAMTS13 were adapted to a chemically defined proprietary medium, BCS medium, in fed-batch mode. Briefly, DWCB #05 was thawed and cell inoculum was prepared in BCS medium. Cells were transferred to a 1.5 L bioreactors with blade impellers and in proprietary BACD-A13 medium supplemented with nicotinamide at a final concentration of 7 mg/L, but without zinc supplementation under an inline controlled pH of 7.20 at 37° C. with a dissolved oxygen concentration of 20% air saturation. The batch cell suspension was then divided into three identical bioreactors containing BACD-A13 medium supplemented with nicotinamide at a final concentration of 7 mg/L with different Zn supplementations (0 mg/L; 0.5 mg/L; and 1.0 mg/L ZnSO$_4$.7H$_2$O to a final concentration of 0.432 mg/L; 0.932 mg/L; and 1.432 mg/L ZnSO$_4$.7H$_2$O).

BACD-A13 mediums included 0.432 mg/L ZnSO$_4$.7H$_2$O with or without additional supplementation of zinc. Otherwise, the cultures and medium were the same and thus can be compared directly to one another. Cultures were grown in fed-batch mode for about a week and the supernatant was assayed for A13 protein production and FRETS-VWF73 activity. All three bioreactors were then switched to chemostat culture mode and operated for about 2 weeks under continuous culture conditions using the mediums with different zinc supplementations, as described above.

Under fed-batch culture conditions, consistent with the results seen in examples 1 and 2, supplementation of the medium with either 0.5 mg/L or 1.0 mg/L ZnSO$_4$.7H$_2$O significantly increased the specific activity of A13 protein in the supernatant (785 mU/µg and 876 mU/µg, respectively) as compared to medium not supplemented with additional zinc (437 mU/µg) (Table 16). As before, other parameters, including total A13 protein production and specific cell growth, were unaffected by supplementation with additional zinc.

TABLE 16

Fermentation data for fed-batch experiments of human A13 expression in medium with and without additional zinc supplementation.

| Additional Zinc | Cell Concentration [10$^6$ Cells/ml] | Specific Growth Rate [1/d] | A13 FRETS [mU/ml] | A13 ELISA [µg/ml] | Specific Activity [mU/µg] | FRETS Yield [U/L/d] | A13 Yield [mg/L/d] |
|---|---|---|---|---|---|---|---|
| 0 | 1.44 | 0.420 | 853.0 | 1.952 | 437 | 230.3 | 0.506 |
| 0.5 mg/L | 1.73 | 0.502 | 1687.7 | 2.151 | 785 | 470.0 | 0.563 |
| 1.0 mg/L | 1.44 | 0.441 | 1589.2 | 1.814 | 876 | 430.8 | 0.472 |

After switching the bioreactors to chemostat mode, the cultures were grown under continuous culture conditions for about a week (week 2) using the mediums with different zinc supplementations, as described above. Samples of the supernatant from the bioreactors were taken weekly and analyzed for A13 protein production by ELISA and A13 activity by FRETS-VWF73 assay. Similar to the results seen for cultures grown under fed-batch mode, supplementation of the growth medium used for continuous culture growth with additional zinc resulted in the substantial improvement of A13 specific activities (697 mU/µg and 729 mU/µg for 0.5 mg/L and 1.0 mg/L ZnSO$_4$.7H$_2$O supplementation, respectively) after a week, as compared to no supplementation (553 mU/µg) (Table 17, Table 18, and Table 19).

Previously, it had been seen that the specific activity of A13 expressed in continuous cell-cultivation actually improved over an extended period of time (see, example 3). To investigate whether or not this result could be repeated, the cultures grown in medium supplemented with additional zinc were continued for an additional week. As seen in Table 18 and Table 19, the specific activity of A13 in the supernatants of both cultures again increased over time. The specific activity of A13 found in the supernatant of the medium supplemented with 0.5 mg/L ZnSO$_4$.7H$_2$O increased from 697 mU/mg at week 2 to 759 mU/mg at week 3 (Table 18). Similarly, the specific activity of A13 found in the supernatant of the medium supplemented with 1.0 mg/L ZnSO$_4$.7H$_2$O increased from 729 mU/mg at week 2 to 812 mU/mg at week 3 (Table 19). As before, specific cell growth was unaffected by supplementation with additional zinc. Notably, however, A13 protein production appeared to increase in both cultures supplemented with additional zinc as compared to production in cultures not supplemented with zinc.

TABLE 17

Fermentation data for chemostat cell-culture experiments without additional supplementation of zinc.

| Chemostat Culture Week No. | Cell Concentration [10⁶ Cells/ml] | Specific Growth Rate [1/d] | Dilution Rate [1/d] | A13 FRETS [mU/ml] | A13 ELISA [µg/ml] | Specific Activity [mU/µg] | FRETS Yield [U/L/d] | A13 Yield [mg/L/d] |
|---|---|---|---|---|---|---|---|---|
| 2 | 1.25 | 0.340 | 0.339 | 1091.8 | 1.973 | 553 | 370.1 | 0.669 |

TABLE 18

Fermentation data for chemostat cell-culture experiments with 0.5 mg/L additional supplementation of zinc.

| Chemostat Culture Week No. | Cell Concentration [10⁶ Cells/ml] | Specific Growth Rate [1/d] | Dilution Rate [1/d] | A13 FRETS [mU/ml] | A13 ELISA [µg/ml] | Specific Activity [mU/µg] | FRETS Yield [U/L/d] | A13 Yield [mg/L/d] |
|---|---|---|---|---|---|---|---|---|
| 2 | 1.37 | 0.350 | 0.341 | 1725.5 | 2.476 | 697 | 588.4 | 0.844 |
| 3 | 1.37 | 0.362 | 0.353 | 1971.7 | 2.597 | 759 | 696.0 | 0.917 |

TABLE 19

Fermentation data for chemostat cell-culture experiments with 1.0 mg/L additional supplementation of zinc.

| Chemostat Culture Week No. | Cell Concentration [10⁶ Cells/ml] | Specific Growth Rate [1/d] | Dilution Rate [1/d] | A13 FRETS [mU/ml] | A13 ELISA [µg/ml] | Specific Activity [mU/µg] | FRETS Yield [U/L/d] | A13 Yield [mg/L/d] |
|---|---|---|---|---|---|---|---|---|
| 2 | 1.21 | 0.327 | 0.340 | 1681.7 | 2.307 | 729 | 571.8 | 0.784 |
| 3 | 1.21 | 0.330 | 0.353 | 1892.2 | 2.331 | 812 | 667.9 | 0.823 |

Example 5

Fed-batch and chemostat cell-culture experiments were performed using bioreactor cultures of the recombinant CHO cell line # F6 expressing human ADAMTS13 in chemically defined BACD-A13 medium. The effect of supplementing the culture medium with higher levels of zinc was investigated.

Recombinant CHO cells expressing human ADAMTS13 were adapted to a chemically defined proprietary medium, BCS medium, in fed-batch mode. The adapted populations were subcloned and a clone # F6 was derived therefrom.

Briefly, DWCB #19 was thawed and cell inoculum was prepared in BCS medium. Cells were transferred to three 1.5 L bioreactors with blade impellers and in proprietary BACD-A13 medium supplemented with 1.0 mg/L, 2.0 mg/L, and 3.0 mg/L ZnSO₄.7H₂O for final concentrations of 1.432 mg/L, 2.432 mg/L, and 3.432 mg/L ZnSO₄.7H₂O, respectively. Cultures were grown under an inline controlled pH of 7.15 at 36° C. with a dissolved oxygen concentration of 20% air saturation.

Cultures were grown in repeated batch mode (3 batches) for about a week and the supernatant was assayed for A13 protein production and FRETS-VWF73 activity. All three bioreactors were then switched to chemostat culture mode and operated for 10 days under continuous culture conditions using the mediums with different zinc supplementations, as described above.

Under fed-batch culture conditions, supplementation of the culture mediums with increasing amounts of zinc further increased the specific activity of A13 secreted in the culture supernatants. Consistent with the previous results reported above, supplementation of the medium with an additional 1.0 mg/L ZnSO₄.7H₂O resulted in a high specific activity of 806 mU/µg. Further increases in the zinc concentration, i.e. supplementation with 2.0 mg/L and 3.0 mg/L, resulted in even higher levels of A13 specific activity (880 mU/µg and 889 mU/µg, respectively) (Table 20). As before, other parameters, including total A13 protein production and specific cell growth, were unaffected by supplementation with additional zinc.

TABLE 20

Fermentation data for batch experiments with additional supplementation of zinc (mean data of 3 batches).

| Additional Zinc | Cell Concentration [10⁶ Cells/ml] | Specific Growth Rate [1/d] | A13 FRETS [mU/ml] | A13 ELISA [µg/ml] | Specific Activity [mU/µg] | FRETS Yield [U/L/d] | A13 Yield [mg/L/d] |
|---|---|---|---|---|---|---|---|
| 1.0 mg/L | 1.78 | 0.592 | 1666.6 | 2.074 | 806 | 633.8 | 0.687 |
| 2.0 mg/L | 1.68 | 0.596 | 1678.0 | 1.883 | 880 | 621.8 | 0.619 |
| 3.0 mg/L | 1.55 | 0.589 | 1670.1 | 1.844 | 889 | 580.8 | 0.625 |

After switching the bioreactors to chemostat mode, the cultures were grown under continuous culture conditions for 10 days using the mediums with different zinc supplementations, as described above. Samples of the supernatant from the bioreactors were analyzed for A13 protein production by ELISA and A13 activity by FRETS-VWF73 assay. Unlike the results seen for cultures grown under fed-batch mode, supplementation of the growth medium used for continuous culture growth with higher levels of zinc resulted in a decrease in the specific growth rate and overall cell viability. The chemostat culture grown in medium supplemented with an additional 1.0 mg/L $ZnSO_4.7H_2O$ continued to display high cell viability (88.6%) and a specific growth rate (0.256 per day) (Table 21) consistent with the previous results described above.

In contrast, cultures grown in mediums supplemented with higher levels of $ZnSO_4.7H_2O$, 2.0 mg/L and 3.0 mg/L, displayed significant reductions in the levels of cell viability (72.1% and 80.4%, respectively) and specific growth rates (0.091 and 0.134 per day, respectively). Notably, however, the specific activity of A13 in the two culture supernatants remained high (863 mU/μg and 771 mU/μg, respectively) (Table 21).

of time, they were kept at less than −15° C. between end of diafiltration and beginning of chromatography. Samples were measured and compared immediately after diafiltration and right before loading the chromatographic column.

Despite the relatively short hold time between the ultra/diafiltration steps and additional purification steps, a significant loss of A13 specific activity (23.3%) occurred when the diafiltration buffer lacked zinc and calcium. In contrast, when the diafiltration buffer contained 2 mM Ca and 5 μM Zn was used, the loss of A13 specific activity (7.3%) was greatly reduced (Table 22).

TABLE 22

Results of diafiltration experiments using diafiltration buffer with and without calcium and zinc.

| Sample | Diafiltration | Specific Activity After Filtration | Specific Activity in Purification Load | % Loss in Activity |
|---|---|---|---|---|
| 1 | w/o Ca/Zn | 999 | 740 | 25.9 |
| 2 | w/o Ca/Zn | 924 | 734 | 20.6 |

TABLE 21

Fermentation data for chemostat cell-culture experiments with additional supplementation of zinc.

| Additional Zinc | Cell Concentration [$10^6$ Cells/ml] | Specific Growth Rate [1/d] | Dilution Rate [1/d] | Cell Viability [%] | A13 FRETS [mU/ml] | A13 ELISA [μg/ml] | Specific Activity [mU/μg] | FRETS Yield [U/L/d] | A13 Yield [mg/L/d] | Glucose Consumption [g/L/d] |
|---|---|---|---|---|---|---|---|---|---|---|
| 1.0 mg/L | 1.28 | 0.256 | 0.336 | 88.6 | 2716.0 | 3.127 | 868 | 911.5 | 1.050 | 1.21 |
| 2.0 mg/L | 0.55 | 0.091 | 0.321 | 72.1 | 1408.9 | 1.632 | 863 | 452.7 | 0.524 | 0.58 |
| 3.0 mg/L | 0.56 | 0.134 | 0.321 | 80.4 | 1359.8 | 1.763 | 771 | 436.5 | 0.566 | 0.64 |

Example 6

Human A13 protein was expressed in the recombinant CHO cell line #640-2 in a chemically defined BACD-A13 medium supplemented with additional zinc and nicotinamide in 50 L bioreactors. After harvesting the supernatants of the cultures, a comparison of Ultra/Diafiltration (50 kD) steps using buffers with and without zinc and calcium was performed.

Recombinant CHO cells expressing human ADAMTS13 were adapted to a chemically defined proprietary medium, BCS medium. Briefly, a DWCB was thawed and cell inoculum was prepared in BCS medium. Cells were transferred via 10 L a bioreactor to a 50 L bioreactor with Rushton type impellers and cultivated in chemostat mode in proprietary BACD-A13 medium under an inline controlled pH of 7.15-7.20 at 37° C. with a dissolved oxygen concentration of 20% air saturation.

Supernatants from the bioreactors were filtered and cell-free harvests were ultrafiltrated using a 50 kD PES membrane (concentration factor approximately 1:10) and then diafiltered with 5 volumes of a buffer containing 50 mM NaCl and 20 mM TRIS at pH 7.7. Diafiltration buffer with or without 2 mM Ca and 5 μM Zn was compared to determine the effect on activity loss between diafiltration and chromatographic purification.

Specific activities, recorded as mU FRETS-VWF73 per μg A13 detected by ELISA, were determined immediately after diafiltration and right before loading the sample for further purification. The samples were stored at between about 2 and 8° C. for a maximum time of 3 days (about less than 80 hours). When samples were stored for longer periods TABLE 22-continued Results of diafiltration experiments using diafiltration buffer with and without calcium and zinc.

| Sample | Diafiltration | Specific Activity After Filtration | Specific Activity in Purification Load | % Loss in Activity |
|---|---|---|---|---|
| Mean | w/o Ca/Zn | 962 | 737 | 23.3 |
| Std. dev | w/o Ca/Zn | 53 | 4.2 | N/A |
| 3 | with Ca/Zn | 849 | 835 | 1.6 |
| 4 | with Ca/Zn | 951 | 985 | −3.6 |
| 5 | with Ca/Zn | 929 | 877 | 5.6 |
| 6 | with Ca/Zn | 1131 | 844 | 25.4 |
| Mean | with Ca/Zn | 965 | 885 | 7.3 |
| Std. dev | with Ca/Zn | 119 | 68.9 | N/A |

Example 7

Chemostat and perfusion continuous cell-culture methods were compared to determine the relative production and specific activities of A13 expressed in several recombinant CHO cell lines.

Briefly, different clones of recombinant CHO cell expressing recombinant human A13 were adapted to a chemically defined proprietary medium (BCS), which was used for inoculums preparation. Cells were further cultivated in bioreactor cultures in proprietary BACD-A13 medium supplemented with zinc and nicotinamide at final concentrations of 1.432 mg/L $ZnSO_4.7H_2O$ and 7.02 mg/L nicotinamide. Inocula from each cell clone were then transferred to two bioreactors, of which one was cultured under chemostatic conditions (CST) and the other under perfusion, as indicated in Table 23. Cells were cultured at a density of between about $2\times10^6$ and $4\times10^6$ cells/ml on Cytopore™ II microcarriers (GE Biosciences).

Cultures were grown under continuous culture conditions for 3 to 4 weeks and samples of the supernatant from the bioreactors were analyzed periodically for A13 protein production by ELISA and A13 activity by FRETS-VWF73 assay. Values given in Table 23 represent averages for the 3 to 4 week period. Consistent with results obtained in examples 1 to 6 above, cultures grown under chemostatic produced about 1 mg/L/d to about 2 mg/L/d of A13 protein having high specific activities of about 700 mU/μg to about 1000 mU/μg (Table 23). Strikingly, cultures grown under perfusion culture conditions consistently demonstrated higher protein production and activity levels of A13 in the culture supernatant than did the identical clones grown under chemostatic conditions. Specific activities for A13 produced in the perfusion cultures were very high, with three of the four clones demonstrating at least about 1000 mU/μg.

TABLE 23

Results from experiments comparing chemostat and perfusion cell-cultivation.

| Clone | Volume [L] | Mode | Specific activity [mU/μg] | FRETS Yield [U/L/d] | A13 Yield [mg/L/d] |
|---|---|---|---|---|---|
| F6 | 50.0 | CST | 800 | 800 | 1.0 |
| F6 | 10.0 | Perfusion | 1000 | 1600 | 1.6 |
| D6 | 1.5 | CST | 690 | 900 | 1.3 |
| D6 | 1.5 | Perfusion | 890 | 1700 | 1.9 |
| X1 | 1.5 | CST | 1040 | 2400 | 2.3 |
| X1 | 1.5 | Perfusion | 1000 | 2600 | 2.6 |
| E2 | 1.5 | CST | 710 | 500 | 0.7 |
| E2 | 1.5 | Perfusion | 1000 | 1600 | 1.6 |

Example 8

In order to determine the effect of temperature and pH on the production of recombinant human ADAMTS13 protein grown in eukaryotic cell culture using a chemically defined animal protein-free culture medium, cultures were grown at temperatures between 35.0° C. and 38.0° C. at pH's of between 7.05 and 7.30.

Briefly, recombinant CHO cells expressing human A13 were transferred to 1.5 L bioreactors with blade impellers, in proprietary BACD-A13 medium. Cultures were grown under inline controlled pH's between 7.05 and 7.30 at temperatures ranging from 35.0° C. to 38.0° C. with a dissolved oxygen concentration of 20% air saturation. The experiments were designed and executed using the response surface approach. The statistical analysis was done using the statistical Software package Minitab® 15.1.0.0.

Samples from the bioreactors were taken and analyzed for A13 by ELISA, A13 activity was measured by FRETS-VWF73 assay. Cell counts were determined by Nucleocounter technology. Dilution rates were measured and used for calculation of growth rates and volumetric productivities.

Figure 1B:
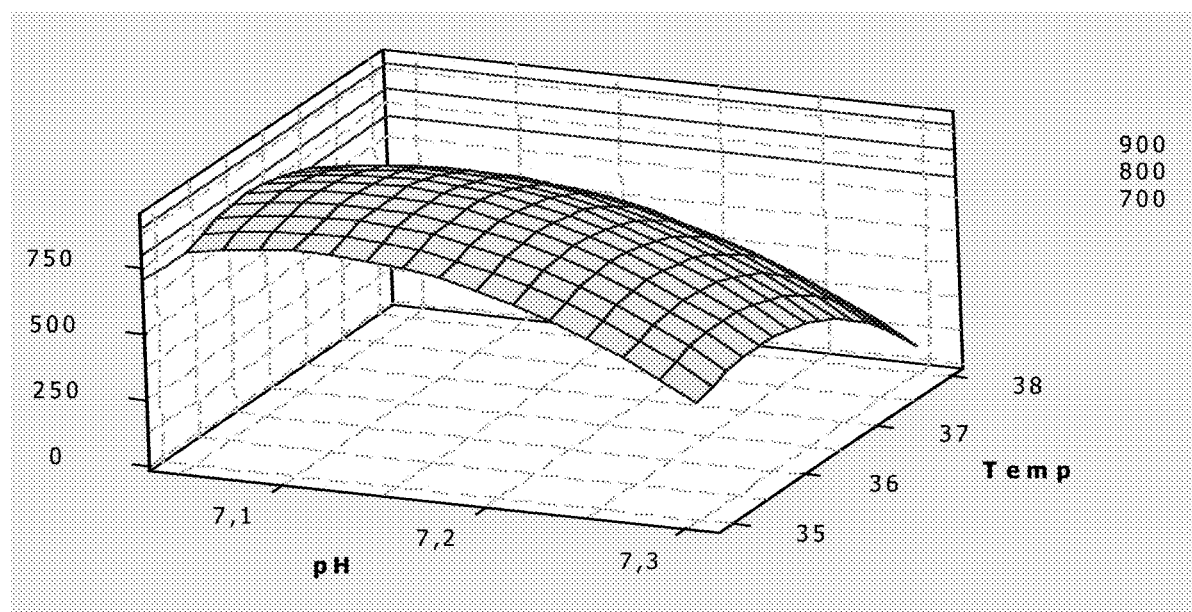

As can be seen in FIGS. 1 and 2, both temperature and pH had a substantial effect on the volumetric A13 productivity (measured by FRETS-VWF73, FIG. 1), and specific activity (FRETS-VWF73 activity/antigen by ELISA, FIG. 2). Specifically, maximal volumetric FRETS productivity was achieved in cultures grown in a lower pH range between about 7.05 and 7.2, especially about 7.10 and temperatures between about 35.0° C. and 37.0° C., especially about 36° C. Specifically, maximal specific activity (FRETS-VWF73 to antigen by ELISA) was achieved in cultures grown in a lower pH range between about 7.05 and 7.2, especially below 7.10 and temperatures between about 35.0° C. and 37.0° C., especially below 36° C. Specifically optimal conditions for A13 production were achieved with a combination of a temperature of about 36° C. and a pH of about 7.10 in terms of optimal yield and product quality.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for expressing a disintegrin and metalloproteinase with thrombospondin motifs (ADAMTS) protein, the method comprising culturing, by continuous cultivation, a mammalian cell harboring a nucleic acid encoding an ADAMTS protein in a culture medium comprising at least 3 μM zinc, wherein the continuous cultivation includes maintaining a cell density of from $1\times10^6$ cells/mL to $4\times10^6$ cells/mL for at least seven days.

2. The method of claim 1, wherein the culture medium comprises from 3 μM to 12 μM zinc.

3. The method of claim 1, wherein the culture medium comprises about 5 μM zinc.

4. The method of claim 1, wherein the culture medium further comprises from 0.5 mM to 1.5 mM calcium.

5. The method of claim 2, wherein the culture medium further comprises from 0.5 mM to 1.5 mM calcium.

6. The method of claim 3, wherein the culture medium further comprises from 0.5 mM to 1.5 mM calcium.

7. The method of claim 1, wherein the mammalian cell is selected from the group consisting of a CHO cell, a BHK cell, and an HEK cell.

8. The method of claim 2, wherein the mammalian cell is selected from the group consisting of a CHO cell, a BHK cell, and an HEK cell.

9. The method of claim 3, wherein the mammalian cell is selected from the group consisting of a CHO cell, a BHK cell, and an HEK cell.

10. The method of claim 1, wherein the continuous cultivation is chemostatic cell cultivation.

11. The method of claim 2, wherein the continuous cultivation is chemostatic cell cultivation.

12. The method of claim 3, wherein the continuous cultivation is chemostatic cell cultivation.

13. The method of claim 8, wherein the continuous cultivation is chemostatic cell cultivation.

14. The method of claim 1, wherein the ADAMTS13 protein is a human ADAMTS13 protein.

15. The method of claim 2, wherein the ADAMTS13 protein is a human ADAMTS13 protein.

16. The method of claim 3, wherein the ADAMTS13 protein is a human ADAMTS13 protein.

17. The method of claim 8, wherein the ADAMTS13 protein is a human ADAMTS13 protein.

18. The method of claim 10, wherein the ADAMTS13 protein is a human ADAMTS13 protein.

19. The method of claim 11, wherein the ADAMTS13 protein is a human ADAMTS13 protein.

20. The method of claim 13, wherein the ADAMTS13 protein is a human ADAMTS13 protein.

* * * * *